*(12)* United States Patent
Ye et al.

US008921655B2

(10) Patent No.: US 8,921,655 B2
(45) Date of Patent: Dec. 30, 2014

(54) **FUNCTIONAL ANALYSIS OF *JATROPHA CURCAS* GENES**

(75) Inventors: Jian Ye, Singapore (SG); Nam Hai Chua, New York, NY (US); Jing Qu, Singapore (SG)

(73) Assignee: Joil (S) Pte Ltd., Singapore (SG)

( * ) Notice: Subject to any disclaimer, the term of this patent is extended or adjusted under 35 U.S.C. 154(b) by 757 days.

(21) Appl. No.: 13/141,752

(22) PCT Filed: Dec. 16, 2009

(86) PCT No.: PCT/SG2009/000481
§ 371 (c)(1),
(2), (4) Date: Jun. 23, 2011

(87) PCT Pub. No.: WO2010/080071
PCT Pub. Date: Jul. 15, 2010

(65) Prior Publication Data
US 2011/0265223 A1    Oct. 27, 2011

Related U.S. Application Data

(60) Provisional application No. 61/143,484, filed on Jan. 9, 2009.

(51) Int. Cl.
| | | |
|---|---|---|
| *C12N 15/11* | (2006.01) | |
| *C07H 21/04* | (2006.01) | |
| *C12N 15/113* | (2010.01) | |
| *C12N 15/63* | (2006.01) | |
| *C12N 15/82* | (2006.01) | |
| *C12N 15/83* | (2006.01) | |
| *C12N 15/84* | (2006.01) | |
| *A01H 5/00* | (2006.01) | |

(52) U.S. Cl.
CPC .................................. *C12N 15/8218* (2013.01)
USPC .... 800/286; 536/23.72; 536/24.5; 435/320.1; 435/468; 435/469; 435/91.4; 800/280; 800/281; 800/278; 800/294; 800/285

(58) Field of Classification Search
None
See application file for complete search history.

(56) References Cited

U.S. PATENT DOCUMENTS

| 6,369,296 B1 * | 4/2002 | Ratcliff et al. ................ 800/278 |
| 7,229,829 B2 | 6/2007 | Dinesh Kumar et al. |
| 2003/0182684 A1 | 9/2003 | Dinesh Kumar et al. |

FOREIGN PATENT DOCUMENTS

| KR | 100856930 | 9/2008 |
| WO | 2009130695 A2 | 10/2009 |

OTHER PUBLICATIONS

Li et al (Plant Cell Tiss Organ Cult, 92, pp. 173-181, 2008; Published online: Dec. 1, 2007).*
Wege et al (Annals of Botany, 100, pp. 641-649, 2007).*
Gould et al (Plant Methods, 3(6), 12 pages, 2007).*
Chen et al (Plant Molecular Biology, 55, pp. 521-530, 2004).*
Ding et al (Cell, 130(3), pp. 413-426, 2007).*
Tong et al (Journal of Shanghai University, 11(2), pp. 182-188, 2007).*
First Chinese Office Action with English translation of CN Application No. 200980154211.8 dated Jun. 13, 2012, 8 pages.
Tang, Q. et al., Use of Tobacco Rattle Virus-Induced Gene Silencing in Functional Study of Plant Genes, Chemistry of Life, vol. 2, No. 4, pp. 360-363, Dec. 31, 2006, 5 pages.
Li, M. et al., "Study on Factors Influencing Agrobacterium-Mediated Transformation of *Jatropha curcas*," Journal of Molecular Cell Biology, vol. 39, No. 1, pp. 83-89, Feb. 2006, (with abstract enclosed), plus 2 pages of bibliographic details.
Ye, J. et al., "Rapid analysis of *Jatropha curcas* gene functions by virus-induced gene silencing," Plant Biotechnology Journal, 2009, vol. 7, pp. 964-976.
He, Y. et al., "*Agrobacterium tumefaciens*-mediated transformation of *Jatropha curcas*: factors affecting transient transformation efficiency and morphology analysis of transgenic calli," Silvae Genetica, 2009, vol. 58, No. 3, pp. 123-128.
Li, M. et al., "Establishment of an *Agrobacterium*-mediated cotyledon disc transformation method for *Jatropha curcas*," Plant Cell Tissue Organ Culture, 2008, vol. 92, pp. 173-181.
Gould, B. et al., "Virus-Induced Gene Silencing as a Tool for Functional Analyses in the Emerging Model Plant *Aquilegia* (Columbine, Ranunculaceae)," Plant Methods, vol. 3, No. 6, Apr. 12, 2007, 12 pages.

\* cited by examiner

*Primary Examiner* — David T Fox
*Assistant Examiner* — Stephen Uyeno
(74) *Attorney, Agent, or Firm* — Rothwell, Figg, Ernst & Manbeck P.C.

(57) ABSTRACT

The present invention relates to the field of functional analysis of *Jatropha* genes on a genomic scale. More specifically, the present invention relates to a method for high-throughput functional analysis of *Jatropha curcas* genes on a genomic scale using virus-induced gene silencing. The method involves use of the tobacco rattle virus (TRV).

22 Claims, 11 Drawing Sheets

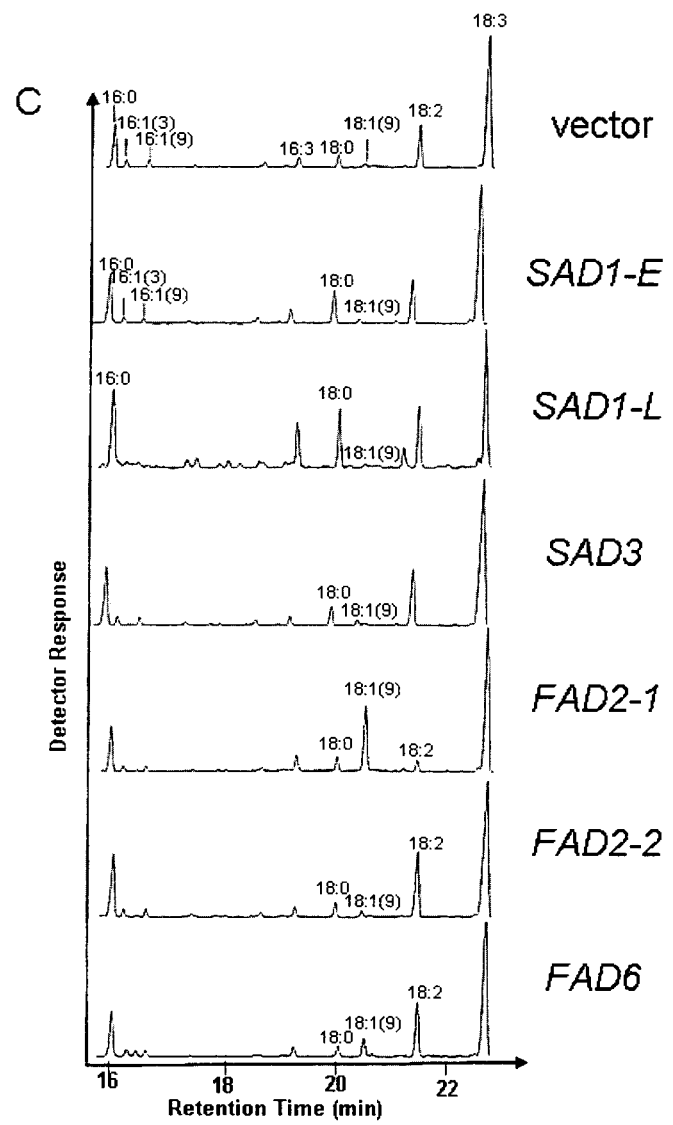
Figure 8 (Con't)

A

Figure 9 (Con't)

FUNCTIONAL ANALYSIS OF *JATROPHA CURCAS* GENES

CROSS-REFERENCE TO RELATED APPLICATION

The present application is a national stage filing under 35 U.S.C. §371 of PCT/SG2009/000481 filed on 16 Dec. 2009, and claims priority to U.S. provisional patent application Ser. No. 61/143,484 filed 9 Jan. 2009, each application is incorporated herein by reference in its entirety.

BACKGROUND OF THE INVENTION

The present invention relates to the field of functional analysis of *Jatropha* genes on a genomic scale. More specifically, the present invention relates to a method for high-throughput functional analysis of *Jatropha curcas* genes on a genomic scale using virus-induced gene silencing.

The publications and other materials used herein to illuminate the background of the invention or provide additional details respecting the practice, are incorporated by reference, and for convenience are respectively grouped in the Bibliography.

The world is facing dwindling supply is fossil fuel and worsening Green House Effect. There is an urgent demand to increase production and consumption of renewable energy. Biofuels have been recognized as a national priority for many countries in their search for alternative sources to meet their energy security needs and at the same time help reduce CO/emissions that cause the Green House Effect. The demand for biofuel has put increasing pressure on food production. For example, to satisfy the biofuel need for Germany in 2017 as mandated by the German government the entire farm land of this country would have to be used for growing bioenergy crops with no land left for food production. To ease this competition for land and to satisfy our need for renewable fuels, there is a strong need to utilize marginal land for bioenergy production.

*Jatropha curcas* is a small woody plant belonging to the Euphorbiaceae family. Several unique characters of *Jatropha curcas* make it an ideal plant for biodiesel production. These include its rapid growth, easy propagation, low cost of seeds, high oil content, short gestation period, wide adaptability, drought tolerance and the ability to thrive on degraded soils. Moreover, its plant size renders convenient collection of seed (Jones, 1991; Sujatha et al., 2008).

However, *Jatropha* suffers from several shortcomings that may limit its wide adoption. The productivity of the plant is constrained by the unfavourable male to female flower ratio and its oil content has not been optimized by breeding. This plant is also sensitive to biotic stresses such as viral (Narayanna et al., 2007), fungal and bacterium pathogens and abiotic stresses, especially cold and drought (http colon www dot jatropha dot org). The presence of several toxic components (e.g. the protein toxin, curcin, and the cancer-causing agent phorbol esters) in seeds and leaves of the plant possess health hazards for farmers and bioprocess workers in the *Jatropha* industry.

An important strategy to improve agronomic and quality traits of *Jatropha curcas* is by genetic modification. Transgenic *Jatropha* plants can be generated expressing homologous or heterologous gene sequences. In many instances, over-expression or silencing by RNAi of one or more homologous genes of defined function is desired. Gene sequences of *Jatropha* can be obtained from cDNA and genomic libraries and functions of genes can be tentatively assigned by sequence homology with other plant genes of known function. However, such assignment at best is only provisional and tentative. Quite often functional assignment is confounded by the presence of a gene family whose members are highly related in sequences. Gene function can be more accurately determined by over-expression or RNAi-mediated silencing of candidate genes in transgenic plants; however, such procedure is laborious and time consuming and not suitable for high throughput analysis on a genomic scale.

Thus, it is desired to develop a method for the high-throughput functional analysis of *Jatropha curcas* genes on a genomic scale.

SUMMARY OF THE INVENTION

The present invention relates to the field of functional analysis of *Jatropha* genes on a genomic scale. More specifically, the present invention relates to a method for high-throughput functional analysis of *Jatropha curcas* genes on a genomic scale using virus-induced gene silencing.

The present invention relates to the use of virus-induced gene silencing (VIGS) to evaluate gene function in *Jatropha curcas* reliably and rapidly, and in a high-throughput manner. In one aspect, the present invention provides an efficient and reproducible system and procedure for VIGS in *J. curcas*. In one embodiment, the present invention provides for the co-silencing of DCL4 to enhance the VIGS efficiency. In another embodiment, the present invention provides for the further re-synthesis of the whole tobacco rattle virus (TRV) viral genomes. In an additional embodiment, the present invention demonstrates that these vectors have similar efficiency as the original vectors. In a further embodiment, the present invention provides for the use of TRV VIGS system for cloning and functional identifying several important fatty acid biogenesis pathway genes. These important genes can be used to improve fuel properties of biodiesel such as cold-temperature flow characteristics, oxidative stability and NOx emissions.

Thus in a first aspect, the present invention provides a method of virus-induced gene silencing (VIGS) in *Jatropha*. In accordance with the present invention, the method comprises:

(a) inserting a nucleic acid comprising a sequence of a first desired gene to be silenced into a vector comprising a tobacco rattle virus (TRV) RNA2 sequence to produce a modified TRV RNA2 vector;

(b) preparing a mixed culture of *Agrobacterium* comprising *Agrobacterium* containing a vector comprising a TRV RNA1 sequence and *Agrobacterium* containing the modified TRV RNA2 vector;

(c) introducing the mixed culture of *Agrobacterium* into plant tissue of *Jatropha* by vacuum infiltration to produce infected plants; and (d) growing the infected plants for a sufficient time to induce gene silencing of the desired gene.

In one embodiment, the vector comprising TRV RNA2 and the vector comprising TRV RNA1 are synthetic plant vectors. In another embodiment, the sequence of the first desired gene is the sequence of a sense strand of the gene. In an additional embodiment, the sequence of the first desired gene is the sequence of an antisense strand of the gene. In a further embodiment, the nucleic acid further comprises a sequence of a second desired gene to be silenced. In one embodiment, the second desired gene is virus resistance gene. In another embodiment, the virus resistance gene is selected from the group consisting of RNase III Dicer-like 4 (DCL4) gene, RNase III Dicer-like 2 (DCL2) gene, RNase III Dicer-like 3

(DCL3) gene, ARGONAUTE1 (AGO1), ARGONAUTE71 (AGO 7), RNA-dependent RNA polymerase 1 (RDR1), RNA-dependent RNA polymerase 6 (RDR6), Suppressor of gene silencing 1 (SGS1), Suppressor of gene silencing 3 (SGS3), and Silencing defective 3 (SDE3). In a further embodiment, the nucleic acid comprises sequences of more than two desired genes to be silenced.

In some embodiments, the desired gene is a candidate gene in fatty acid biosynthesis, such as a β-ketoacyl-acyl carrier protein synthase II (KASII) gene, an acyl-acyl carrier protein thioesterase B (FATB) gene, a stearoyl-acyl carrier protein desaturase (SAD) gene, and a fatty acid desaturase (FAD) gene. In other embodiments, the desired gene is a candidate transcription factor gene. In one embodiment, the desired gene is a candidate gene in small RNA (smRNA) biosynthesis. In another embodiment, the desired gene is a candidate gene in biosynthesis of toxic agents.

Thus in a first aspect, the present invention provides a method of analyzing gene function in *Jatropha*. In accordance with the present invention, the method comprises:

(a) inserting a nucleic acid comprising a sequence of a candidate gene to be silenced into a vector comprising a tobacco rattle virus (TRV) RNA2 sequence to produce a modified TRV RNA2 vector;

(b) preparing a mixed culture of *Agrobacterium* comprising *Agrobacterium* containing a vector comprising a TRV RNA1 sequence and *Agrobacterium* containing the modified TRV RNA2 vector;

(c) introducing the mixed culture of *Agrobacterium* into plant tissue of *Jatropha* by vacuum infiltration to produce infected plants;

(d) growing the infected plants for a sufficient time to induce gene silencing of the candidate gene; and analyzing the phenotypic effect of the silenced candidate gene on the infected plant.

In one embodiment, the vector comprising TRV RNA2 and the vector comprising TRV RNA1 are synthetic plant vectors. In another embodiment, the sequence of the first desired gene is the sequence of a sense strand of the gene. In an additional embodiment, the sequence of the first desired gene is the sequence of an antisense strand of the gene. In a further embodiment, the nucleic acid further comprises a sequence of a second desired gene to be silenced. In one embodiment, the second desired gene is virus resistance gene. In another embodiment, the virus resistance gene is selected from the group consisting of RNase III Dicer-like 4 (DCL4) gene, RNase III Dicer-like 2 (DCL2) gene, RNase III Dicer-like 3 (DCL3) gene, ARGONAUTE1 (AGO1), ARGONAUTE71 (AGO7), RNA-dependent RNA polymerase 1 (RDR1), RNA-dependent RNA polymerase 6 (RDR6), Suppressor of gene silencing 1 (SGS1), Suppressor of gene silencing 3 (SGS3), and Silencing defective 3 (SDE3). In a further embodiment, the nucleic acid comprises sequences of more than two desired genes to be silenced.

In some embodiments, the desired gene is a candidate gene in fatty acid biosynthesis, such as a β-ketoacyl-acyl carrier protein synthase II (KASII) gene, an acyl-acyl carrier protein thioesterase B (FATB) gene, a stearoyl-acyl carrier protein desaturase (SAD) gene, and a fatty acid desaturase (FAD) gene. In other embodiments, the desired gene is a candidate transcription factor gene. In one embodiment, the desired gene is a candidate gene in smRNA biosynthesis. In another embodiment, the desired gene is a candidate gene in biosynthesis of toxic agents.

BRIEF DESCRIPTION OF THE FIGURES

FIG. 2D: The silencing signal can travel downwards from the inoculated leaf (indicated by a black arrow) to produce gene silencing effects in a newly emerged lateral leaf (indicated by a white arrow) FIG. 2E: RT-PCR analysis to determine *J. curcas* CH42 RNA levels in the upper leaves of longer CH42 insertion TRV-CH42L infected (lane 1), short CH42 insertion TRV-CH42S infected (lane 2-3) and vector control infected (lane CK) infected *J. curcas* plants. The first strand cDNA was generated from total RNA isolated from silenced and non-silenced plants using oligo (dT) primer and reverse transcriptase. The first strand cDNA was used in a PCR reaction using gene specific primers. Ethidium bromide-stained agarose gels showing RT-PCR products after 30 cycles. PCR products of the rbcL gene transcript were used as loading controls.

FIG. 3A: CH42 silencing using original TRV vector. FIG. 3B: CH42 silencing using the synthetic TRV vector.

FIG. 4E: Quantitative PT-PCR analysis to show the relative PDS RNA level of silenced *J. curcas* leaves in FIG. 4C and FIG. 4D. Average values from three independent repeats are shown along with error bars. ** indicates lower PDS RNA levels of plants silenced with TRV-PDS-600 compared to that silenced with TRV-PDS-300. Vacuum infiltration helps better silencing efficiency in CH42 gene silencing (compare agro-injection data in FIG. 4F with vacuum infiltration data in FIG. 4G).

FIG. 5D: abaxial side of leaf). *J. curcas* plants were infected with recombinant TRV-PCNA or TRV-PCNA co-CH42 by vacuum infiltration. TRV-PCNA co-CH42 carried an insert containing both the *J. curcas* PCNA and CH42 gene fragments. Silencing by vacuum infiltration showed a better silencing effect than that of syringe-based agro-injection. FIG. 5E: Quantitative RT-PCR analysis to show the relative PCNA and CH42 RNA levels of silenced

*J. curcas* leaves. Average values of three independent experiments are shown along with error bars.

Figure 6:
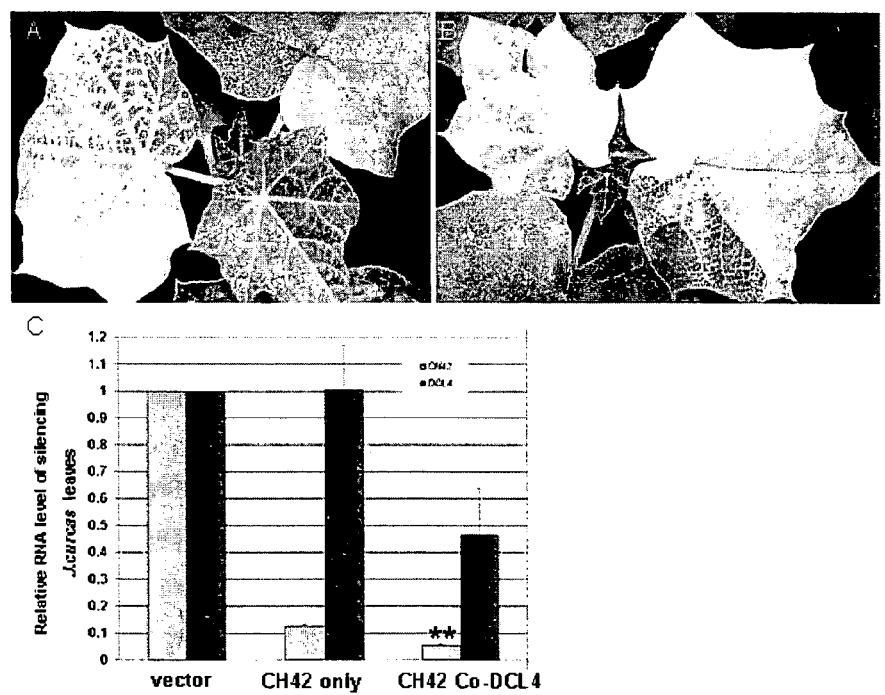

FIGS. 6A-6C show co-silencing of DCL4 and CH42 to enhance VIGS efficiency. Silencing of the CH42 gene alone (FIG. 6A) and co-silencing of DCL4 and CH42 (FIG. 6B). FIG. 6C: Quantitative RT-PCR analysis to show the relative DCL4 and CH42 RNA levels of silenced *J. curcas* leaves. Average values of 3 independent experiments are shown along with error bars. ** indicates a higher silencing efficiency in leaves co-silenced for both the CH42 and DCL4 genes as compared to leaves silenced for the CH42 gene alone ($p<0.01$).

Figure 7:
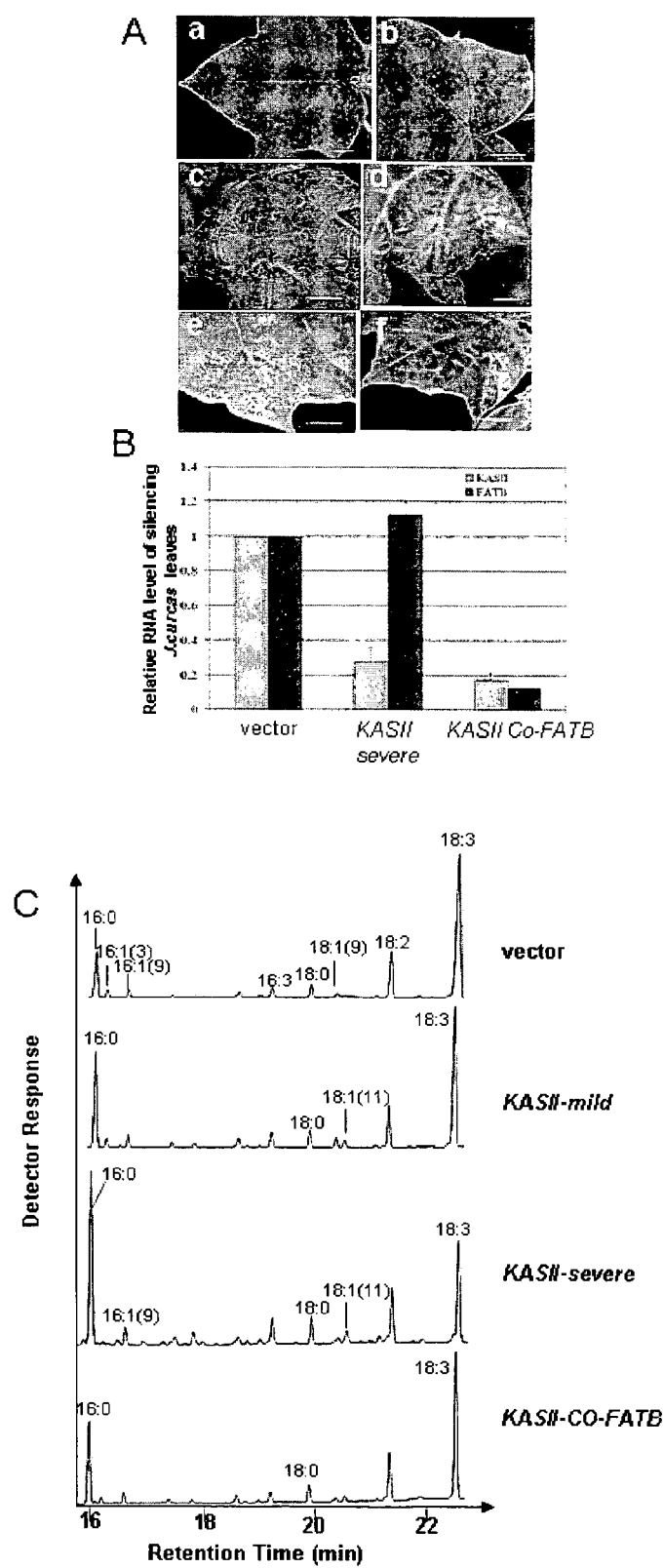

FIGS. 7A-7C show silencing of the *Jatropha* KASII gene encoding β-keto acyl-acyl carrier protein synthase II by TRV VIGS.

FIG. 7A: Phenotypes of silenced *J. curcas* plants infected with different TRV constructs 18 days post-TRV infiltration. Panel (a): *J. curcas* plant treated with empty TRV vector. Panel (b): *J. curcas* plants infected with TRV:KASII with mild yellowish phenotypes. Panels (c) and (d): *J. curcas* plants infected with TRV:KASII with severe phenotypes. Treated plants showed downwards curling of newly emerged leaves, brownish leaves blade and reduced shoot extension. Panels (e) and (f): Antagonist effects of the *J. curcas* FATB1 gene and the KASII gene. The FAT1B gene encodes acyl-ACP thioesterase. We used the vector, TRV:KASII Co-FATB1, to co-silence *Jatropha* KASII as well as FATB1. Leaves of infected plants displayed yellowish phenotype along leaf veins very similar to the mild phenotypes found in TRV:KASII only infected leaves. Scale bars=10 mm.

FIG. 7B: Quantitative RT-PCR analysis of KASII and FATB gene expression levels in silenced *J. curcas* leaves. Panel (a): Vector control. Panel (b): plant silenced in KASII expression. Panel (c): plant silenced in KASII expression with severe phenotype in FIG. 2A. Panel (d) same as Panel (b), except injected plants showed severe phenotype. Panels (e) and (f): leaves from plants co-silenced in KASII and FATB gene expression. KASII and FATB transcript levels were quantified by amplification using gene specific primers. No significant difference was found in FATB gene expression level between vector control plant and KASII-silenced plant.

FIG. 7C: Gas chromatograms of fatty acid methyl esters from silenced *J. curcas* leaves: vector, vector control; KASII-mild, leaves from plants silenced in KASII expression displaying mild phenotype. These plants showed mild yellowish phenotype and modest increase in 16:0 accumulation (KASII mild); KASII-severe, plants silenced in KASII expression but with severe phenotype Note the significant increase in 16:0 accumulation (KASII severe); KASII CO FATB, plants co-silenced in KASII and FATB1 gene expression. Methyl esters are labeled: 16:0 (peak 1), $16:1^3$ (peak 2), cis-$16:1^9$ (peak 3), 16:3 (peak 4), 18:0 (peak 5), cis-$18:1\Delta^9$ (peak 6), $18:1\Delta^{11}$ (peak 7), cis-$18:2^{9, 12}$ (peak 8), and cis-$18:3^{9, 12, 15}$ (peak 9).

Figure 8:
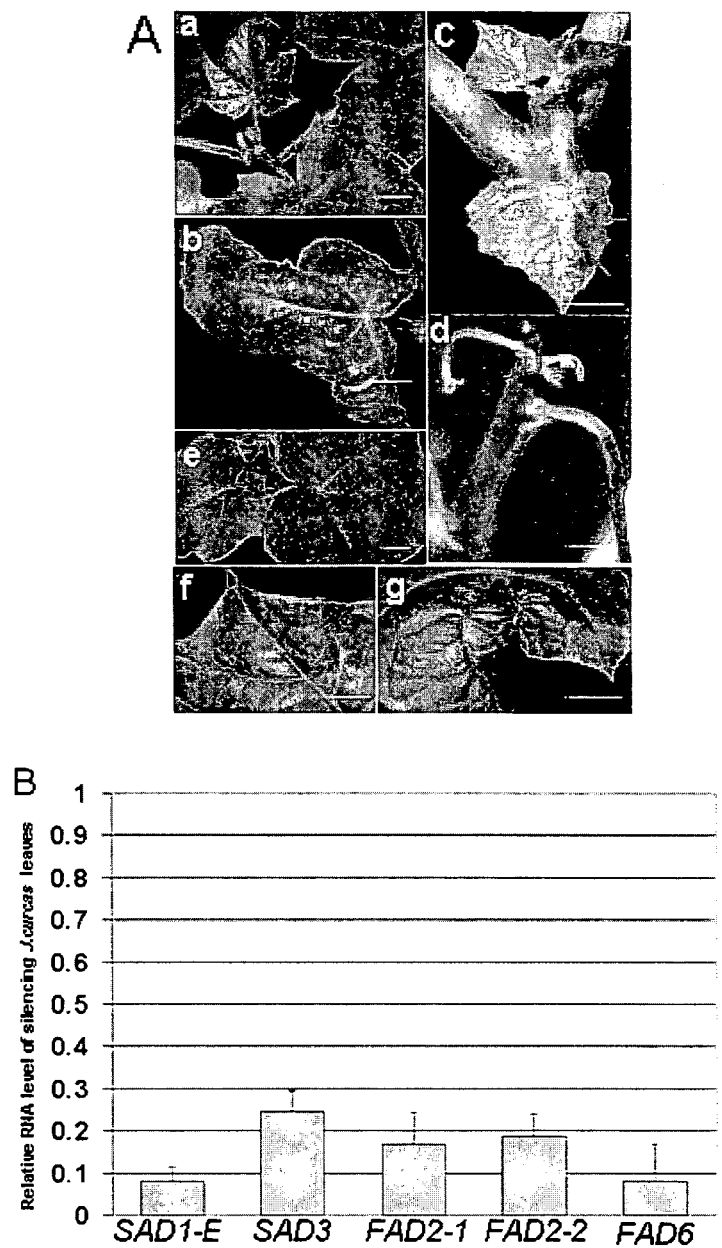

FIGS. 8A-8C show silencing of expression of several desaturase genes by TRV VIGS system in *J. curcas*.

FIG. 8A: Phenotypes of *J. curcas* plants with silenced expression of individual members of the stearoyl-ACP desaturase (SAD) gene family. Plant infiltrated with TRV constructs were analyzed 18 days post-infiltration. Panel (a): Empty vector-treated *J. curcas* plant. Panels (b)-(d): *J. curcas* plants infected with TRV:SAD1 showed severe phenotypes at the early stage (12 dpi) with downward curled, narrow leaf blades and brownish leaf vein shown in (panel (b)); and later stages (18 dpi) in (panels (c) and (d)). Panel (e): TRV:SAD2 treatment did not produced any apparent phenotype. Panels (f) and (g): TRV:SAD3 caused much weaker phenotype than that of plants infected with TRV:SAD1. Scale bar=10 mm.

FIG. 8B: Real-time RT-PCR quantification of SAD gene expression levels infected *J. curcas* plants. Relative SAD1 gene transcript level in TRV: SAD1 early stage samples (SAD1-E).

Figure 3:
FIGS. 3A and 3B show silencing efficiency is similar with the synthetic TRV vector compared with the original TRV vectors.

FIG. 8C: Gas chromatograms of fatty acid methyl esters from leaf samples of *Jatropha* plants with silenced expression of three SAD gene family members and three oleate desaturase genes: Vector, empty vector control; SAD1-E, samples from plants at early stage of TRV:SAD1 infection. Leaf phenotypes of plants are shown in FIG. 3A; SAD1-L, samples from plants at late stage of TRV:SAD1 infection; FAD2-1, samples from plants treated with TRV-FAD2-1; FAD2-2, samples from plants treated with TRV-FAD2-2; FAD6, samples form plants treated with TRV-FAD6. Note that FAD6 is located in the ER. Methyl esters are labeled: 16:0 (peak 1), $16:1^3$ (peak 2), cis-$16:1^9$ (peak 3), 16:3 (peak 4), 18:0 (peak 5), cis-$18:1\Delta^9$ (peak 6), cis-$18:2^{9, 12}$ (peak 7), and cis-$18:3^{9, 12, 15}$ (peak 8). Unknown peak is noted as peak 9.

FIGS. 9A-9I show *J. curcas* plants with silenced expression of key genes regulating plant development.

Figure 9:
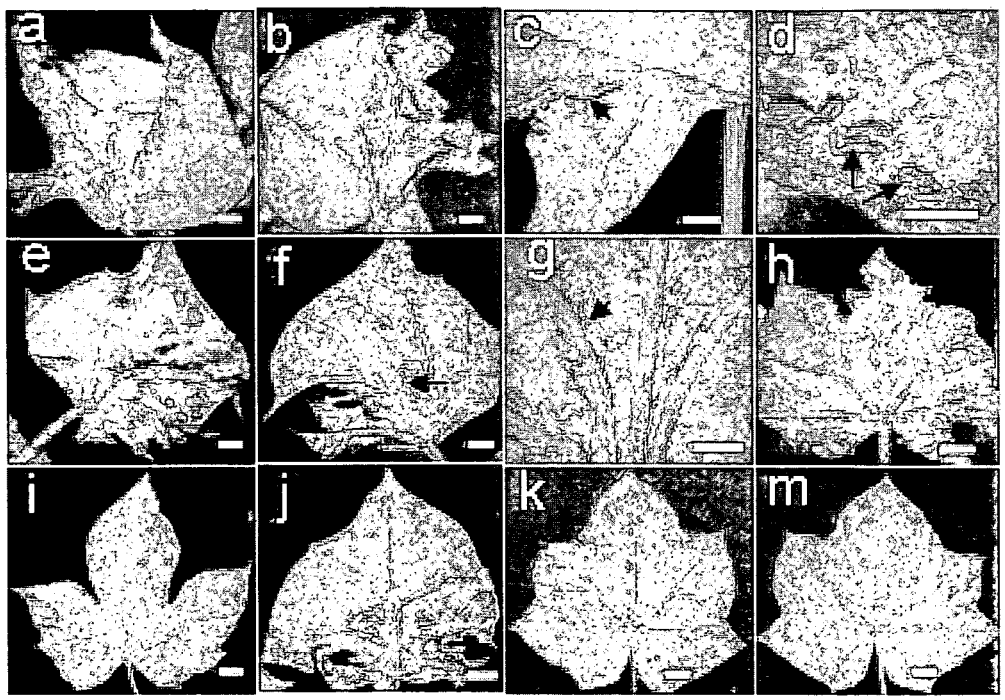
Figure 9:
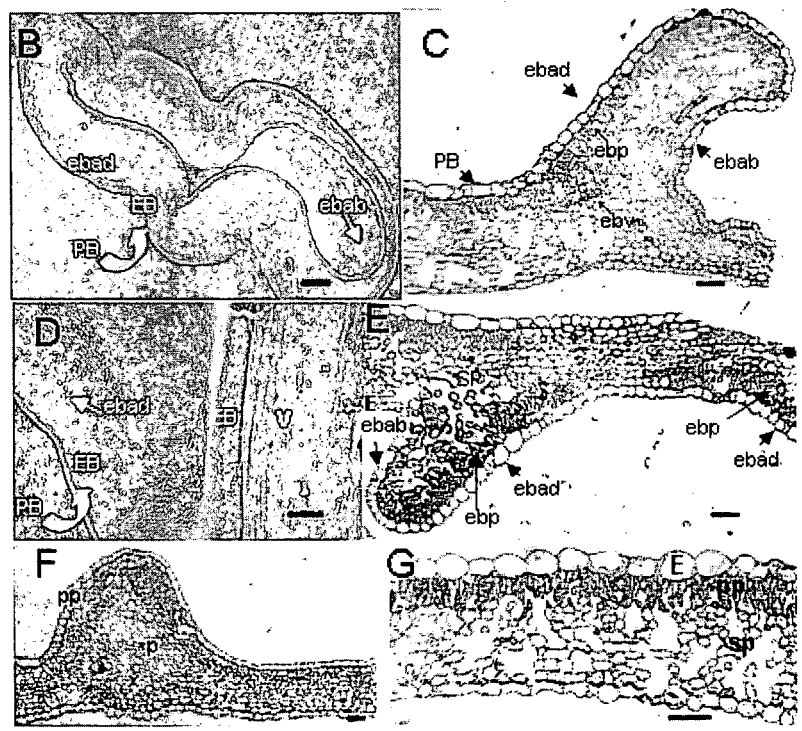

FIG. 9A: Phenotypes of *J. curcas* plants infected with TRV VIGS constructs at 27 dpi except i and j were taken at 42 dpi. Panels (a)-(d): *J. curcas* plants infected with TRV:AS1. (panel (a)) adaxial side and (panel (b)) abaxial side of downward curled leaves from infected plants. Panel (c): Adaxial ectopic leaf blade along the leaf vein on leaf of treated *J. curcas* plants. Panel (d): High magnification view of the adaxial ectopic leaf blade and bubble structure in leaves of treated *J. curcas* plants. Panels (e)-(j): Leaves of *J. curcas* plant infected with TRV:AGO1. Panel (e) adaxial side and panel (f) abaxial side of upward curled leaves of treated *J. curcas* plants. Panel (g): High magnification view of the abaxial ectopic leaf blade along the leaf vein of leaves of treated *J. curcas* plants. Panel (h): Typical serrate leaf phenotype of plants silenced in AGO1 expression. Panels (i) and (j): Abnormal leaf shape in plants with silenced AGO1 expression. (k) adaxial (m) abaxial vector control leaves. Scale bar=10 mm.

FIG. 9B: Scanning electron micrograph of leaves with silenced AS1 expression. Note the adaxial ectopic leaf blade. PB: primary blade; EB: ectopic blade; ebad: ectopic blade adaxial; ebab: ectopic blade abaxial.

FIG. 9C: Transverse sections of ectopic blade showing differentiation of palisade tissue (ectopic blade palisade, ebp) and lateral vein (ectopic blade vein, ebv).

FIG. 9D: Scanning electron micrograph of leaves with silenced AGO1 expression. Note the abaxial ectopic leaf blade along the primary veins (V).

FIG. 9E: Transverse sections of leaf with silenced AGO1 expression. Note that the ectopic abaxial blade is contiguous with the lower epidermis (E) and the spongy parenchyma (sp).

FIG. 9F: Transverse sections of adaxial bubbles of leaf with silenced AGO1 expression. Note the mosaic composition of vascular-like structure (xylem, x; phloem, p) and two layers palisade parenchyma (pp).

FIG. 9G: Transverse sections of *J. curcas* leaves infected with empty vector control.

FIG. 9H: Real time RT-PCR analysis of expression levels of AS1 and class I KNOX gene (KNAT1-like) in *J. curcas* leaves with silenced AS1 expression.

FIG. 9I: Real time RT-PCR analysis of expression levels of AGO1 and iPHAVOLUTA (PHAV) in *J. curcas* leaves with silenced AGO1 expression. Scale bar=50 μm (C, E, F, G), 200 μm in B and D.

Figure 10:
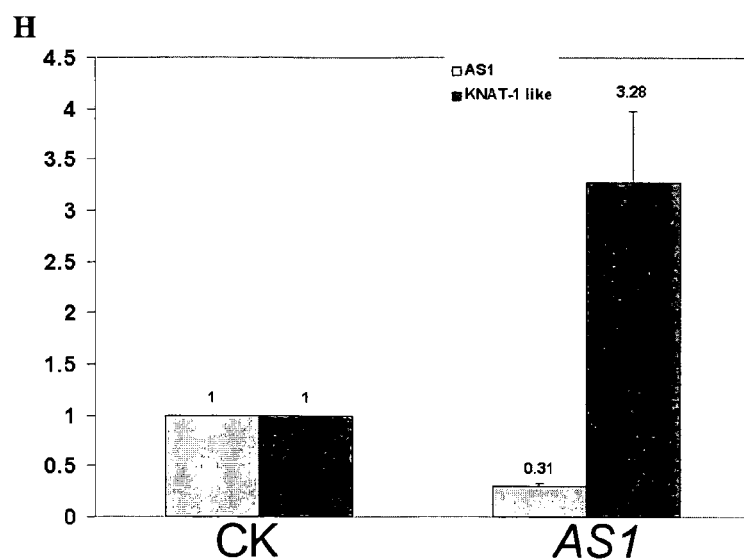
Figure 10:
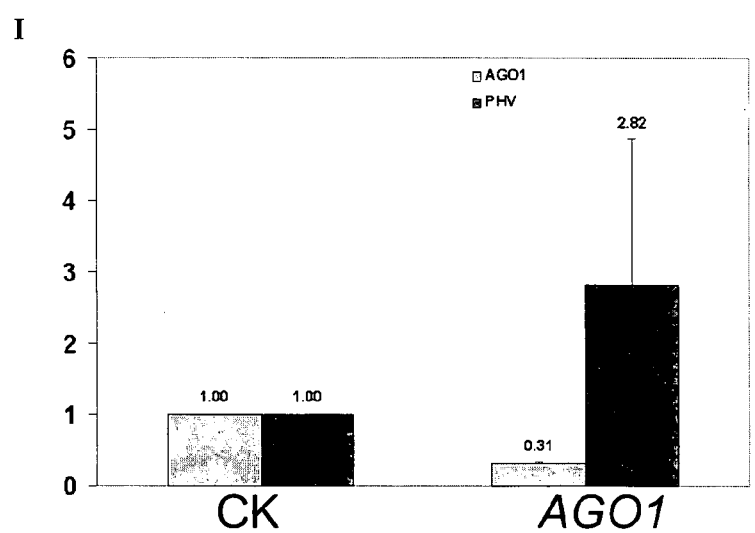
Figure 10:
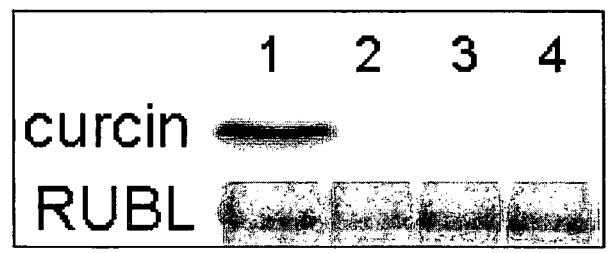

FIG. 10 shows silencing of the gene encoding curcin toxin protein in *J. curcas*. Western blot analysis of leaves of *J. curcas* with silenced curcin expression. Top panel: the curcin proteins were detected with anti-curcin antibody. Bottom panel: Coomassie Bright Blue staining of the RUBL (the large subunit of RUBISCO) which serves as a loading control. Lane 1: empty vector-infected plant leaves, lanes 2-4, TRV: curcin infected *J. curcas* leaves.

Figure 11:
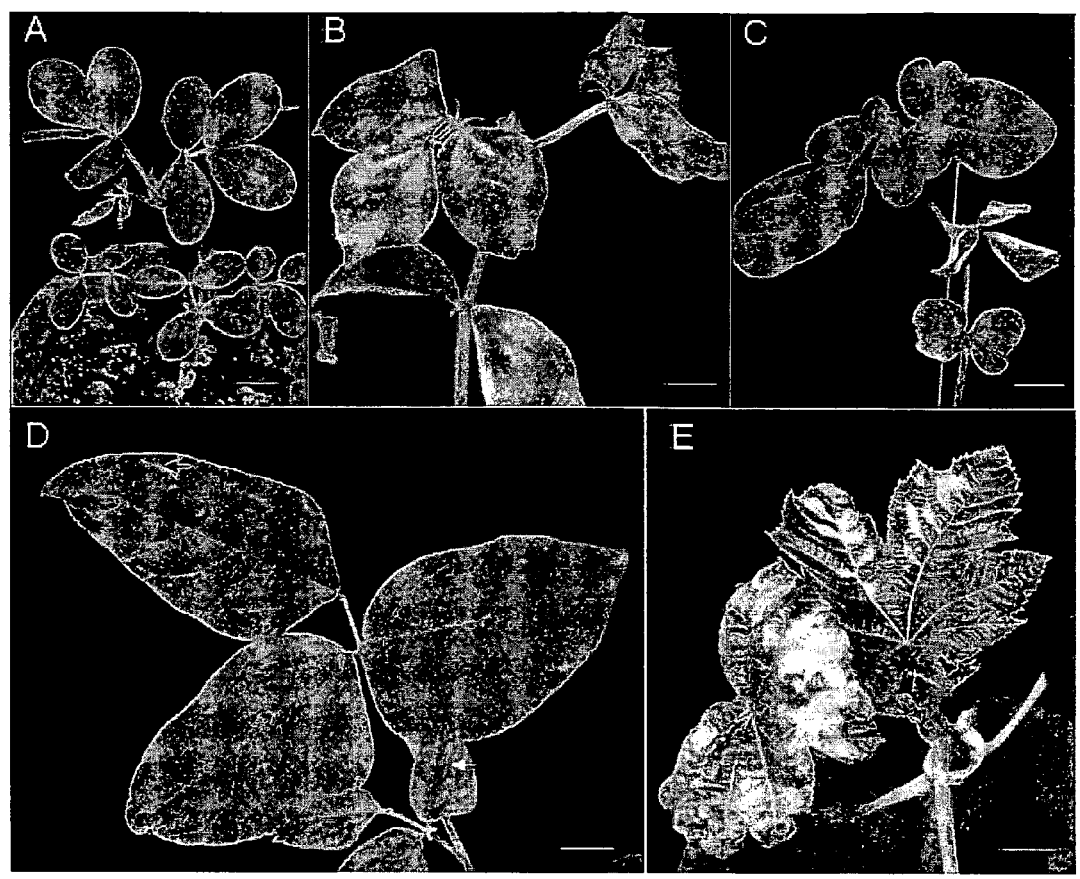

FIGS. 11A-11E show some putative host plants (Dinesh Kumar et al. (2007) for plants shown in FIGS. 11A. 11C, 11D and 11E) that have been treated with sTRV:JcCH42. FIG. 11A: *Arachis hypogaea*; FIG. 11B: *Phaseolus aureus*; FIG. 11C: *Glycine max*; FIG. 11D: *Phaseolus vulgaris*; FIG. 11E: *Ricinus communis*. Scale bar: 10 mm.

Figure 12:
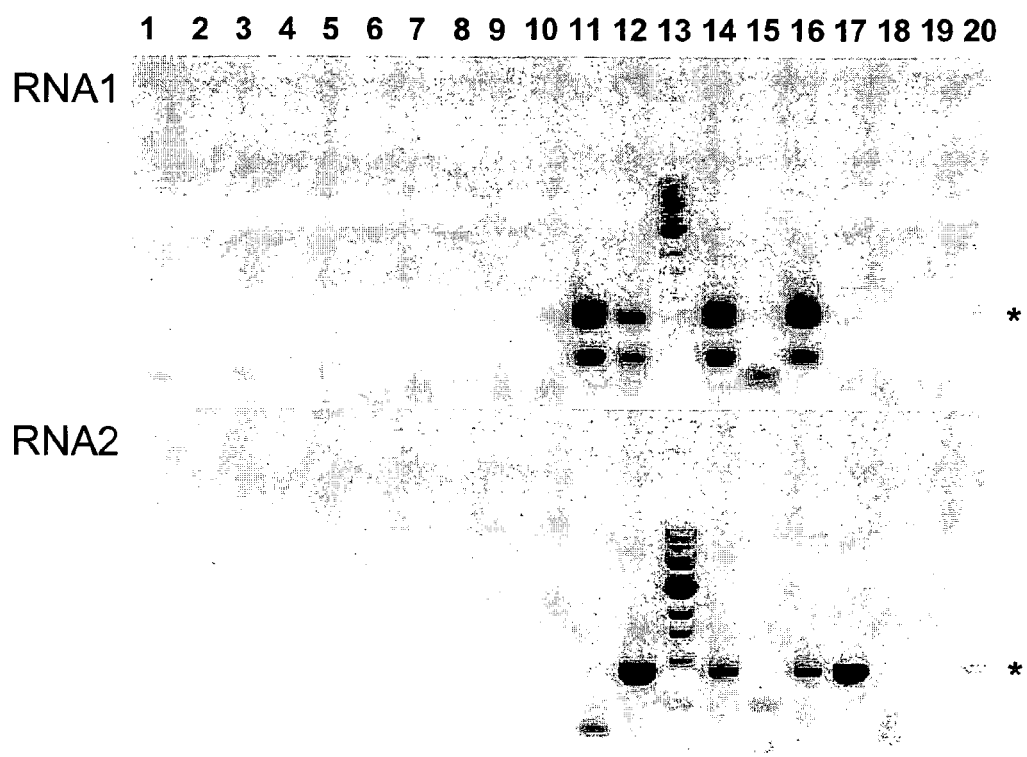

FIG. 12 shows TRV viral RNA analysis (RNA1 and RNA2) of some putative host plants (Dinesh Kumar et al. (2007) for plants for which data shown in lanes 1-5, 11, 12 and 14-17) that have been treated with sTRV:JcCH42 or mock control. Lanes 1-5: *Arachis hypogaea* (lanes 1-3, treated with sTRV: JcCH42, lanes 4 and 5 from mock control); lanes 6-10: *Phaseolus aureus* (lanes 6-8, treated with sTRV:JcCH42, lanes 9 and 10 from mock control); lanes 11-12 and 14-19: *Ricinus communis* (lanes 11-12 and 14-17, treated with sTRV:JcCH42, lanes 18 and 19 from mock control), lane 13 is 1 kb DNA ladder marker. "*" indicate proposed PCR amplified bands.

DETAILED DESCRIPTION OF THE INVENTION

The present invention relates to the field of functional analysis of *Jatropha* genes on a genomic scale. More specifically, the present invention relates to a method for high-throughput functional analysis of *Jatropha curcas* genes on a genomic scale using virus-induced gene silencing.

Virus-induced gene silencing (VIGS) (Ruiz et al., 1998; Burch-Smith et al., 2004) system offers the possibility to determine the biological function of gene products without the need to genetically transform the plant. Both RNA and DNA viruses induce RNA silencing resulting in the production of virus-related siRNAs (Baulcombe, 2004). Recombinant viruses can be constructed carrying an inserted partial sequence of a candidate plant gene. Such recombinant viruses can move systemically in whole plants producing siRNA which can mediate degradation of the endogenous candidate gene transcripts (Brigneti et al., 2004; Burch-Smith et al., 2004) resulting in silencing of the candidate gene expression in inoculated plants.

VIGS approach offers several opportunities:

(1) an efficient reverse genetics tool to gene/gene family knock-down;

(2) a rapid and high-throughout (Liu et al., 2002b)—whole genome ORF knock-out in less than one month;

(3) transient, reversible and so called "inducible" knock-out phenotype (Liu et al., 2002a); and (4) different organs suitable for silencing, offer a chance to knock-out genes in the roots (Valentine et al., 2004; Kaloshian, 2007), the flowers (Liu et al., 2004; Chen et al., 2005), the leaves (Liu et al., 2002a; Liu et al., 2002b; Burch-Smith et al., 2006), or the fruit (Fu et al., 2005), by different infected methods.

The TRV VIGS system has been successfully applied in some plants such as *Arabidopsis* (Burch-Smith et al., 2006), *Capsicum annuum* (Chung et al., 2004), *Lycopersicon esculentum* (Liu et al., 2002; Dinesh Kumar et al. 2007), *Petunia hybrida* (Chen et al., 2005), *Nicotiana benthamian* (Liu et al., 2002), *Solanum tuberosum* (Brigneti et al., 2004). Most of these plants have been experimentally proven to be susceptible hosts of some strain of TRV (Plant Virus Online, http colon backslash image dot fs dot uidaho dot edu backslash vide backslash descr808 dot htm). More importantly, this TRV VIGS system cannot reasonably be expected to inevitably work in all plants. For example, Dinesh Kumar et al. (2007) contains a list of plants for which it is stated that the TRV VIGS system may work. However, this TRV VIGS system cannot work in *Arachis hypogaea* and *Glycine max*, because they are not hosts to TRV despite their inclusion in the list in Dinesh Kumar et al. (2007). In fact, as demonstrated herein, the TRV VIGS system does not work in all plants listed as being susceptible to Tobacco Rattle Virus (TRV) in Dinesh Kumar et al. (2007) or in the online virus databases. Furthermore, systemic infection is required for the TRV VIGS system to be useful for functional gene analysis. Some plants may be susceptible to TRV locally but not systemically, and thus the TRV VIGS system will not work in those plants. Prior to the present invention, *Jatropha* was not known to be host to TRV or known to be susceptible in any degree to TRV either locally or systemically. The finding that *Jatropha* is susceptible to TRV and that the TRV VIGS system can be used in *Jatropha* was discovered after screening many viral vectors and thus was unexpected. The unexpected nature of the present invention is further evidenced by the inability of the TRV VIGS system to work in all plants which are susceptible to TRV or are listed as host plants for TRV.

In one aspect, the present invention provides an efficient and reproducible system and procedure for VIGS in *J. curcas*. In one embodiment, the present invention provides for the co-silencing of DCL4 to enhance the VIGS efficiency. In another embodiment, the present invention provides for the further re-synthesis of the whole TRV viral genomes. In an additional embodiment, the present invention demonstrates that these vectors have similar efficiency as the original vectors. In a further embodiment, the present invention provides for the use of TRV VIGS system for cloning and functionally identifying several important fatty acid biogenesis pathway genes. These important genes can be used to improve fuel properties of biodiesel such as cold-temperature flow characteristics, oxidative stability and NOx emissions.

Thus in a first aspect, the present invention provides a method of virus-induced gene silencing (VIGS) in *Jatropha*. In accordance with the present invention, the method comprises:

(a) inserting a nucleic acid comprising a sequence of a first desired gene to be silenced into a vector comprising a tobacco rattle virus (TRV) RNA2 sequence to produce a modified TRV RNA2 vector;

(b) preparing a mixed culture of *Agrobacterium* comprising *Agrobacterium* containing a vector comprising a TRV RNA1 sequence and *Agrobacterium* containing the modified TRV RNA2 vector;

(c) introducing the mixed culture of *Agrobacterium* into plant tissue of *Jatropha* by vacuum infiltration to produce infected plants; and (d) growing the infected plants for a sufficient time to induce gene silencing of the desired gene.

In one embodiment, the vector comprising TRV RNA2 and the vector comprising TRV RNA1 are synthetic plant vectors. The results and the phenotypic data shown herein indicate that the synthetic STRV-VIGS systems can be used as effectively as TRV-VIGS systems to induce silencing of desirable endogenous *J. curcas* genes. In another embodiment, the sequence of the first desired gene is the sequence of a sense strand of the gene. In an additional embodiment, the sequence of the first desired gene is the sequence of an antisense strand of the gene. As shown herein, the VIGS system of the present invention can be used to rapidly characterize individual members of a multiple gene family which may share overlapping functions. In a further embodiment, the nucleic acid further comprises a sequence of a second desired gene to be silenced. In one embodiment, the second desired gene is virus resistance gene. In another embodiment, the virus resistance gene is selected from the group consisting of RNase III Dicer-like 4 (DCL4) gene, RNase III Dicer-like 2 (DCL2) gene, RNase III Dicer-like 3 (DCL3) gene, ARGONAUTE1 (AGO1), ARGONAUTE71 (AGO7), RNA-dependent RNA polymerase 1 (RDR1), RNA-dependent RNA polymerase 6 (RDR6), Suppressor of gene silencing 1 (SGS1), Suppressor of gene silencing 3 (SGS3), and Silencing defective 3 (SDE3). The phenotypic and molecular analyses shown herein demonstrate that co-silencing virus resistance genes can confer a higher VIGS efficiency in treated *J. curcas* plants. Furthermore, co-silencing of the viral-resistant system also can be used to increase the efficiency of other VIGS systems in other plant species. In a further embodiment, the nucleic acid comprises sequences of more than two desired genes to be silenced. The data shown herein indicate that VIGS system of the present invention can be used to knock down the expression of two or more genes thus allowing the deciphering of gene function in the event of functional redundancy.

In some embodiments, the desired gene is a candidate gene in fatty acid biosynthesis, such as a β-ketoacyl-acyl carrier protein synthase II (KASII) gene, an acyl-acyl carrier protein thioesterase B (FATB) gene, a stearoyl-acyl carrier protein desaturase (SAD) gene, and a fatty acid desaturase (FAD) gene. In other embodiments, the desired gene is a candidate transcription factor gene. In one embodiment, the desired gene is a candidate gene in smRNA biosynthesis. In another embodiment, the desired gene is a candidate gene in biosynthesis of toxic agents. The results shown herein demonstrate that the VIGS system of the present invention can efficiently suppress targeted host genes and can be used as a rapid means to assay the role of candidate genes in fatty acid biosynthesis or in the biosynthesis of toxic genes, as well as to study the role of regulatory genes, such a transcription factor genes or the role of genes involved in the small RNA biogenesis pathways. As shown herein, seed suppression of SAD1 gene can be used to produce *Jatropha* oil containing a high stearic acid content. As further shown herein, seed suppression of FAD2-1 gene and FAD-2 gene can be used to produce *Jatropha* oil containing higher oleic acid content with lower 16-carbon fatty acid content.

The results and the phenotypes data shown herein indicate that the VIGS system can be successfully used to induce silencing of other desirable endogenous *J. curcas* genes. We have generated expressed sequence tags (EST) for several different *Jatropha* tissues such as seeds and flowers. These expressed sequence tags (ESTs) provide a wealth of information for functional genomics study of *Jatropha*. Therefore, the VIGS assay described herein offers a means to test the function of *Jatropha* gene sequences in a homologous system. Using a normalized cDNA library it is possible to conduct large scale screens of gene function with the VIGS system of the present invention.

In a second aspect, the present invention provides a method of analyzing gene function in *Jatropha*. In accordance with the present invention, the method comprises:

(a) inserting a nucleic acid comprising a sequence of a candidate gene to be silenced into a vector comprising a tobacco rattle virus (TRV) RNA2 sequence to produce a modified TRV RNA2 vector;

(b) preparing a mixed culture of *Agrobacterium* comprising *Agrobacterium* containing a vector comprising a TRV RNA1 sequence and *Agrobacterium* containing the modified TRV RNA2 vector;

(c) introducing the mixed culture of *Agrobacterium* into plant tissue of *Jatropha* by vacuum infiltration to produce infected plants;

(d) growing the infected plants for a sufficient time to induce gene silencing of the candidate gene; and analyzing the phenotypic effect of the silenced candidate gene on the infected plant.

In one embodiment, the vector comprising TRV RNA2 and the vector comprising TRV RNA1 are synthetic plant vectors. In another embodiment, the sequence of the first desired gene is the sequence of a sense strand of the gene. In an additional embodiment, the sequence of the first desired gene is the sequence of an antisense strand of the gene. In a further embodiment, the nucleic acid further comprises a sequence of a second desired gene to be silenced. In one embodiment, the second desired gene is virus resistance gene. In another embodiment, the virus resistance gene is selected from the group consisting of RNase III Dicer-like 4 (DCL4) gene, RNase III Dicer-like 2 (DCL2) gene, RNase III Dicer-like 3 (DCL3) gene, ARGONAUTE1 (AGO1), ARGONAUTE71 (AGO7), RNA-dependent RNA polymerase 1 (RDR1), RNA-dependent RNA polymerase 6 (RDR6), Suppressor of gene silencing 1 (SGS1), Suppressor of gene silencing 3 (SGS3), and Silencing defective 3 (SDE3). In a further embodiment, the nucleic acid comprises sequences of more than two desired genes to be silenced.

In some embodiments, the desired gene is a candidate gene in fatty acid biosynthesis, such as a β-ketoacyl-acyl carrier protein synthase II (KASII) gene, an acyl-acyl carrier protein thioesterase B (FATB) gene, a stearoyl-acyl carrier protein desaturase (SAD) gene, and a fatty acid desaturase (FAD) gene. In other embodiments, the desired gene is a candidate transcription factor gene. In one embodiment, the desired gene is a candidate gene in smRNA biosynthesis. In another embodiment, the desired gene is a candidate gene in biosynthesis of toxic agents.

Once the function of a *Jatropha* gene or *Jatropha* genes has been characterized, transgenic plants can be prepared using conventional techniques to alter expression patterns of the gene or genes.

The DNA that is inserted (the DNA of interest) into plants of the genera *Jatropha* is not critical to the transformation process. Generally the DNA that is introduced into a plant is part of a construct. The DNA may be a gene of interest, e.g., a coding sequence for a protein, or it may be a sequence that is capable of regulating expression of a gene, such as an antisense sequence, a sense suppression sequence or a microRNA (miRNA) sequence. The construct typically includes regulatory regions operatively linked to the 5' side of the DNA of interest and/or to the 3' side of the DNA of interest. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670 and 2006/0248616. The expression cassette may additionally contain selectable marker genes. See, U.S. Pat. No. 7,205,453 and U.S. Patent Application Publication Nos. 2006/0218670 and 2006/0248616.

Generally, the expression cassette will comprise a selectable marker gene for the selection of transformed cells.

Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, WO 02/36782, U.S. Pat. No. 7,205,453 and U.S. Patent Application Publication Nos. 2006/0248616 and 2007/0143880, and those references cited therein. This list of selectable marker genes is not meant to be limiting. Any selectable marker gene can be used.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV$^{35S}$ promoter (Odell et al., 1985); rice actin (McElroy et al., 1990); ubiquitin (Christensen and Quail, 1989 and Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569.597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters are described in U.S. Pat. Nos. 6,506, 962, 6,575,814, 6,972,349 and 7,301,069 and in U.S. Patent Application Publication Nos. 2007/0061917 and 2007/0143880.

Where appropriate, the DNA of interest may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols* (*Methods in Molecular Biology*), Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Experimental Procedures

*J. curcas* seedlings: *J. curcas* seeds purchased from India were germinated in a greenhouse. *J. curcas* seedlings after 10-14 days post germination were used for VIGS assays. At this stage, seedlings have 2-3 true leaves.

Original TRV vectors: pTRV1 (GenBank No. AF406990) and pTRV2 (GenBank No. AF406991) were kindly given by Dr. Dinesh Kumar (Yale University).

Synthetic TRV RNA1 expression vector: Synthetic TRV1 vector full length (7756 bp) sequence including: SphI site, T-DNA right border sequence (152 bp), the duplicated cauliflower mosaic virus (CaMV) 35S enhancer region (752 bp) (Shi et al., 1997) the TRV Ppk20 strain RNA1 (6791 bp), Subterranean Clover Mottle Virus satellite RNA ribozyme sequence (46 bp) and SmaI site sequence. This full length sequence was divided into two parts by an endogenous SalI site. The two parts were separately synthesized and cloned into pGH vector to give two vectors pGH-YeJ-V1-1 and pGH-YeJ-V1-2. The synthetic TRV RNA1 fragments, V1-1, released from pGH-YeJ-V1-1 by treatment with SphI and SalI enzymes, and V1-2, released from pGH-YeJ-V1-2 by treatment with SalI and SmaI enzymes, were linked with the pBIN 121 vector treated with SphI and EcoICRI enzymes. The new synthetic TRV RNA1 vector was named psTRV1001. The sequence of the synthetic psTRV1001 is set forth in SEQ ID NO:1. The synthetic TRV RNA1 sequence is the same as the published TRV RNA1 sequence.

Synthetic TRV RNA2 expression vector: Synthetic TRV2 vector full length (2915 bp) sequence including: HindIII site, the duplicated cauliflower mosaic virus (CaMV) 35S enhancer region (752 bp) (Shi et al., 1997) the TRV strain ppk20 RNA2 5'-sequence (1639 bp), multiple cloning site (61 bp), the TRV strain ppk20 RNA2 3'-sequence (396 bp), HpaI site. The full length sequence was synthesized and cloned into pGH vector give pGH-YeJ-V2. The synthetic TRV RNA2 fragment V2 was linked into the pCAMBIA0390 by HindIII and HpaI sites. The new synthetic TRV RNA2 vector was named psTRV2001. The sequence of the synthetic sTRV2 is set forth in SEQ ID NO:2. The synthetic TRV RNA2 sequence is the same as the published TRV RNA2 sequence.

Gene cloning and VIGS vector cloning: Most of the gene sequences were obtained from the GenBank and a sequence data base of cDNA library prepared from *J. curcas* seeds. CH42, PDS, PCNA, AS1 and DCL4 genes were cloned by PCR using designed primers of conserved regions shared by homologous gene sequences of other Euphorbiaceae plants such as castor bean and cassava. For single gene VIGS, all candidate genes were amplified by PCR from cDNA products of *J. curcas* seeds, roots, flower and leaves samples, and cloned into the original TRV vectors pTRV2 or the XbaI and BamHI sites of the synthetic vector psTRV2001. For co-silencing vectors, cDNA fragment of the second gene was inserted into BamHI and KpnI sites of the vector. The primers used in cloning the genes are set forth in Table 1, which also includes reference to the sequence of the cloned gene.

TABLE 1

Gene Primers and Gene Sequences

| Gene | Primers | SEQ ID NO: | Cloned Gene |
|---|---|---|---|
| KASII | 5' ccttgtgtggatccagttttcaagg | 3 | GenBank: DQ987700 |
|  | 3' ttatctagactgcatgccacaaaacctcc | 4 | 829 bp |
| PCNA | 5' tctagaccatggattccagccacgttgc | 5 | T-easy vector, then XbaI and BamHI SEQ ID NO: 7 |
|  | 3' ggatccctcagcaatcttgtactcaacc | 6 | 614 bp |
| PDS-shorter | 5' cccggggcmatgtcaaaggcdknaaktt | 8 | T-easy vector |
|  | 3' ggatcctcaaaccatatmtgvacmttwat | 9 | 302 bp |
| PDS-longer | 5' aattctctagaggccagagaaagtaagtttgcaattgg | 10 | SEQ ID NO: 12 |
|  | 3' tgaattggatcctctgatcagcagatatttcatcaggaaa | 11 | 786 bp |
| CH42-shorter | 5' tctagagaagarggrgagctccggccccagc | 13 | T-eacy vector |
|  | 3' ggatccaatttctcaatgacaagcaaacc | 14 | 446 bp |
| CH42-longer | 5' aatccatctagaagagagggcaatttc-tatttccacccggcacg | 15 | SEQ ID NO: 17 |
|  | 3' aatatagatctattcattctcttcaatttagtac | 16 | 696 bp |
| Curcin | 5' gcgtctagaggaaagatgaggatattacaggg | 18 | GenBank AY069946 |
|  | 3' taaagatctaagagaagcatttggc | 19 | 836 bp |
| FAD2-1 | 5' aactttctagaccaccattcacacttggtcag | 20 | GenBank DQ157776 |
|  | 3' ttattggatcccatgagtgtctgtaatgttatg | 21 | 862 bp |
| FAD2-2 | 5' aactttctagacgactcactatagggcga | 22 | SEQ ID NO: 24 |
|  | 3' ttattggatcccaagttgtagagttccat | 23 | 711 bp |
| FAD6 | 5' aactttctagaaccatcttcagacagtgc | 25 | GenBank EU106889 |
|  | 3' ttattggatccagggtagtcacaatgaac | 26 | 835 bp |
| FATB | 5' tggatccacagtaggctata | 27 | GenBank EU106891 |
|  | 3' aattggtaccagccaatgtacttcacattg | 28 | 796 bp |
| SAD1 | 5' atctctagatgaatgggctgag | 29 | GenBank DQ08449 |
|  | 3' tgtttagatctacaaacgtaatcctgagc | 30 | 862 bp |
| SAD2 | 5' aatatctagacgccacctctattgaagc | 31 | SEQ ID NO: 33 |
|  | 3' atatggatcctactccaagccgctgagc | 32 | 821 bp |
| SAD3 | 5' tataatctagaccacagcctgagtctgaa | 34 | SEQ ID NO: 36 |
|  | 3' tgattggatccgatgttgctttcttgactc | 35 | 847 bp |
| AGO1 | 5' ttatttctagacttgcacaaatgtgtcat | 37 | SEQ ID NO: 39 |
|  | 3' tagaaggatccaggaagtatattcccac | 38 | 854 bp |

TABLE 1-continued

Gene Primers and Gene Sequences

| Gene | Primers | | SEQ ID NO: | Cloned Gene |
|---|---|---|---|---|
| AS1 | 5' | acatattctagattgaggagagatgctgaagcaaa | 40 | SEQ ID NO: 42 |
|  | 3' | tggatggatccgcttcagcatctctcctcaa | 41 | 629 bp |
| DCL4 | 5' | aataactctagacaggtatatatacgtgatcaaccattt | 43 | T-easy vector cloning SEQ ID NO: 45 |
|  | 3' | tttatggatccatacctgatagcagcctcctcc | 44 | 678 bp |
| DCL4 co-silencing | 5' | aataaggtaccatacctgatagcagcctcc | 46 | |
|  | 3' | gtagtgagtgcttctaatactcgagaataa | 47 | |

Agrobacterium infiltration: pTRV 1, pTRV2, synthetic psTRV vectors and its derivatives were introduced into *Agrobacterium* strain AGL1 by electroporation. A 3 ml culture was grown for 24 hr at 28° C. in 50 mg/L kanamycin and 25 mg/L rifampicin. On the following day, the culture was inoculated into LB medium containing 50 mg/L kanamycin, 10 mM 2-(N-morpholino)ethanesulfonic acid (MES) and 20 µM acetosyringone and grown overnight in a 28° C. shaker. *Agrobacterial* cells were collected by centrifugation and resuspended in MMA solution (10 mM MES, 10 mM $MgCl_2$, 200 µM acetosyringone) to a final $OD_{600}$ of 1.5. The agrobacterial suspension was left at room temperature for 3-4 hr without shaking. Before infiltration, *Agrobacterium* cultures containing the pTRV1/psTRV1 or pTRV2/psTRV2 vectors were mixed in a 1:1 ratio. *Jatropha* plants were infiltrated with cultures either by syringe infiltration or by vacuum infiltration. For syringe infiltration, agrobacterial-inocula were delivered into the underside of two or three youngest fully-expanded leaf using a 1 ml needleless syringe. For vacuum infiltration, whole plants were submerged into agrobacterial-inocula and subjected to 80–90 kPa vacuum for 5 min, and then quickly releasing the vacuum, letting the inoculum rapidly enter plant tissues. After infiltration, excess agrobacterial cell suspension was used to drench the root system of infiltrated plants. Infiltrated plants were grown in a growth chamber at 25° C. with 16 hr light/8 hr dark photoperiod cycle. The same method was also used in experiments testing VIGS in putative host plants.

Gas chromatography: 100-200 mg fresh *Jatropha* leaf samples were homogenized in liquid nitrogen, and 1 ml of 2:1 chloroform:methanol (v/v) was added to samples. Tripentadecanoin (50 µg; SIGMA) was added to the mixture as an internal standard. Plant tissue was further broken with MIXER MILL MM300 (Retsch, Germany) then frozen in liquid nitrogen again. After thawing, the suspension was centrifuged at 12,000 g for 10 min. The pellet was discarded and 0.3 ml of 1% KCl (w/w) was added to the supernatant and mixed. After centrifugation, the bottom phase was transferred into a new tube and the content concentrated in Concentrator 5301 (Eppendorf, Germany). The lipid extract was re-extracted three times by 1 ml of hexane each and centrifuged to discard the pellet. Lipids were transmethylated to fatty acid methyl esters by incubation with an equal volume 3N methanolic-HCL (SIGMA) plus 400 µL 2,2-dimethoxypropane (2,2,DMP, SIGMA) and kept at 70° C. in a water bath for 10 min. The samples were cooled at 4° C. for 10 min, and 1 ml water and 1 ml hexane were added and the content mixed vigorously. The upper ester layer was collected and concentrated or analysis by GC using Agilent 6890 (Palo Alto, Calif., USA) employing two 7 m×0.53-mm Supelcowax columns (SPB50, Supelco, Bellefonte, Pa., USA) and using helium as the carrier gas. The GC analytical method was 140° C. for 50 sec, 30° C. $min^{-1}$ ramp to 240° C., and the final temperature was maintained for 50 sec for a total run time of 32 min.

Scanning Electron Microscope (SEM): SEM (JSM-6360LV, JEOL, USA) was used to observe fresh *J. curcas* leaf samples. Fresh leaves were detached and fixed with tape inside the sample chamber, following freezing in liquid N2.

Light microscopy: Leaf discs were excised from silenced *J. curcas* leaves and fixed overnight in 2.5% glutaraldehyde in 0.1 M phosphate buffer, pH 7.2. Leaf discs were rinsed three times in 0.1 M phosphate buffer for 15 min each, and were then post-fixed in 1% (w/v) aqueous $OsO_4$ for 1 hr. Tissues were dehydrated in an ethanol series and embedded in Spurr's resin. Semi-thin sections 500 nm thick were stained in 0.1% toluidine blue and photographed with a Zeiss Axiophot microscope (Carl Zeiss, Germany).

RNA extraction and analysis: 100 mg leaf tissue was ground in liquid N2 and extracted with plant RNA purification reagent (Invitrogen) or Trizol (Invitrogen). RNA concentration was measured by Nanodrop (Thermo, USA). DNase treatment and reverse transcription (RT) reaction were performed as described (Qu et al., 2007). For TRV RNA1 analysis, first strand cDNA synthesis reaction was performed with TRV1-P3 primer (5'-TTAAGACGAGTTTTTCTTATTA-GACGCTCTCT-3'; SEQ ID NO:82), followed by full-length movement protein gene (MP, length in 756 nt) PCR amplification with TRV1-P5 (5'-ATGGAAGACAAGTCATTGGT-CACCTTGAAGAA-3'; SEQ ID NO:83) and TRV1-P3 primers. For TRV RNA2 analysis, first strand cDNA synthesis reaction was performed with TRV2-P3 primer (5'-GAT-CAATCAAGATCAGTCGAGAATG-3'; SEQ ID:NO:84), followed by further PCR amplification with TRV2-P5 (5'-GATGGACATTGTTACTCAAGGAAGC-3'; SEQ ID NO:85) and TRV2-P3 primers. Theoretical PCR amplified TRV RNA2 band should be 939 bps (including the inserted partial JcCH42 gene). Real-time PCR was performed with Power SYBR® Green PCR Master (Applied Biosystems, USA) and run in ABI7900HT. All samples were run in triplicates and data was analyzed with RQ manager at a pre-set Ct value (Applied Biosystems, USA). The *J. curcas* rbcL mRNA served as an internal control. The real-time PCR primer sequences are set forth in Table 2.

TABLE 2

Real-Time PCR Primers

| Primer | Sequence (5'-3') | SEQ ID NO: |
|---|---|---|
| CH42-F | CTGTGCAGATAGATCATG | 48 |
| CH42-R | ATGACAGTAGCAACATCC | 49 |
| FAD6-F | TGGTGCATCATACGGCTC | 50 |
| FAD6-R | ATGTGAACATTGATATCATG | 51 |
| AGO1-F | GGCAAGGAGCTTGACCTGC | 52 |
| AGO1-R | TCAGCGCTACATTGGCTAG | 53 |
| AS1-F | AGAGCTGAAGAGGACGCC | 54 |
| AS1-R | CAGGCTTGAGGTAGTTCTTC | 55 |
| DCL4-F | GCCAGTCAAGTCAGATGC | 56 |
| DCL4-R | CCACACTGATGCCCAGCC | 57 |
| FATB-F | TGTGGATGAGGATGGCAG | 58 |
| FATB-R | CCAGCCAATGTACTTCAC | 59 |
| SAD1-F | CAGCTGTTGCACAGCGGC | 60 |
| SAD1-R | GGAGGTAGCCGACAAACG | 61 |
| SAD2-F | GTGGACTGGGCCTGGACT | 62 |
| SAD2-R | TCTGATCCTGGGTCCATG | 63 |
| SAD3-F | TTCGTTCCAGGAGAGAGC | 64 |
| SAD3-R | TCGACCTCAAATAACTTCTC | 65 |
| KNOT1-F | GGTTTGGACCAGAAACAAATAAAT | 66 |
| KNOT1-R | CACCCATGTAGTGACCATCC | 67 |
| PHV-F | GGGTGGTGGTTCAATCATTC | 68 |
| PHV-R | TCTCCGCTAGTCTCTTGTGC | 69 |
| KASII-F | CCTTGTGTGGATCCAGTTTTCAAGG | 70 |
| KASII-R | GCTTCTCCAGAAAGAGCGAGCCGA | 71 |
| PCNA-R | CAACAGTAGACAAGCCTGAAGAGG | 72 |
| PCNA-F | GCAATCTTGTACTCAACCACAACAG | 73 |
| PDS-R | CTCCTGAAGAAATCGGTTCAGTG | 74 |
| PDS-F | TGACCGTTCAAGAATGGATGAG | 75 |
| RUBL-R | CTTCTCCAGCAACGGGCTC | 76 |
| RUBL-F | GGAGTTCCGCCTGAGGAAG | 77 |
| FAD2-1-R | GGTTGAGGAAGGAGGTGGAAG | 78 |
| FAD2-1-F | CCACCATTCACACTTGGTCAG | 79 |
| FAD2-2-F | AGCAATCAAGCCTATATTGGGC | 80 |
| FAD2-2-R | CCAGAGAACTCCTCGGTTGG | 81 |

Antibodies and protein gel blot analysis: Curcin protein antibody was prepared by Dr. Yin zhongcao's lab. Total plant proteins were separated by 12% sodium dodecyl sulfate-polyacrylamide gel electrophoresis. ECL peroxidase conjugated donkey anti-rabbit immunoglobulin G was used as a secondary antibody. Immunoreactive bands were visualized using ECL Western blotting Detection Reagents (GE healthcare). Coomassie blue-stained rbcL band was used as a loading control.

Example 2

Development of a VIGS System in *J. curcas* Using CH42 as a Marker Gene

This example describes the construction of a tobacco rattle virus (TRV) based vector and its use for gene silencing in *J. curcas*. Virus induce gene silencing (VIGS) is initiated when a recombinant virus carrying a sequence from a host gene infects the plant. The endogenous gene transcripts with sequence homology to the insert in the VIGS vector are degraded by a post-transcriptional gene silencing mechanism (PTGS) (Baulcombe. 2004).

Initially, TRV vectors kindly provided by Dr. Dinesh Kumar (Yale University) were used in this study. TRV is a bipartite positive sense RNA virus. TRV RNA1 encodes 134 kDa and 194 kDa replicase proteins from the genomic RNA, a 29-kDa movement protein and 16-kDa cysteine-rich protein from subgenomic RNAs. TRV RNA2 encodes the coat protein from the genomic RNA and two non-structural proteins from the subgenomic RNAs. TRV RNA1 can replicate and move systemically without RNA2. In the TRV RNA2 cDNA construct, the non-structural genes were replaced with a multiple cloning site (MCS) useful for cloning the target gene sequences for VIGS (MacFarlane et al., 1999).

We assessed the gene silencing efficiency of the TRV-VIGS clones to suppress CH42 gene expression in *J. curcas*. The enzyme encoded by the CH42 gene is responsible for adding magnesium into the porphyrin ring during chlorophyll biosynthesis. When this gene is silenced chlorophyll synthesis is blocked and consequently leaves lose their green color but appear yellow instead owing to the presence of carotenoids.

To amplify the CH42 homolog from *J. curcas*, PCR primers were designed targeting the conserved sequence motifs of CH42 from different species of the Euphorbiaceae family. First, we obtained a 440-bp CH42 cDNA of *J. curcas* by PCR, and the identity of this clone was verified by sequencing. This CH42 fragment was inserted into the TRV2 MCS site to give pTRV2-CH42S. We used this short CH42 sequence as a seed to find longer EST sequences of different Euphorbiaceae family CH42 genes in GenBank by BLASTN. We then further designed PCR primers to clone a 689-bp fragment of the *J. curcas* CH42 cDNA to give pTRV2-CH42L. The sequence of CH42L was also verified by sequencing.

Figure 1:
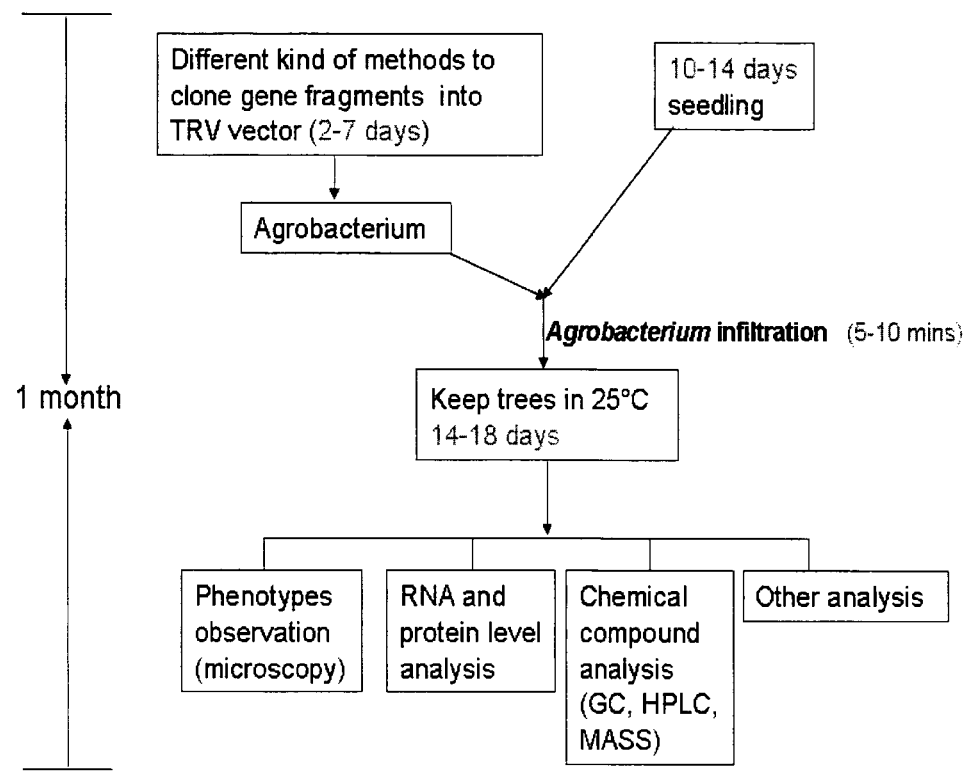
FIG. 1 illustrates a method for *J. curcas* virus-induced gene silencing (VIGS) in accordance with the present invention.
Figure 2:
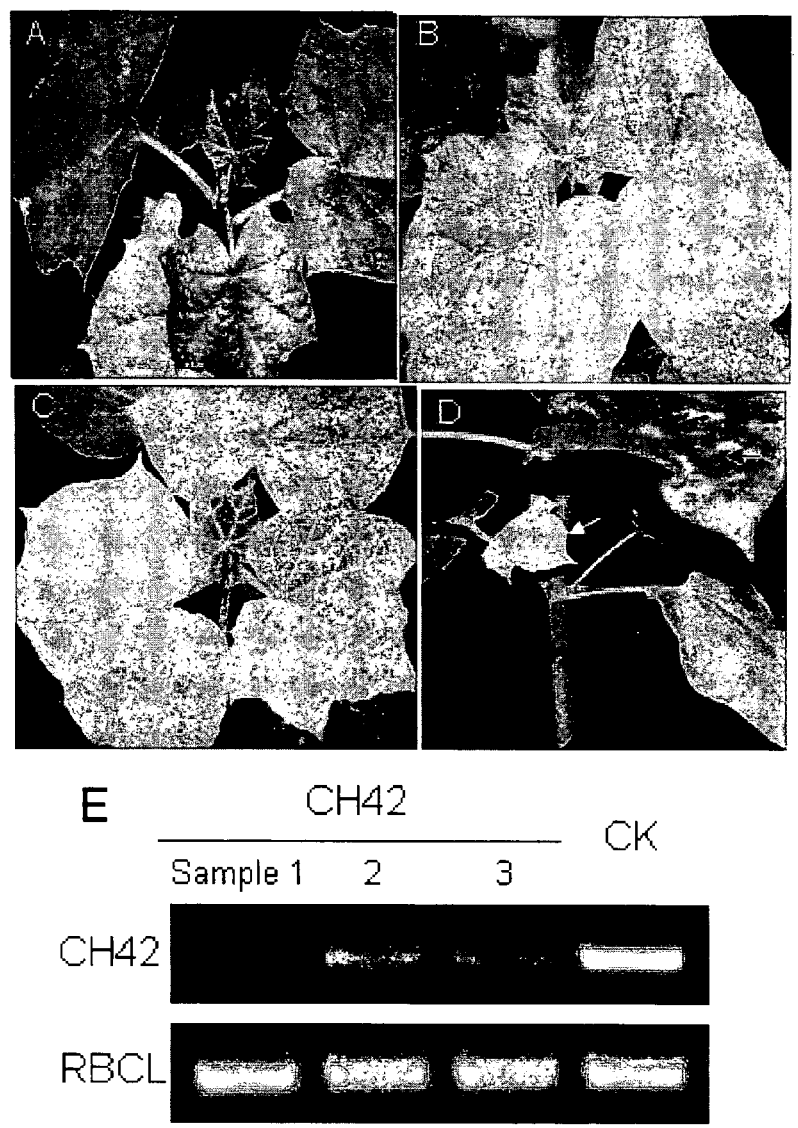
FIGS. 2A-2E show the VIGS effect on CH42 gene and the insert length effect of the CH42 gene. Cultures of *Agrobacterium tumefaciens* strains carrying pTRV1 or pTRV2 (Vector in FIG. 2A, TRV2-CH42-440 in FIG. 2B and TRV2-CH42-680 in FIG. 2C) were mixed in 1:1 ratio. Mixed culture was injected into *Jatropha* plants at 2-3 leaf stage plants using a 1 ml needle-less syringe. The CH42 enzyme is responsible for adding Mg into the porphyrin ring during chlorophyll biosynthesis. Silencing of the CH42 gene blocked chlorophyll synthesis in newly emerging leaves which lost their green color but appeared yellow owing to the presence of carotenoids. Note that the inoculated leaves still remained green because of the stability of pre-formed chlorophyll. TRV2-CH42S and TRV2-CH42L contained inserts of CH42 gene fragment of 440 bp and 689 bp, respectively.

Cultures of *Agrobacterium* carrying pTRV1 was mixed with cultures of *Agrobacterium* carrying either pTRV2-CH42S or pTRV2-CH42L. The mixed culture was injected onto *J. curcas* plants with 2-3 true leaves (for details see Example 1). Three to four days post injection, upper leaves of the treated plants were examined for silencing effects. We observed that the gene silencing effect persisted indefinitely in 3-5 leaves younger than the injected leaves (FIGS. 2B and 2C). TRV-CH42L which contained a CH42 insertion, induced a better silencing effect than the shorter one, TRV-CH42S (compare FIG. 2B with FIG. 2C). Moreover, the CH42L suppression effect was visible uniformly throughout the entire leaf (FIGS. 2B and 2C). Uniform silencing of target gene is helpful for high-throughout study and rapid analysis using VIGS since it allows easy sampling and collection of reproducible data. We performed RT-PCR, using total RNA extracted from plants treated with different TRV vectors to confirm the VIGS of the CH42 gene at the molecular and the results are shown in FIG. 2E. *J. curcas* CH42 RNA accumulation in the upper leaves of TRV-CH42L infected plant (lane 3) was much lower than that of plants infected with the empty TRV vector (lane 1) and lower than that of plants infected with TRV-CH42-S (lane 2) and of plants infected with the non-related vector control TRV-JcKASII (lane 4).

We further synthesized full-length TRV1 and TRV2 cDNA sequences and cloned into plant expression vectors to give psTRV1001 and psTRV2001. The CH42L gene fragment was inserted into psTRV2001 to generate psTRV2002. Mixture cultures of *Agrobacteria* cells containing pTRV1 and pTRV2-CH42L or psTRV1001 and psTRV2002 was agro-injected onto *J. curcas* plants with 2-3 true leaf. Four to 5 days post agro-injection, we observed similar silencing effects on plant leaves which turned yellowish (compare FIG. 3A with FIG. 3B).

These results and the phenotypic data indicated that the synthetic sTRV-VIGS systems could be used to induce silencing of desirable endogenous *J. curcas* genes. The data of the CH42 gene demonstrates that the same silencing efficiency is achieved with the synthetic vectors as with the original vectors.

Example 3

Optimization of the VIGS System by Vacuum Infiltration

After the CH42 gene, we next chose to silence another marker gene *phytoene desaturase* (PDS) which encodes a key enzyme involved in carotenoid biosynthesis. Silencing of the PDS gene would inhibit carotenoid biosynthesis leading to chlorophyll photooxidation and destruction at high light intensity and resulting in photo-bleached leaves.

To amplify the PDS homolog from *J. curcas*, PCR primers were designed to target conserved sequences of PDS from different species of the Euphorbiaceae family. First, we obtained a 302-bp PDS cDNA of *J. curcas* by PCR and inserted this fragment into pTRV2 to give pTRV2-PDSS. This short PDS sequence was used as a seed to find longer EST sequences of different Euphorbiaceae family PDS genes in GenBank by BLASTN. We further designed PCR primers to clone a 786-bp fragment of the *J. curcas* PDS cDNA to generate pTRV2-PDSL.

Figure 4:
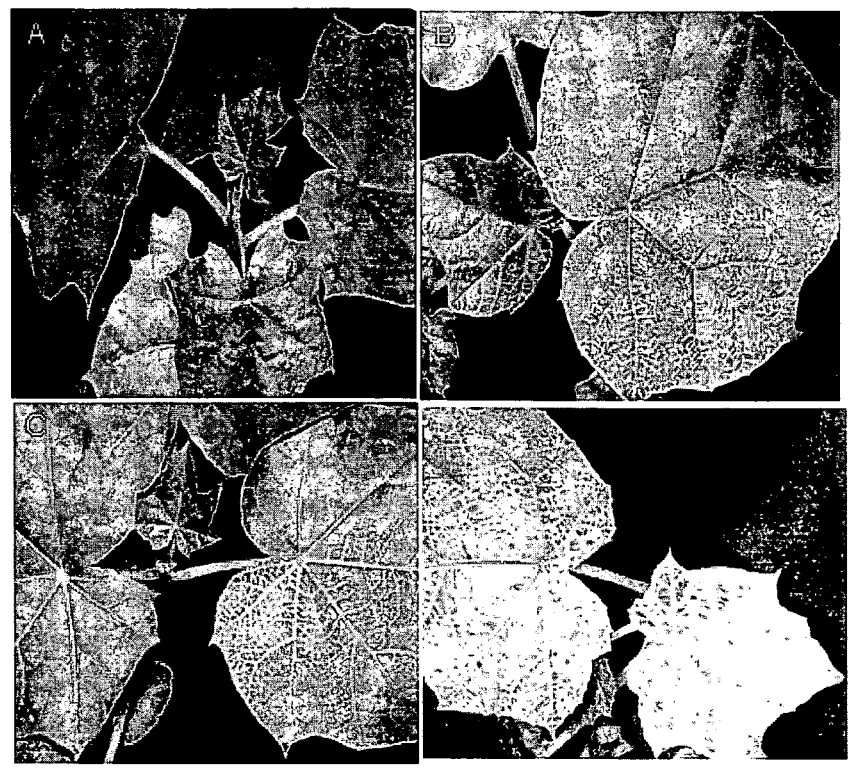
FIGS. 4A-4G show silencing of the *J. curcas* PDS gene. Infection of *J. curcas* plants with recombinant TRV alone (FIG. 4A) or TRV carrying a *J. curcas* PDS gene fragment (FIGS. 4B, 4C, 4D). TRV2-PDS-300 and TRV2-PDS-700 refer to insert size of 300 bp and 700 bp of the PDS gene in the TRV2 vector. Infection with TRV-PDS-300 (FIG. 4C) and TRV-PDS-700 (FIGS. 4B, 4D) silenced endogenous PDS gene in *J. curcas* plants and inhibited carotenoid biosynthesis resulting in various photo-bleaching phenotypes. Using the time-consuming agro-injection method, only a small region (leave vein) showed photo-bleaching phenotypes. The vacuum-infiltration method described here considerably increased the silencing efficiency (compare FIG. 4B and FIG. 4D). In addition, the treatment time is reduced to ⅕ that used for agro-injection.
Figure 4:
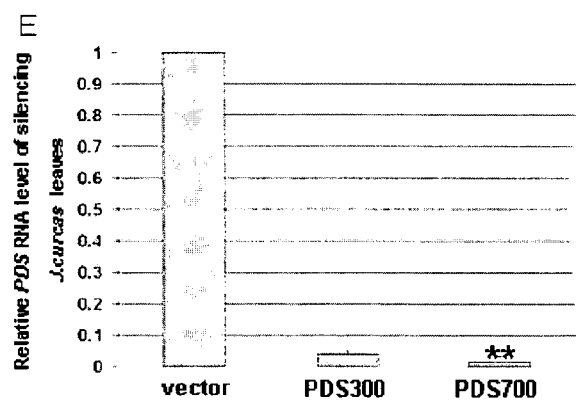
Figure 4:
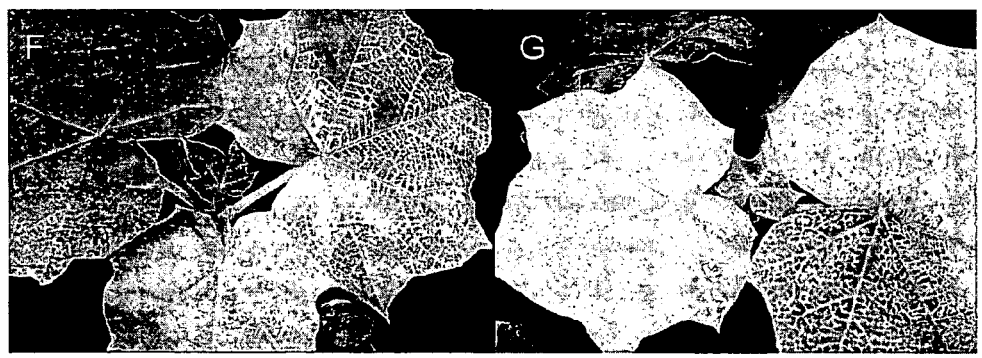

A mixture of *Agrobacterium* cultures containing pTRV1 and pTRV2-PDSS or pTRV2-PDSL was infiltrated onto *J. curcas* plants with 2-3 true leaves (for details see Example 1). Ten days post agro-injection very weak silencing effect was observed in veins of the third and fourth leaf of plants treated with either TRV-PDSS (data not shown) or TRV-PDSL (FIG. 3B). For VIGS in *Jatropha*, we found that the agro-injection method is not only time-consuming but also does not work very well and reproducible for some genes such as PDS. Therefore, we explored the use of vacuum infiltration to increase the VIGS efficiency and reproducibility. Using the same *Agrobacterium* culture mix, the silencing efficiency was much improved with the application of vacuum using a pump (compare FIG. 4B with FIG. 4D). Moreover, the treatment time could be reduced to ⅕ that of agro-injection. The effect of PDS insert size on the silencing efficiency was also found (compare FIGS. 4C and 4D). We also performed real-time PCR analysis to determine the relative PDS mRNA levels in silenced *J. curcas* leaves shown in FIGS. 4C and 4D. The PDS mRNA level was reduced by more than 95% for TRV-PDSS and 98% for PDSL compared to the vector control (FIG. 4E). In these experiments, the rbcL mRNA was used as a loading control. Statistically lower PDS mRNA level indicates that a longer in TRV-PDSL rendered a more efficacious silencing effect which was visible uniformly throughout the entire leaf.

We found the vacuum infiltration also worked better than the injection method for other genes, such as the CH42 gene (compare agro-injection data in FIG. 4F with vacuum infiltration data in FIG. 4G). Taken together, the vacuum infiltration method is more superior to the ago-injection method as it saves time as well as gives a better silencing effect. These results and the phenotypic data provide further evidence that the TRV-VIGS system could be successfully used to induce efficient silencing of desired endogenous *J. curcas* genes.

Example 4

Co-Silencing Multiple Genes in One Vector

Higher plants often contain complex and big gene family to render them more resistant to mutation or to provide gene functional specialization, e.g. use under biotic or abiotic stress. Because of functional redundancy it is quite common to find no obvious phenotypes when a single gene of a multigene family is silenced. Therefore, silencing of multiple genes could provide a valuable approach to studying functions that depend on the independent expression of two or more genes. We assessed the gene silencing efficiency of the TRV-VIGS by co-silencing the expression of the CH42 gene and the PCNA gene. The latter encodes the proliferating cell nuclear antigen (PCNA) in meristems of *J. curcas*.

In Examples 2 and 3, we have proven the silencing of the CH42 gene by TRV-CH42S and TRV-CH42L. To determine whether the TRV vector can be used to silence a gene expressed in meristems, we targeted the PCNA gene. PCNA is a highly conserved processivity factor for DNA polymerase δ, which is required for DNA replication and repair, and is highly expressed in dividing cells such as shoot apical meristems (Kelman, 1997).

We amplified the PCNA homolog from *J. curcas*. PCR primers were designed to target the conserved 614-bp cDNA of PCNA from different species of Euphorbiaceae family. This partial PCNA cDNA was cloned into pTRV2 to give pTRV2-PCNA and it was also inserted into pTRV2-CH42 vector to give pTRV2-CH42 co-PCNA.

Figure 5:
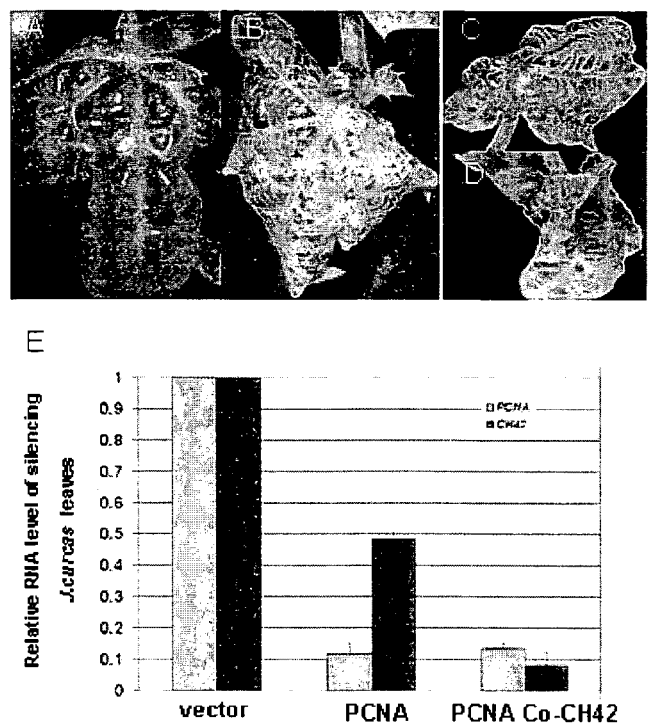
FIGS. 5A-5E show co-silencing of two genes in one vector. Silencing of the meristemic-specific gene PCNA alone (FIG. 5A) and co-silencing of CH42 and PCNA (FIGS. 5B and 5C: adaxial side of leaf.

A mixture of *Agrobacterium* cultures containing pTRV1 and pTRV2-PCNA or pTRV2-CH42 co-PCNA was vacuum-infiltrated into *J. curcas* plants with 2-3 true leaves. Eight days post-infiltration severe symptoms appeared, and at 18 dpi, shoot extension ceased in all tested plants and leaves curled downward typical of leaf phenotype with silenced PCNA expression. At 21-28 dpi, the curled leaves became detached from the tree truck and the main shoot never resumed normal growth for at least one month. TRV CH42-co-PCNA infected plants displayed co-silencing phenotypes with both yellow leaves and stunted shoots (FIGS. 5B, 5C, 5D), suggesting that the two endogenous genes, CH42 and PCNA, were both silenced. These data demonstrate that the TRV VIGS system can be used to knock down the expression of two or more genes thus allowing the deciphering of gene function in the event of functional redundancy.

Example 5

Co-Silencing of the Host Viral Resistance System Increases the Silencing Efficiency RNA silencing is one of the natural plant defense mechanisms against virus infection. We hypothesized that the co-silencing of the host viral resistance system using TRV-VIGS should result in more efficient VIGS.

A current model for antiviral silencing in higher plants, using *Arabidopsis thaliana* as an example, suggests that double-stranded (ds) RNA replication intermediates of viral genomic RNAs or highly structured regions within single-stranded viral RNAs are first cleaved by RNase III-type Dicer-like 4 (DCL4) or alternatively by DCL2 to produce 21- or 22-nucleotide (nt) small interfering RNAs (siRNAs) (Baulcombe, 2004). This model implies that DCL4 is an important *Arabidopsis* viral resistance gene (Deleris et al., 2006). We tested the ability of the TRV-VIGS system to silence DCL4 and also explored the possibility of increasing silencing efficiency of a candidate gene by co-silencing of DCL4. We used the marker gene CH42 to examine this possibility.

First, we have shown that infection with TRV-CH42L alone can result in knockdown of CH42 gene expression. Next, we investigated whether the silencing efficiency can be increased by co-silencing of *Jatropha* DCL4. To amplify the DCL4 homolog from *J. curcas*, PCR primers were designed to target conserved sequence motifs of DCL4 from different species of the Euphorbiaceae family. Using PCR, applicants cloned an anti-sense 678-bp fragment of the *J. curcas* DCL4 cDNA and inserted this fragment into pTRV2-CH42L to give pTRV2-CH42L co-DCL4. A mixture of *Agrobacterium* cultures containing pTRV1 and pTRV2-CH42L co-DCL4 was vacuum-infiltrated onto *J. curcas* plants and phenotypes were observed at 18 dpi. Results showed that co-silencing of DCL4 and CH42 gave a better silencing effect compared silencing of CH42 gene alone (compare FIG. 6B with FIG. 6A).

We also used real-time PCR to analyze the relative DCL4 and CH42 RNA levels of silenced *J. curcas* leaves. CH42 mRNA levels were lower in the co-silenced plants compared to plants silenced only in the expression of CH42 alone (p<0.01) (FIG. 6C).

Taken together, the phenotypic and molecular analyses demonstrate that co-silencing DCL4 can confer a higher VIGS efficiency in treated *J. curcas* plants. It is obvious that this strategy can also be extended to co-silencing of other host genes involved in viral resistance. Furthermore, co-silencing of the viral-resistant system also can be used to increase the efficiency of other VIGS systems in other plant species.

These results and the phenotypes data indicate that the TRV-VIGS system could be successfully used to induce silencing of other desirable endogenous *J. curcas* genes. We have generated expressed sequence tags (EST) for several different *Jatropha* tissues such as seeds and flowers. These expressed sequence tags (ESTs) provide a wealth of information for functional genomics study of *Jatropha*. Therefore, the VIGS assay described here will offer a means to test the function of *Jatropha* gene sequences in a homologous system. Using a normalized cDNA library it will be possible to conduct large scale screens of gene function with the TRV-based VIGS system.

Example 6

Knock-Down of KASII mRNA Levels Using TRV VIGS System

Triacylglycerols produced by plants are one of the most energy-rich and abundant forms of reduced carbon available from nature. Given their chemical similarities, plant oils represent a logical substitute for conventional diesel, a non-renewable energy source. The functional properties of both animal fats and vegetable oils are largely determined by the properties of the fatty acids that are esterified to triacylglycerol.

We tested the ability of the TRV-VIGS system for high-throughput functional analysis of genes involved in fatty acid biogenesis. *Jatropha* seed oil contains predominantly unsaturated 18-carbon (18C) fatty acids (more than 80%) (Jones et al., 1991), whereas palm oil contain a higher proportion (about 50%) of 16-carbon (16C) saturated fatty acids. We hypothesized that the modulation of KASII level using TRV-VIGS should result in the conversion of C18 to C16 fatty acids in *J. curcas* leaves. In the model plant *Arabidopsis*, the KASII gene encoding β-ketoacyl-acyl carrier protein synthase II is responsible for the elongtion of 16:0-ACP to 18:0-ACP (Pidkowich et al., 2007). First, we investigated whether TRV infection of *J curcus* alone has an effect on its leaf fatty acid composition. A mixture of *Agrobacterium* containing pTRV1 and pTRV2 was infiltrated into *J. curcas* plants (FIG. 7A, panel (a)). Eighteen days post infiltration, the upper leaves of these plants showed no obvious phenotypes and no change in fatty acid profile was observed when compared with mock-treated *J. curcas* (FIG. 7C for vector and not show the mock-inoculation data). These results, together with the above-described phenotypic data, confirm that TRV infection alone has no effect on *Jatropha* leaf fatty acid profile and therefore the TRV-VIGS system can be used to study genes involved in fatty acid biogenesis.

To silence KASII function using TRV-VIGS, we used use PCR to clone an antisense 829-bp fragment of the *J curcas* KASII cDNA corresponding to nt 240-1063 (GenBank No. DQ987700). This fragment was inserted into pTRV2 to give pTRV2-KASII. A mixture of *Agrobacterium* cultures containing pTRV1 and pTRV2-KASII was infiltrated into *J. curcas* plants (FIG. 7A, panels (b), (c), (d)). Eighteen days post-infiltration, the upper leaves showed two kinds of phenotypes: some leaves showed mild yellowish phenotypes (FIG. 7A, panel (b)) whilst other newly emerged leaves curled downward with brownish leaf blade, and shoot extension ceased (FIG. 7A, panels (c) and (d)). We performed real-time quantitative RT-PCR, using total RNA extracted from *J. curcas* plants infected with TRV-KASII or TRV alone. In TRV-KASII infected plants showing severe phenotypes, the KASII mRNA was reduced by more than 76% compared to the TRV infected control (FIG. 7B) when rbcL mRNA was used to normalize loading of the samples. These results showed that the TRV-based VIGS system can efficiently silence targeted host genes and can be used as a rapid means to assay the role of candidate genes in fatty acid biogenesis pathway.

We used gas chromatograms to examine fatty acid methyl esters from control and silenced *J. curcas* leaves. Lipids were extracted with 2:1 chloroform: methanol and transmethylated to fatty acid methyl esters by incubation with equal volume of 3N methanolic-HCL (SIGMA). An Agilent 6890 GC machine was used to analysis fatty acid methyl esters profile. As expected, higher 16C and lower 18C were found in KASII VIGS plants compared to control plants (FIG. 7C and Table 3). The 18C to 16C conversion was more obvious in samples with severe phenotypes and the degree of conversion correlated with phenotypic severity. The amount of 16C:0 (palm oil-like fatty acid) can reach as high as 41% in leaf samples with severe phenotype. This level of C16:0 is nearly 50% level of that in palm oil. Not only the fatty acid chain length, but also the unsaturated/saturated fatty acid ratio was highly dependent on the KASII expression levels (Table 3). On the other hand, the vaccenic acid (18:1 trans-11) level increased when KASII expression was down-regulated. Mammals convert vaccenic acid it into rumenic acid, a conjugated linoleic acid, which shows anticarcinogenic properties (Banni et al., 2001). Our VIGS results in *Jatropha* show very similar fatty acid profile modification resulting by stable KASII RNAi silencing method in model plant *Arabidopsis* (Pidkowich et al., 2007), that indicates we functionally identified KASII gene in this biodiesel plants.

than the single KASII silencing plants. Therefore, co-silencing FATB gene can reverse the KASII single gene silencing effect on fatty acid metabolism, which further indicates that manipulation the balance of these two genes expression level is one potential method to get ideal bio-diesel fatty acid composition in *Jatropha* industry.

TABLE 3

Fatty Acid Composition of Vector CK, KASII Mild, KASII Severe and KASII co-FATB *J. curcas* (mol %)

| | 16:0 | 16:1$^3$ | 16:1$^9$ | 18:0 | 18:1$^9$ | 18:1$^{11}$ | 18:2 | 18:3 | 16:18 | S/US |
|---|---|---|---|---|---|---|---|---|---|---|
| CK | 16.5 ± 0.1 | 2.2 ± 0.4 | 2.0 ± 0.1 | 3.9 ± 0.1 | 2.1 ± 0.1 | 0.0 ± 0.0 | 15.1.1.1± | 51.1 ± 1.2 | 0.39 | 0.25 |
| KASII Mild | 26.6 ± 0.1 | 2.3 ± 0.1 | 3.6 ± 0.1 | 4.6 ± 0.3 | 1.7 ± 0.1 | 2.7 ± 0.1 | 12.9 ± 1.2 | 40.8 ± 1.1 | 0.60 | 0.44 |
| KASII Severe | 41.2 ± 0.3 | 0.0 ± 0.0 | 3.9 ± 0.2 | 6.1 ± 0.0 | 0.0 ± 0.0 | 4.8 ± 1.3 | 12.1 ± 0.7 | 24.0 ± 0.1 | 1.12 | 0.90 |
| KASII co-FATB | 26.5 ± 10. | 3.0 ± 0.2 | 3.8 ± 0.2 | 4.6 ± 0.1 | 0.4 ± 0.3 | 3.7 ± 0.1 | 9.9 ± 1.2 | 43.5 ± 1.2 | 0.61 | 0.44 |

Notes:
Means and standard of error of three independent samples are presented.
16:18 means the ratio of 16-carbon fatty acid to 18-carbon fatty acid.
S/US is the saturated/unsaturated fatty acid ratio.

We have demonstrated the co-silencing of 2 genes in *J. curcas* with the TRV VIGS system. We next examined whether the TRV VIGS system can be used to silence multiple genes in one vector. We hypothesized that the modulation of KASII and other enzyme levels using the TRV VIGS system should result in a fatty acid composition different from that obtained with silencing KASII alone. In *Arabidopsis*, KASII elongates 16:0-ACP to 18:0-ACP in the plastid, where it competes with three other enzymes at the first major branch point in fatty acid biosynthesis. Acyl-ACP thioesterase B (FATB), one of three enzymes, remove the acyl-ACP from 16:0-ACP and has been shown to be important for saturated fatty acid biogenesis such as 16:0 and 18:0 (Jones et al. 1995). Preventing the release of saturated fatty acids from ACP by down-regulating FATB lowered saturated fatty acid levels, which can improve biodiesel characteristics with regard to cold-temperature flow properties and NO emissions (Hawkins and Kridl, 1998). Using PCR we cloned a sense 796-bp fragment of the *J. curcas* FATB cDNA corresponding to nt 174-976 (GenBank No. EU106891) and inserted this fragment into pTRV2-KASII to give pTRV2-KASII co-FATB. A mixture of *Agrobacterium* cultures containing pTRV1 and pTRV2-KASII co-FATB was infiltrated onto *J. curcas* plants. Eighteen days post-infiltration, the upper leaves showed a weaker phenotype (only mild yellowish color) than that of leaves of plants treated with TRV-KASII. We performed real-time quantitative RT-PCR, using total RNA extracted from *J. curcas* plants infected with TRV-KASII co-FATB to confirm down-regulation of both the KASII and FATB genes in the same leaf sample. In TRV-KASII co-FATB infected plants, the mRNA were reduced by more than 81% for KASII and 84% for FATB compared to the TRV infected control (FIG. 7B) when rbcL mRNA was used to normalize RNA loading. We further used gas chromatography to examine fatty acid methyl esters from the co-silenced *J. curcas* leaves. The 18C to 16C conversion seen in knock-down of the KASII gene alone was dampened upon co-silencing of the FATB gene. As we expected according to the FATB T-DNA insertion mutant work in model plant *Arabidopsis* (Bonaventure et al., 2003), co-silencing FATB with KASII gene leads to less 18:0 and 16:0 level compared with the KASII only silencing plants. Not only the 18C fatty acid ratio, but also the unsaturated fatty acid ratio was much higher in FATB and KASII co-silencing These results also show that the TRV based VIGS system can efficiently suppress targeted host genes and can be used as a rapid means to assay the role of candidate genes in fatty acid biosynthesis. Therefore, we set out to silence putative *J. curcas* desaturase genes SAD1, SAD2, SAD3, FAD2-1, FAD2-2 and FAD6 homologs in *J. curcas* to investigate their role in fatty acid biosynthesis.

Example 7

Rapid Functional Analysis of Several Stearoyl-ACP Desaturase Genes by the TRV VIGS System in *J. Curcas*

One method of altering the unsaturated fatty acid content of oilseeds is by manipulating the expression of desaturase genes of these plants. Manipulating the expression of desaturase genes in transgenic crops such as soybean, maize and canola (oilseed rape) has led to oils with altered functionality and nutrition.

Stearoly-acyl carrier protein (Stearoyl-ACP) desaturase (SAD) catalyzes the first desaturation step in fatty acid biosynthesis, converting stearoyl-ACP to oleoyl-ACP. Therefore, SAD plays important roles in determining the chain length of fatty acids and the ratio of saturated to unsaturated fatty acids (Shanklin and Somerville, 1991). It has been shown that stearic acid content of oil in seed can be increased by downregulation of SAD expression level (Knutzon et al., 1992). Furthermore, the stearoyl desaturase-catalyzed enzymatic step leads to the synthesis of jasmonic acid (JA), a plant hormone important for abiotic and biotic stresses in plants (Kachroo et al., 2003). At the same time, SAD is also encoded by a gene family, and seven SAD genes are present in the *Arabidopsis* genome. We have isolated three *J. curcas* SAD genes by sequencing a *Jatropha* seed cDNA library. The functions of these 3 different SAD genes were investigated using the TRV-VIGS system.

Using PCR, we cloned a sense 796-bp fragment of the *J. curcas* SAD1 cDNA (GenBank No. DQ084491) to form pTRV2-SAD1. We also cloned a sense 868-bp and 847-bp fragments of the *J. curcas* SAD2 and SAD3 cDNA (SEQ ID NO:33 and SEQ ID NO:36, respectively). These cDNA fragments were inserted into pTRV2 to give pTRV2-SAD2 and pTRV2-SAD3. Mixtures of *Agrobacterium* cultures containing pTRV1 and pTRV2-SAD1, pTRV2-SAD2 or pTRV2-SAD3 were infiltrated onto different *J. curcas* plants. Four dpi after infections, newly emerged leaves showed yellowish vein phenotype (data not shown). At 10 dpi the vein phenotype was more obvious in TRV-SAD1 plants which displayed brownish veins and severe narrowing of leaf blades (FIG. 8A, panel (b)). Leaves and stems withering can be found in most of the TRV-SAD1 plants at 18 dpi (FIG. 8A, panels (c) and (d)). No phenotypes were seen in TRV-SAD2 plants (FIG. 8A, panel (e)). Much weaker phenotypes, such as partial leaf vein yellowing and leaf curling were found in TRV-SAD3 plant at 18 dpi (FIG. 8A, panels (f) and (g)). To confirm the down-regulation of the appropriate SAD gene, we performed real-time quantitative RT-PCR using total RNA extracted from infected *J. curcas* plants. Compared to the TRV-infected control plants, the SAD1 mRNA was reduced by 91% in TRV-SAD1 plants, the SAD3 mRNA was reduced by 75% in TRV-SAD3 plants (FIG. 8B).

We further used gas chromatography to examine fatty acid methyl esters from leaves of silenced *J. curcas* plants. At 10 dpi plants silenced in SAD1 expression (10 dpi in FIG. 8A, panel (b)), contained 10.8% stearic acid which is about 2.8 fold higher than that of vector control plants. On the other hand, these SAD1-silenced plants displayed little changes in their C16 fatty acid profile (FIG. 8C and Table 4). Meanwhile, all 18C unsaturated fatty acids were down-regulated. A higher saturated to unsaturated fatty acid ratio also indicated higher levels of saturated fatty acids in SAD1-silenced leaves (Table 4). At a later stage (SAD1L), dramatic changes were found in the levels of 16C fatty acid as well as 18C fatty acids (Table 4). These data provide the first genetic evidence that not only 18:0-ACP but also 16:0-ACP can serve as substrates of the SAD genes. In fact, the SAD1 gene should be named as $\Delta^9$-ACP desaturase gene. For plants silenced in SAD3 expression changes in GC profile are consistent with the much weaker phenotypes. Leaves from these plants contained only 4.5% stearic acid, which was only 0.6% higher than that in the vector control plants.

Example 8

Manipulation of FAD2-1 and FAD6 Expression Level Can be Used to Produce High Oleic Acid Content in *Jatropha* Plants Oleic acid (18:1) content of plant oils is a quantitative trait with importance for human and animal nutrition and also for use of plant oil as a source of biodiesel (Durrett et al., 2008). Oils with higher oleic acid content have more oxidative stability, healthier and present beneficial cooking properties. Several QTLs for seed oil content of many plant species such as *Arabidopsis*, canola, peanut and maize, mapped to fad2 genes (Patel et al., 2004; Belo et al., 2008). FAD2 encodes an endoplasmic reticulum-localized $\Delta12$ desaturase required for converting the monounsaturated oleic acid (18:1) to the polyunsaturated linoleic acid (18:2), itself the precursor to linolenic acid (18:3; Okuley et al., 1994). On the other hand, the fatty acid desaturase-6 gene (FAD6) encodes a delta-12 desaturase that functions in plastids. By sequencing the *Jatropha* cDNA library we found at least 2 FAD2 genes (FAD2-1 and FAD2-2) in the *J. curcas* genome. These two FAD2 genes share high nucleotide and amino acid sequence similarity. We used the TRV-VIGS system to analyze the function of these two genes in fatty acid biosynthesis.

Using PCR, we cloned a sense 862-bp and 711-bp fragments of the *J. curcas* FAD2-1 and FAD2-2 cDNA, respectively (JcFAD2-1, GenBank No. DQ157776). These fragments were inserted into pTRV2 to give pTRV2-FAD2-1 and pTRV2-FAD2-2. We also used PCR to clone a sense 835-bp fragment of the *J. curcas* FAD6 cDNA (GenBank No. EU106889), and this fragment was inserted into pTRV2 to give pTRV2-FAD6. Mixtures of *Agrobacterium* cultures containing pTRV1 and pTRV2-FAD2-1, pTRV2-FAD2-2 or pTRV2-FAD6 were separately infiltrated into different *J. curcas* plants. No obvious morphological phenotype was seen in plants infected with these recombinant viruses for more than one month (data not shown). We also used real-time PCR to examine mRNA levels in silenced *J. curcas* plants. The

TABLE 4

Fatty Acid Composition of Several Desaturase Gene VIGS *J. curcas* Leaves (mol %)

| | 16:0 | 16:1$^3$ | 16:1$^9$ | 18:0 | 18:1 | 18:2 | 18:3 | 16:18 | S/US |
|---|---|---|---|---|---|---|---|---|---|
| CK | 16.5 ± 0.1 | 2.2 ± 0.4 | 2.0 ± 0.1 | 3.9 ± 0.1 | 2.1 ± 0.1 | 15.1 ± 1.1 | 51.1 ± 1.2 | 0.39 | 0.25 |
| SAD1-E | 17.9 ± 0.5 | 1.6 ± 0.1 | 1.0 ± 0.0 | 10.8 ± 0.6 | 0.8 ± 0.4 | 14.7 ± 1.4 | 45.0 ± 2.5 | 0.37 | 0.42 |
| SAD1-L | 23.8 ± 1.1 | 0.0 ± 0.0 | 0.0 ± 0.0 | 14.6 ± 1.4 | 0.0 ± 0.0 | 10.3 ± 1.8 | 28.2 ± 2.5 | 0.67 | 0.62 |
| SAD3 | 16.5 ± 0.0 | 2.2 ± 0.1 | 1.7 ± 0.5 | 4.5 ± 0.1 | 1.7 ± 0.0 | 16.9 ± 0.8 | 51.6 ± 0.1 | 0.32 | 0.27 |
| FAD2-1 | 13.6 ± 0.6 | 2.4 ± 0.3 | 1.7 ± 0.0 | 3.9 ± 0.5 | 17.8 ± 2.1 | 5.4 ± 2.0 | 49.0 ± 1.8 | 0.30 | 0.21 |
| FAD2-2 | 15.7 ± 0.6 | 2.6 ± 0.3 | 1.6 ± 0.1 | 3.7 ± 0.4 | 1.2 ± 0.6 | 15.8 ± 1.3 | 50.9 ± 1.0 | 0.43 | 0.23 |
| FAD6 | 15.4 ± 1.5 | 2.1 ± 0.3 | 1.5 ± 0.3 | 3.4 ± 0.1 | 5.0 ± 0.2 | 17.8 ± 1.9 | 45.5 ± 2.3 | 0.29 | 0.23 |

Notes:
Means and standard error of three independent samples are presented.
16:18 means the ration of 16-carbon fatty acid to 18-carbon fatty acid.
S/US is the saturated/unsaturated fatty acid ratio.
The samples of SAD1-E are the leaves of SAD1 VIGS *J. curcas* at 12 dpi.

These biochemical results along with the above-described phenotypic data indicate that TRV VIGS could be used to rapidly characterize individual members of a multiple gene family, which may share overlapping functions. Also seed-specific suppression of the SAD1 ($\Delta^9$-ACP desaturase) gene can be used to produce *Jatropha* oil containing high-stearic acid content.

mRNA level was reduced by 83% for FAD2-1 in TRV-FAD2-1 plants and 82% for FAD2-2 in TRV-FAD2-2 (FIG. 8B), whereas the FAD6 mRNA level in TRV-FAD6 plant was only 8% that of vector control plants. Although there were no obvious morphological phenotypes for plants silenced in one of these 3 $\Delta^{12}$ desaturase genes, dramatic changes were found in the GC profile of FAD2-1 silenced plants (FIG. 8C and Table 4). In FAD2-1 VIGS plants, the linoleic acid (18:2) was down-regulated to 5.4% from 15.4% found in vector control plants. By contrast the oleic acid content was up-regulated to 17.8% from 2.1%. In FAD2-2 VIGS plants, the oleic acid was even lower than that found in vector control plants. Data obtained by the applicants also showed that the FAD6 gene has minor contributions to oleic acid accumulation in *J. curcas*. In the FAD6-silenced plants, the oleic acid content was up-regulated to 5.0% from 2.1%, whereas the linoleic acid (18:2) content was up-regulated slightly. Most interestingly, both the ratio of 16C to 18C and the saturated to unsaturated fatty acids were down-regulated, which means that knockdown of FAD2-1 and FAD6 genes can result in the production of longer fatty acids and unsaturated fatty acids.

These results provide further evidence that TRV VIGS could be used to rapidly screen for function of members of a multiple gene family, which may share similar functions. Also seed-specific suppression of FAD2-1 and FAD6 ($\Delta^{12}$-ACP desaturase) gene expression can be used to produce plant oil with higher oleic oil and lower 16C in seed of *J. curcas*.

Example 9

Using VIGS to Analyze Function of Transcription Factor Genes in *J. curcas*

Transcription factors (TFs)-mediated regulation of mRNA production is a major mode of regulation for plants mounting responses to developmental signals and environmental cues, and transcriptional regulation has been widely studied in model plants, such as *Arabidopsis* and rice. We tested the utility of the TRV-VIGS system for high-throughput analysis TF gene functions.

The ASYMMETRIC LEAVES 1 (AS1) gene in *Arabidopsis* and its ortholog the ROUGH SHEATH2 (RS2) gene in maize (Zea mays) and PHAN in Antirrhinum seem to play an evolutionarily conserved role in shoot apical meristem, leaf and fruit development (Sun et al., 2002; Alonso-Cantabrana et al., 2007). Both AS1 and its orthologs belong to the R2R3 MYB type of TF proteins. AS1 functions as a transcriptional repressor by binding to the promoter of class I KNOTTED1-like homeobox (KNOX) genes. This factor promotes stem cell function through the regulation of phytohormone activities (Alonso-Cantabrana et al., 2007). AS1 operates as a negative regulator of inducible resistance against these pathogens by selectively binding to the promoters of genes controlled by the immune activator, jasmonic acid (JA), damping the defense response. By contrast, AS1 is a positive regulator of salicylic acid (SA)-independent extracellular defenses against bacterial pathogens (Nurmberg et al., 2007).

To amplify the AS1 homolog from *J. curcas*, PCR primers were designed to target conserved sequence motifs of AS1 from different species of the Euphorbiaceae family. Using PCR we cloned a sense 630-bp fragment of the *J. curcas* AS1 cDNA which was inserted in to pTRV2 to give pTRV2-AS1. A mixture of *Agrobacterium* cultures containing pTRV1 and pTRV2-AS1 vector was infiltrated into different *J. curcas* plants. After 27 dpi, obvious phenotypes can be seen in newly emerged leaves. Severe downward curling was the most obvious phenotype both from the adaxial side (FIG. 9A, panel (a)) as well as from the abaxial side (FIG. 9A, panel (b)) of leaves. Leaves silenced in AS1-expression had normal adaxial/abaxial polarity but displayed a specific disruption in the adaxial domain, leading to the formation of ectopic leaf blades on the lateral flanks of vein (FIG. 9A, panels (a), (b), (c),)d)). Ectopic leaf blades (EB) emerged from the primary blade (PB) and showed a fixed polarity with the adaxial surface facing away from the rib (FIG. 9A, panels (c), (d)).

We further investigated the morphological changes in detail by microscopy. Using scanning electron microscopy (SEM), we found ectopic adaxial leaf blade structures developed directly from the primary leaf blade (FIG. 9B). Moreover, the adaxial surface was facing away from the rib and the abaxial surface with a large number of stomata was covered by the ectopic leaf blades, just like a withering flower. Transverse sections through ectopic blades confirmed that these are differentiated leaf blades, with a recognizable palisade layer in the upper mesophyll, polarized vascular tissue, and a spongy mesophyll. Quantitative RT-PCR data confirmed that the AS1 mRNA level was reduced by 69% (FIG. 9H).

We also checked the expression level of a putative *J. curcas* KNAT1-like gene in AS1-silenced leaves. Quantitative RT PCR data showed that *J. curcas* KANT1-like gene expression was 3.28 fold that of the vector control plants. This result provides evidence that the KNAT1-like gene is negatively regulated by AS1 (FIG. 9H). In *Arabidopsis*, ectopic expression of KNAT1 leads to production of ectopic adaxial leaf blade (Sun et al., 2002; Theodoris et al., 2003).

These molecular data and the adaxial leaf blade phenotype provide further evidence that TRV VIGS could be used in *J. curcas* to rapidly screen for function of TF genes. Such genes may be important for plant fruit development and oil body formation in developing seed. More importantly, recent evidence shows that common networks regulate leaf and fruit patterning in *Arabidopsis* (Nurmberg et al. 2007). Thus, one can use the leaf as a model system for rapid assessment of TF gene functions and to make use of such information to further to make use of these genes to modify or enhance the quality and quantity of *J. curcas* oil. In certain embodiments, the invention also provides plant products obtained from transgenic plants of the invention. The term "plant product" is intended to include anything that may be obtained from a particular plant, including, for example, fruits, seeds, pollen, ovules, plant embryos, oils, juices, waxes, proteins, lipids, fatty acids, vitamins, plant tissues in whole or in part, (e.g. roots, leaves, stems, flowers, bark), cells, cell suspensions, tubers and stolons.

Example 10

Functional Analysis of Small RNA Pathway Genes in *J. curcas* by VIGS

Small RNAs (smRNAs) regulate processes as diverse as plant resistance to viruses, and plant development and differentiation. We tested the ability of the TRV-VIGS system for high-throughput analysis of functions of genes involved in smRNA biogenesis pathways.

All RNA-silencing pathways require the genesis of 18- to 26-nt smRNAs from the cleavage of double-stranded RNA (dsRNA) or highly structured regions within single-stranded viral RNAs. MicroRNA is one important kind of smRNAs. Bound to ARGONAUTE1 (AGO1) protein, miRNAs guide RNA-induced silencing complexes (RISCs) to cleave mRNAs with partial or complete sequence complementarity. Accordingly, *Arabiciopsis* AGO1 binds miRNAs and displays slicer activity toward miRNA targets, and strong ago1 loss-of-function mutants overaccumulate miRNA target transcripts (Baulcombe, 2004; Baumberger and Baulcombe, 2005). AGO1 has also proven to bind viral-derived siRNA and ago1 mutant show hypersusceptibility to virus (Beclin et al., 2002; Morel et al., 2002). By sequencing the cDNA library, we found four cDNA sequences encoding putative AGO1 in *J. curcas*.

Using PCR we cloned a sense 855-bp fragment of the *J. curcas* AGO1 cDNA which was inserted into pTRV2 to give pTRV2-AGO1. A mixture of *Agrobacterium* cultures containing pTRV1 and pTRV2-AGO1 infiltrated into different *J. curcas* plants. After 27 dpi, diverse and varied phenotypes can be seen in new emerged leaves. Severe upward curling was the most obvious phenotype both from the adaxial side (FIG. 9A, panel (e)) and the abaxial side (FIG. 9A, panels (f), (g)) of leaves. AGO1-silenced leaves showed a specific disruption in the abaxial domain, leading to the formation of abaxial ectopic leaf blades (FIG. 9A, panels (f), (g)). Typical serrate phenotypes, including deep serration some even into the bottom of the leaf blade, were found in the AGO1-silenced plants (FIG. 9A, panels (h), (i), (j)).

We further observed the morphological changes in detail by microscopy. Using SEM, ectopic abaxial leaf blades structure emerged along with the leaf vein and faced toward the vein (FIG. 9D). Transverse sections through ectopic blades confirmed that these were differentiated leaf blades, with a recognizable palisade layer in the upper mesophyll and a spongy mesophyll.

There were some bubbles in the adaxial domain of AGO1-silenced leaves (FIG. 9A, panel (e)). Transverse sections through these bubbles confirmed that one ectopic leaf vein-leaf blade mixed structure with polarized vascular tissue and parenchyma, a two-layer blade palisade in the upper mesophyll and a spongy mesophyll (FIG. 9F).

Real time RT-PCR data confirmed that AGO1 mRNA levels were reduced by 69% (FIG. 9I). We also checked the expression level of one putative *J. curcas* miR155/156 regulated gene PHAVOLUTA (PHAV) in AGO1-silenced leaves. Real time RT-PCR data shows that *J. curcas* PHAV gene expression was 2.82 fold that of the vector control plants. This result shows that PHAV gene expression is negatively correlated with AGO1 mRNA levels (FIG. 9H). In *Arabidopsis*, ectopic PHAV expression leads to the formation of ectopic abaxial leaf blade (Kidner and Martienssen, 2004).

These molecular data and the adaxial leaf blade phenotype provide further evidence that TRV VIGS could be used in *J. curcas* to rapidly screen for function of genes involved in smRNA biogenesis pathway.

Example 11

Using VIGS to Functionally Analyze Genes Involved in Toxin Biosynthesis in *J. curcas*

Curcin is a toxic protein specifically expressed in *Jatropha* seeds. It is one of the several toxic components which prevent *Jatropha* seeds and protein meal to be used as animal feed (Thomas et al., 2008). We tested the ability of the TRV-VIGS system to knock-out or knock-down curcin gene expression.

Using PCR, we cloned an anti-sense 836-bp fragment of the *J. curcas* curcin cDNA (curcin GenBank No. AY069946). This fragment was inserted into pTRV2 to give pTRV2-curcin. A mixture of *Agrobacterium* cultures containing pTRV1 and pTRV2-curcin was infiltrated into *J. curcas* plants. After 18 dpi, no obvious phenotype was found in curcin-silenced leaves. Silenced leaves were collected and curcin antiboby was used to detect the curcin protein. Western blot analysis showed that silenced leaves contained only 2-3% of curcin found in leaves of vector control plant. Coomassie Bright Blue staining of the large subunit of ribulose 1,5-bisphosphate carboxylase/oxygenase indicates comparable loading of the samples.

These data show the TRV VIGS system can be used for analysis of gene function in biogenesis pathways of toxic agents in *Jatropha*.

Example 12

Analysis of TRV VIGS System in Other Plants

According to the description from the International Committee on Taxonomy of Viruses (http colon backslash www dot ncbi dot nlm dot nih dot gov backslash ICTVdb backslash ICTVdB backslash 00 dot 072 dot 0 dot 01 dot 001 dot htm; hereinafter "ICTV"), TRV has a fairly wide host range. In addition, Dinesh Kumar et al. (2007) contains an extensive list of susceptible hosts. In order to determine whether the TRV VIGS system can be used for plants within the susceptibility lists, we tested the synthetic TRV VIGS (sTRV VIGS) system of the present invention in other putative hosts of TRV (ICTV; Dinesh Kumar et al. (2007)). We noted that different kinds of beans were independently listed as susceptible hosts in Dinesh Kumar et al. (2007) instead of a family or genus. Therefore, we chose some plants from different genera, but all in single Faboideae subfamily in the Fabaceae family within the Fabales order: common bean (*Phaseolus vulgaris*), peanut (*Arachis hypogaea*) and soybean (*Glycine max*). In addition, we also chose castor bean (*Ricinus communis*) which is from the same family (Euphorbiaceae) but a different subfamily with *Jatropha*. We found that the sTRV VIGS system does work in castor bean, although less potently than in *Jatropha*. After 18 dpi, CH42 silencing effect can be found in both inoculated leaf and systemic leaf (FIG. 11E). Recombinant TRV RNA1 and RNA2 can also be detected in almost all tested castor bean plants leaves (FIG. 12, lanes 11, 12, 14-17). A few necrotic spots (indicated by dark arrow in FIG. 11D) were seen in the inoculated leaf of the treated common bean. However, no necortic spots were seen in systemic leaf of the treated common bean (indicated by white arrow in FIG. 11D). This fewer necrotic spot phenotype is also correlated with very low viral RNA 1 and RNA2 accumulation in the inoculated leaves of the common bean (FIG. 12, lane 20). It appears that the virus replication was heavily limited by host plant cell death and thus can not move systemically. Both the phenotypic data and molecular data in common bean suggest that this host is a local necrotic host of the TRV strain. ICTV also describes common bean as a "necrotic local lesions; no systemic infection". Systemic leaves are always required for functional gene analysis in VIGS. Common bean, as a local necrotic host, therefore is not suitable as a host of the TRV VIGS system.

We also chose another bean species from the same *Phaseolus* genus with common bean, namely mung bean (*Phaseolus aureus*) (http colon backslash en dot wikipedia dot org backslash wiki backslash Mung underscore bean), to demonstrate that there is no reasonable expectation that the host range could be extended from one listed-plant species to the whole genus of plants or even to the whole family of plants. No local necrotic lesion and no viral RNA were found in mung bean plants (FIG. 12, lanes 6-8). This finding demonstrates that mung bean is not a host for TRV, although it is a near relative of common bean which is a local host of TRV.

We did not observe any silencing effect in other two listed host plants, peanut (*Arachis hypogaea*) and soybean (*Glycine*

*max*), after treating with sTRV2:JcCH42 (FIG. 11A and FIG. 11C). No viral RNA can be detected in peanut leaf (FIG. 12, lanes 1-3).

The data obtained from this example highly suggests that the TRV VIGS system can work in some plants in the TRV susceptible lists (ICTV; Dinesh Kumar et al. (2007)), but cannot work in all of the listed plants. The data obtained in this example also shows the unpredictability of which plants may be hosts for TRV and for which plants the TRV VIGS system can be used for functional gene analysis. For example, the data shows the unpredictability even between plants having a near evolutionary relationship, such as common bean and mung bean which are both in the same genus. The data shows that mung bean is not a host for TRV, but that common bean is a local necrotic host. Even thought common bean is a local necrotic host, it is not suitable for functional gene analysis by the TRV VIGS system. Thus, the present example demonstrates the inherent unpredictability of plant-viral interactions, for example the unpredictability as to the susceptibility of any given plant species to TRV and to the ability of the TRV VIGS system to be useful for functional gene analysis in any given plant species.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Alonso-Cantabrana, H. et al. (2007). Common regulatory networks in leaf and fruit patterning revealed by mutations in the *Arabidopsis* ASYMMETRIC LEAVES1 gene. *Development* 134:2663-2671.

Angell, S. M. and Baulcombe, D. C. (1999). Technical advance: potato virus X amplicon-mediated silencing of nuclear genes. *Plant J* 20:357-362.

Banni, S. et al. (2001). Vaccenic acid feeding increases tissue levels of conjugated linoleic acid and suppresses development of premalignant lesions in rat mammary gland. *Nutr Cancer* 41:91-97.

Baulcombe, D. (2004). RNA silencing in plants. *Nature* 431:356-363.

Baumberger, N. and Baulcombe. D. C. (2005). *Arabidopsis* ARGONAUTE1 is an RNA Slicer that selectively recruits microRNAs and short interfering RNAs. *Proc Natl Acad Sci USA* 102:11928-11933.

Beclin, C. et al. (2002). A branched pathway for transgene-induced RNA silencing in plants. *Curr Biol* 12:684-688.

Belo, A. et al. (2008). Whole genome scan detects an allelic variant of fad2 associated with increased oleic acid levels in maize. *Mol Genet Genomics* 279:1-10.

Bonaventure, G. et al. (2003). Disruption of the FATB gene in *Arabidopsis* demonstrates an essential role of saturated fatty acids in plant growth. *Plant Cell* 15:1020-1033.

Brigneti, G. et al. (2004). Virus-induced gene silencing in Solanum species. *Plant J* 39:264-272.

Burch-Smith, T. M. et al. (2004). Applications and advantages of virus-induced gene silencing for gene function studies in plants. *Plant J* 39:734-746.

Burch-Smith, T. M. (2006). Efficient virus-induced gene silencing in *Arabidopsis*. *Plant Physiol* 142:21-27.

Chen, J. C. et al. (2005). Silencing a prohibitin alters plant development and senescence. *Plant J* 44:16-24.

Chung, E. et al. (2004). A method of high frequency virus-induced gene silencing in chili pepper (*Capsicum annuum* L. cv. Bukang). *Mol Cells* 17:377-380.

Deleris, A. et al. (2006) Hierarchical action and inhibition of plant Dicer-like proteins in antiviral defense. *Science* 313:68-71.

Dinesh Kumar et al. (2007). Tobacco rattle virus vectors and related compositions and methods. U.S. Pat. No. 7,229,829 B2.

Durrett, T. P. et al. (2008). Plant triacylglycerols as feedstocks for the production of biofuels. *Plant J* 54:593-607.

Fu, D. Q. et al. (2005). Virus-induced gene silencing in tomato fruit. *Plant J* 43:299-308.

Hawkins, D. J. and Kridl, J. C. (1998). Characterization of acyl-ACP thioesterases of mangosteen (*Garcinia mangostana*) seed and high levels of stearate production in transgenic canola. *Plant J* 13:743-752

Jones, A. et al. (1995). Palmitoyl-acyl carrier protein (ACP) thioesterase and the evolutionary origin of plant acyl-ACP thioesterases. *Plant Cell* 7:359-371.

Jones, N. M. J. (1991). *Jatropha curcas*—a multipurpose species for problematic sites. *Land Resources Series* 1:1-12.

Kaloshian. I. (2007). Virus-induced gene silencing in plant roots. *Methods Mol Biol* 354:173-181.

Kelman, Z. (1997). PCNA: structure, functions and interactions. *Oncogene* 14:629-640.

Kidner, C. A. and Martienssen, R. A. (2004). Spatially restricted microRNA directs leaf polarity through ARGONAUTE1. *Nature* 428:81-84.

Knutzon, D. S. et al. (1992). Modification of Brassica seed oil by antisense expression of a stearoyl-acyl carrier protein desaturase gene. *Proc Natl Acad Sci USA* 89:2624-2628.

Liu, Y. et al. (2002a). Tobacco Rar1 EDS1 and NPR1/NIM1 like genes are required for N-mediated resistance to tobacco mosaic virus. *Plant J* 30:415-429.

Liu, Y. et al. (2002b). Virus-induced gene silencing in tomato. *Plant J* 31:777-786.

Liu, Y. et al. (2004). Virus induced gene silencing of a DEFICIENS ortholog in Nicotiana benthamiana. *Plant Mol Biol* 54:701-711.

MacFarlane, S. A. et al. (1999). Similarities in the genome organization of tobacco rattle virus and pea early-browning virus isolates that are transmitted by the same vector nematode. J Gen Virol 80 (Pt 1):273-276.

Morel, J. B. et al. (2002). Fertile hypomorphic ARGONAUTE (ago1) mutants impaired in post-transcriptional gene silencing and virus resistance. *Plant Cell* 14:629-639.

Narayana, D. S. A et al. (2007). Distinct Begomoviruses Closely Related to Cassava Mosaic Viruses cause Indian *Jatropha* Mosaic Disease. *Int'l J Virol* 3:1-11.

Nurmberg, P. L. et al. (2007). The developmental selector AS1 is an evolutionarily conserved regulator of the plant immune response. *Proc Natl Acad Sci USA* 104:18795-18800.

Okuley, J. et al. (1994. *Arabidopsis* FAD2 gene encodes the enzyme that is essential for polyunsaturated lipid synthesis. *Plant Cell* 6:147-158.

Patel, M. et al. (2004). High-oleate peanut mutants result from a MITE insertion into the FAD2 gene. *Theor Appl Genet* 108:1492-1502.

Pidkowich. M. S. et al. (2007). Modulating seed beta-ketoacyl-acyl carrier protein synthase II level converts the composition of a temperate seed oil to that of a palm-like tropical oil. *Proc Natl Acad Sci USA* 104:4742-4747.

Qu. J. et al. (2007). Artificial microRNA-mediated virus resistance in plants. *J Virol* 81:6690-6699.

Ruiz, M. T. et al. (1998). Initiation and maintenance of virus-induced gene silencing. *Plant Cell* 10:937-946.

Shanklin. J. and Somerville, C. (1991). Stearoyl-acyl-carrier-protein desaturase from higher plants is structurally unrelated to the animal and fungal homologs. *Proc Natl Acad Sci USA* 88:2510-2514.

Shi, B. J. et al. (1997). Plasmid vector for cloning infectious cDNAs from plant RNA viruses: high infectivity of cDNA clones of tomato aspermy cucumovirus. *J Gen Virol* 78 (Pt 5):1181-1185.

Sujatha, M. et al. (2008). Role of biotechnological interventions in the improvement of castor (*Ricinus communis* L.) and *Jatropha curcas* L. *Biotechnol Adv* 26:424-435.

Sun, Y. et al. (2002). ASYMMETRIC LEAVES1, an *Arabidopsis* gene that is involved in the control of cell differentiation in leaves. *Planta* 214:694-702.

Theodoris, G. et al. (2003). Conservation and molecular dissection of ROUGH SHEATH2 and ASYMMETRIC LEAVES1 function in leaf development. *Proc Natl Acad Sci USA* 100:6837-6842.

Thomas, R. et al. (2008). Therapeutic biology of *Jatropha curcas*: a mini review. *Curr Pharm Biotechnol* 9:315-324.

Valentine, T. et al. (2004). Efficient virus-induced gene silencing in roots using a modified tobacco rattle virus vector. *Plant Physiol* 136:3999-4009.

What is claimed is:

1. A method of virus-induced gene silencing (VIGS) in *Jatropha* comprising:
   (a) inserting a nucleic acid comprising a sequence of a first desired gene to be silenced into a vector comprising a tobacco rattle virus (TRV) RNA2 sequence to produce a modified TRV RNA2 vector;
   (b) preparing a mixed culture of *Agrobacterium* comprising *Agrobacterium* containing a vector comprising a TRV RNA1 sequence and *Agrobacterium* containing the modified TRV RNA2 vector;
   (c) introducing the mixed culture of *Agrobacterium* into plant tissue of *Jatropha* by vacuum infiltration to produce infected *Jatropha* plants; and
   (d) growing the infected *Jatropha* plants for a sufficient time to produce systemic TRV infection in the infected *Jatropha* plants and to induce gene silencing of the desired gene.

2. A method of analyzing gene function in *Jatropha* comprising
   (a) inserting a nucleic acid comprising a sequence of a first candidate gene the function of which is to be analyzed into a vector comprising a tobacco rattle virus (TRV) RNA2 sequence to produce a modified TRV RNA2 vector;
   (b) preparing a mixed culture of *Agrobacterium* comprising *Agrobacterium* containing a vector comprising a TRV RNA1 sequence and *Agrobacterium* containing the modified TRV RNA2 vector;
   (c) introducing the mixed culture of *Agrobacterium* into plant tissue of *Jatropha* by vacuum infiltration to produce infected *Jatropha* plants;
   (d) growing the infected *Jatropha* plants for a sufficient time to produce systemic TRV infection in the infected *Jatropha* plants and to induce gene silencing of the candidate gene; and
   (e) analyzing the phenotypic effect of the silenced candidate gene on the infected plant.

3. The method of claim 1, wherein the vector comprising TRV RNA2 and the vector comprising TRV RNA1 are synthetic plant vectors.

4. The method of claim 1, wherein the sequence of the first desired gene is the sequence of a sense strand of the gene.

5. The method of claim 1, wherein the sequence of the first desired gene is the sequence of an antisense strand of the gene.

6. The method of claim 1, wherein the nucleic acid further comprises a sequence of a second desired gene to be silenced.

7. The method of claim 6, wherein the second desired gene is a virus resistance gene.

8. The method of claim 7, wherein the virus resistance gene is selected from the group consisting of RNase III Dicer-like 4 (DCL4) gene, RNase III Dicer-like 2 (DCL2) gene, RNase III Dicer-like 3 (DCL3) gene, ARGONAUTE1 (AGO1), ARGONAUTE7 (AGO7), RNA-dependent RNA polymerase 1 (RDR1), RNA-dependent RNA polymerase 6 (RDR6), Suppressor of gene silencing 1 (SGS1), Suppressor of gene silencing 3 (SGS3), and Silencing defective 3 (SDE3).

9. The method of claim 1, wherein the nucleic acid comprises sequences of multiple desired genes to be silenced.

10. The method of claim 1, wherein the desired gene is a candidate gene in fatty acid biosynthesis.

11. The method of claim 10, wherein the desired gene is selected from the group consisting of a β-ketoacyl-acyl carrier protein synthase II (KASII) gene, an acyl-acyl carrier protein thioesterase B (FATB) gene, a stearoyl-acyl carrier protein desaturase (SAD) gene, and a fatty acid desaturase (FAD) gene.

12. The method of claim 1, wherein the desired gene is a candidate transcription factor gene, a candidate gene in small RNA biosynthesis, or a candidate gene in biosynthesis of toxic agents.

13. The method of claim 2, wherein the vector comprising TRV RNA2 and the vector comprising TRV RNA1 are synthetic plant vectors.

14. The method of claim 2, wherein the sequence of the first candidate gene is the sequence of a sense strand of the gene.

15. The method of claim 2, wherein the sequence of the first candidate gene is the sequence of an antisense strand of the gene.

16. The method of claim 2, wherein the nucleic acid further comprises a sequence of a second candidate gene to be silenced.

17. The method of claim 16, wherein the second candidate gene is a virus resistance gene.

18. The method of claim 17, wherein the virus resistance gene is selected from the group consisting of RNase III Dicer-like 4 (DCL4) gene, RNase III Dicer-like 2 (DCL2) gene, RNase III Dicer-like 3 (DCL3) gene, ARGONAUTE1 (AGO1), ARGONAUTE7 (AGO7), RNA-dependent RNA polymerase I (RDR1), RNA-dependent RNA polymerase 6 (RDR6), Suppressor of gene silencing 1 (SGS1), Suppressor of gene silencing 3 (SGS3), and Silencing defective 3 (SDE3).

19. The method of claim 2, wherein the nucleic acid comprises sequences of multiple candidate genes to be silenced.

20. The method of claim 2, wherein the candidate gene is a candidate gene in fatty acid biosynthesis.

21. The method of claim 20, wherein the candidate gene is selected from the group consisting of a β-ketoacyl-acyl carrier protein synthase II (KASII) gene, an acyl-acyl carrier protein thioesterase B (FATB) gene, a stearoyl-acyl carrier protein desaturase (SAD) gene, and a fatty acid desaturase (FAD) gene.

22. The method of claim 2, wherein the candidate gene is a candidate transcription factor gene, or a candidate gene in small RNA biosynthesis, or a candidate gene in biosynthesis of toxic agents.

* * * * *

SEQUENCE LISTING

```
<160> NUMBER OF SEQ ID NOS: 85

<210> SEQ ID NO 1
<211> LENGTH: 17164
<212> TYPE: DNA
<213> ORGANISM: Artificial
<220> FEATURE:
<223> OTHER INFORMATION: sequence of synthetic pSTRV1001 vector

<400> SEQUENCE: 1
ctcgaatttc cccgatcgtt caaacatttg gcaataaagt ttcttaagat tgaatcctgt      60
tgccggtctt gcgatgatta tcatataatt tctgttgaat tacgttaagc atgtaataat     120
taacatgtaa tgcatgacgt tatttatgag atgggttttt atgattagag tcccgcaatt     180
atacatttaa tacgcgatag aaaacaaaat atagcgcgca aactaggata aattatcgcg     240
cgcggtgtca tctatgttac tagatcggga attcactggc cgtcgtttta caacgtcgtg     300
actgggaaaa ccctggcgtt acccaactta atcgccttgc agcacatccc cctttcgcca     360
gctggcgtaa tagcgaagag gcccgcaccg atcgcccttc ccaacagttg cgcagcctga     420
atggcgcccg ctcctttcgc tttcttccct tcctttctcg ccacgttcgc cggctttccc     480
cgtcaagctc taaatcgggg gctcccttta gggttccgat ttagtgcttt acggcacctc     540
gaccccaaaa aacttgattt gggtgatggt tcacgtagtg ggccatcgcc ctgatagacg     600
gtttttcgcc ctttgacgtt ggagtccacg ttctttaata gtggactctt gttccaaact     660
ggaacaacac tcaaccctat ctcgggctat tcttttgatt tataagggat tttgccgatt     720
tcggaaccac catcaaacag gatttttcgcc tgctgggca aaccagcgtg gaccgcttgc     780
tgcaactctc tcagggccag gcggtgaagg gcaatcagct gttgcccgtc tcactggtga     840
aaagaaaaac cacccagta cattaaaaac gtccgcaatg tgttattaag ttgtctaagc     900
gtcaatttgt ttacaccaca atatatcctg ccaccagcca gccaacagct ccccgaccgg     960
```

```
cagctcggca caaaatcacc actcgataca ggcagcccat cagtccggga cggcgtcagc      1020
gggagagccg ttgtaaggcg gcagactttg ctcatgttac cgatgctatt cggaagaacg      1080
gcaactaagc tgccgggttt gaaacacgga tgatctcgcg gagggtagca tgttgattgt      1140
aacgatgaca gagcgttgct gcctgtgatc aaatatcatc tccctcgcag agatccgaat      1200
tatcagcctt cttattcatt tctcgcttaa ccgtgacagg ctgtcgatct tgagaactat      1260
gccgacataa taggaaatcg ctggataaag ccgctgagga agctgagtgg cgctatttct      1320
ttagaagtga acgttgacga tatcaactcc cctatccatt gctcaccgaa tggtacaggt      1380
cggggacccg aagttccgac tgtcggcctg atgcatcccc ggctgatcga ccccagatct      1440
ggggctgaga agcccagta aggaaacaac tgtaggttcg agtcgcgaga tcccccggaa      1500
ccaaaggaag taggttaaac ccgctccgat caggccgagc cacgccaggc cgagaacatt      1560
ggttcctgta ggcatcggga ttggcggatc aaacactaaa gctactggaa cgagcagaag      1620
tcctccggcc gccagttgcc aggcggtaaa ggtgagcaga ggcacgggag gttgccactt      1680
gcgggtcagc acgttccga cgccatgga aaccgccccc gccaggcccg ctgcgacgcc      1740
gacaggatct agcgctgcgt ttggtgtcaa caccaacagc gccacgcccg cagttccgca      1800
aatagccccc aggaccgcca tcaatcgtat cgggctacct agcagagcgg cagagatgaa      1860
cacgaccatc agcggctgca cagcgcctac cgtcgccgcg accccgcccg gcaggcggta      1920
gaccgaaata acaacaagc tccagaatag cgaaatatta agtgcgccga ggatgaagat      1980
gcgcatccac cagattcccg ttggaatctg tcggacgatc atcacgagca ataaacccgc      2040
cggcaacgcc cgcagcagca taccggcgac ccctcggcct cgctgttcgg gctccacgaa      2100
aacgccggac agatgcgcct tgtgagcgtc cttggggccg tcctcctgtt tgaagaccga      2160
cagcccaatg atctcgccgt cgatgtaggc gccgaatgcc acggcatctc gcaaccgttc      2220
agcgaacgcc tccatgggct ttttctcctc gtgctcgtaa acggacccga acatctctgg      2280
agctttcttc agggccgaca atcggatctc gcggaaatcc tgcacgtcgg ccgctccaag      2340
ccgtcgaatc tgagccttaa tcacaattgt caattttaat cctctgttta tcggcagttc      2400
gtagagcgcg ccgtgcgtcc cgagcgatac tgagcgaagc aagtgcgtcg agcagtgccc      2460
gcttgttcct gaaatgccag taaagcgctg gctgctgaac ccccagccgg aactgacccc      2520
acaaggccct agcgtttgca atgcaccagg tcatcattga cccaggcgtg ttccaccagg      2580
ccgctgcctc gcaactcttc gcaggcttcg ccgacctgct cgcgccactt cttcacgcgg      2640
gtggaatccg atccgcacat gaggcggaag gtttccagct tgagcgggta cggctcccgg      2700
tgcgagctga aatagtcgaa catccgtcgg gccgtcggcg acagcttgcg gtacttctcc      2760
catatgaatt tcgtgtagtg gtcgccagca aacagcacga cgatttcctc gtcgatcagg      2820
acctggcaac gggacgtttt cttgccacgg tccaggacgc ggaagcggtg cagcagcgac      2880
accgattcca ggtgcccaac gcggtcggac gtgaagccca tcgccgtcgc ctgtaggcgc      2940
gacaggcatt cctcggcctt cgtgtaatac cggccattga tcgaccagcc caggtcctgg      3000
caaagctcgt agaacgtgaa ggtgatcggc tcgccgatag gggtgcgctt cgcgtactcc      3060
aacacctgct gccacaccag ttcgtcatcg tcggcccgca gctcgacgcc ggtgtaggtg      3120
atcttcacgt ccttgttgac gtggaaaatg accttgtttt gcagcgcctc gcgcgggatt      3180
ttcttgttgc gcgtggtgaa cagggcagag cgggccgtgt cgtttggcat cgctcgcatc      3240
gtgtccggcc acgcgcaat atcgaacaag gaaagctgca tttccttgat ctgctgcttc      3300
gtgtgtttca gcaacgcggc ctgcttggcc tcgctgacct gttttgccag gtcctcgccg      3360
```

```
gcggttttc   gcttcttggt   cgtcatagtt   cctcgcgtgt   cgatggtcat   cgacttcgcc   3420
aaacctgccg   cctcctgttc   gagacgacgc   gaacgctcca   cggcggccga   tggcgcgggc   3480
agggcagggg   gagccagttg   cacgctgtcg   cgctcgatct   tggccgtagc   ttgctggacc   3540
atcgagccga   cggactggaa   ggtttcgcgg   ggcgcacgca   tgacggtgcg   gcttgcgatg   3600
gtttcggcat   cctcggcgga   aaccccgcg    tcgatcagtt   cttgcctgta   tgccttccgg   3660
tcaaacgtcc   gattcattca   ccctccttgc   gggattgccc   cgactcacgc   cggggcaatg   3720
tgcccttatt   cctgatttga   cccgcctggt   gccttggtgt   ccagataatc   caccttatcg   3780
gcaatgaagt   cggtcccgta   gaccgtctgg   ccgtccttct   cgtacttggt   attccgaatc   3840
ttgccctgca   cgaataccag   cgaccccttg   cccaaatact   tgccgtgggc   ctcggcctga   3900
gagccaaaac   acttgatgcg   gaagaagtcg   gtgcgctcct   gcttgtcgcc   ggcatcgttg   3960
cgccacatct   aggtactaaa   acaattcatc   cagtaaaata   taatatttta   ttttctccca   4020
atcaggcttg   atccccagta   agtcaaaaaa   tagctcgaca   tactgttctt   ccccgatatc   4080
ctccctgatc   gaccggacgc   agaaggcaat   gtcataccac   ttgtccgccc   tgccgcttct   4140
cccaagatca   ataaagccac   ttactttgcc   atctttcaca   aagatgttgc   tgtctcccag   4200
gtcgccgtgg   gaaaagacaa   gttcctcttc   gggcttttcc   gtctttaaaa   aatcatacag   4260
ctcgcgcgga   tctttaaatg   gagtgtcttc   ttcccagttt   tcgcaatcca   catcggccag   4320
atcgttattc   agtaagtaat   ccaattcggc   taagcggctg   tctaagctat   tcgtataggg   4380
acaatccgat   atgtcgatgg   agtgaaagag   cctgatgcac   tccgcataca   gctcgataat   4440
cttttcaggg   ctttgttcat   cttcatactc   ttccgagcaa   aggacgccat   cggcctcact   4500
catgagcaga   ttgctccagc   catcatgccg   ttcaaagtgc   aggacctttg   gaacaggcag   4560
cttccttcc   agccatagca   tcatgtcctt   ttcccgttcc   acatcatagg   tggtcccttt   4620
ataccggctg   tccgtcattt   ttaaatatag   gttttcattt   tctcccacca   gcttatatac   4680
cttagcagga   gacattcctt   ccgtatcttt   tacgcagcgg   tattttcga    tcagtttttt   4740
caattccggt   gatattctca   ttttagccat   ttattattc    cttcctcttt   tctacagtat   4800
ttaaagatac   cccaagaagc   taattataac   aagacgaact   ccaattcact   gttccttgca   4860
ttctaaaacc   ttaaatacca   gaaaacagct   ttttcaaagt   tgttttcaaa   gttggcgtat   4920
aacatagtat   cgacggagcc   gattttgaaa   ccacaattat   gggtgatgct   gccaacttac   4980
tgatttagtg   tatgatggtg   tttttgaggt   gctccagtgg   cttctgtgtc   tatcagctgt   5040
ccctcctgtt   cagctactga   cggggtggtg   cgtaacggca   aaagcaccgc   cggacatcag   5100
cgctatctct   gctctcactg   ccgtaaaaca   tggcaactgc   agttcactta   caccgcttct   5160
caacccggta   cgcaccagaa   aatcattgat   atggccatga   atggcgttgg   atgccgggca   5220
acagcccgca   ttatgggcgt   tggcctcaac   acgatttac    gtcacttaaa   aaactcaggc   5280
cgcagtcggt   aacctcgcgc   atacagccgg   gcagtgacgt   catcgtctgc   gcggaaatgg   5340
acgaacagtg   gggctatgtc   ggggctaaat   cgcgccagcg   ctggctgttt   tacgcgtatg   5400
acagtctccg   gaagacggtt   gttgcgcacg   tattcggtga   acgcactatg   gcgacgctgg   5460
ggcgtcttat   gagcctgctg   tcacccttg    acgtggtgat   atggatgacg   gatggctggc   5520
cgctgtatga   atcccgcctg   aagggaaagc   tgcacgtaat   cagcaagcga   tatacgcagc   5580
gaattgagcg   gcataacctg   aatctgaggc   agcacctggc   acggctggga   cggaagtcgc   5640
tgtcgttctc   aaaatcggtg   gagctgcatg   acaaagtcat   cgggcattat   ctgaacataa   5700
```

-continued

```
aacactatca ataagttgga gtcattaccc aattatgata gaatttacaa gctataaggt    5760
tattgtcctg ggtttcaagc attagtccat gcaagttttt atgctttgcc cattctatag    5820
atatattgat aagcgcgctg cctatgcctt gcccctgaa  atccttacat acggcgatat    5880
cttctatata aaagatatat tatcttatca gtattgtcaa tatattcaag gcaatctgcc    5940
tcctcatcct cttcatcctc ttcgtcttgg tagcttttta aatatggcgc ttcatagagt    6000
aattctgtaa aggtccaatt ctcgttttca tacctcggta taatcttacc tatcacctca    6060
aatggttcgc tgggtttatc gcaccccga  acacgagcac ggcacccgcg accactatgc    6120
caagaatgcc caaggtaaaa attgccggcc ccgccatgaa gtccgtgaat gccccgacgg    6180
ccgaagtgaa gggcaggccg ccacccaggc cgccgccctc actgcccggc acctggtcgc    6240
tgaatgtcga tgccagcacc tgcggcacgt caatgcttcc gggcgtcgcg ctcgggctga    6300
tcgcccatcc cgttactgcc ccgatcccgg caatggcaag gactgccagc gctgccattt    6360
ttggggtgag gccgttcgcg gccgagggc gcagcccctg gggggatggg aggcccgcgt     6420
tagcgggccg ggagggttcg agaaggggg  gcaccccct  tcggcgtgcg cggtcacgcg    6480
cacagggcgc agccctggtt aaaaacaagg tttataaata ttggtttaaa agcaggttaa    6540
aagacaggtt agcggtggcc gaaaaacggg cggaaaccct tgcaaatgct ggattttctg    6600
cctgtggaca gcccctcaaa tgtcaatagg tgcgcccctc atctgtcagc actctgcccc    6660
tcaagtgtca aggatcgcgc ccctcatctg tcagtagtcg cgcccctcaa gtgtcaatac    6720
cgcagggcac ttatccccag gcttgtccac atcatctgtg ggaaactcgc gtaaaatcag    6780
gcgttttcgc cgatttgcga ggctggccag ctccacgtcg ccggccgaaa tcgagcctgc    6840
ccctcatctg tcaacgccgc gccgggtgag tcggcccctc aagtgtcaac gtccgcccct    6900
catctgtcag tgagggccaa gttttccgcg aggtatccac aacgccggcg gccgcggtgt    6960
ctcgcacacg gcttcgacgg cgtttctggc gcgtttgcag ggccatagac ggccgccagc    7020
ccagcggcga gggcaaccag cccggtgagc gtcgcaaagg cgctcggtct tgccttgctc    7080
gtcggtgatg tacttcacca gctccgcgaa gtcgctcttc ttgatggagc gcatggggac    7140
gtgcttggca atcacgcgca ccccccgccc gttttagcgg ctaaaaaagt catggctctg    7200
ccctcgggcg gaccacgccc atcatgacct tgccaagctc gtcctgcttc tcttcgatct    7260
tcgccagcag ggcgaggatc gtggcatcac cgaaccgcgc cgtgcgcggg tcgtcggtga    7320
gccagagttt cagcaggccg cccaggcggc ccaggtcgcc attgatgcgg ccagctcgc    7380 ggacgtgctc atagtccacg acgcccgtga ttttgtagcc ctggccgacg gccagcaggt    7440
aggccgacag gctcatgccg gccgccgccg ccttttcctc aatcgctctt cgttcgtctg    7500
gaaggcagta caccttgata ggtgggctgc ccttcctggt tggcttggtt tcatcagcca    7560
tccgcttgcc ctcatctgtt acgccggcgg tagccggcca gcctcgcaga gcaggattcc    7620
cgttgagcac cgccaggtgc gaataaggga cagtgaagaa ggaacacccg ctcgcgggtg    7680
ggcctacttc acctatcctg cccggctgac gccgttggat acaccaagga aagtctacac    7740 gaacccttg  gcaaaatcct gtatatcgtg cgaaaaagga tggatatacc gaaaaaatcg    7800
ctataatgac cccgaagcag ggttatgcag cggaaaagcg ccacgcttcc cgaagggaga    7860
aaggcggaca ggtatccggt aagcggcagg gtcggaacag gagagcgcac gagggagctt    7920
ccagggggaa acgcctggta tctttatagt cctgtcgggt ttcgccacct ctgacttgag    7980
cgtcgatttt tgtgatgctc gtcagggggg cggagcctat ggaaaaacgc cagcaacgcg    8040
gcctttttac ggttcctggc cttttgctgg ccttttgctc acatgttctt tcctgcgtta    8100
```

```
tcccctgatt ctgtggataa ccgtattacc gcctttgagt gagctgatac cgctcgccgc   8160
agccgaacga ccgagcgcag cgagtcagtg agcgaggaag cggaagagcg ccagaaggcc   8220
gccagagagg ccgagcgcgg ccgtgaggct tggacgctag ggcagggcat gaaaaagccc   8280
gtagcgggct gctacgggcg tctgacgcgg tggaaagggg gaggggatgt tgtctacatg   8340
gctctgctgt agtgagtggg ttgcgctccg gcagcggtcc tgatcaatcg tcacccttc    8400 tcggtccttc aacgttcctg acaacgagcc tccttttcgc caatccatcg acaatcaccg   8460
cgagtccctg ctcgaacgct gcgtccggac cggcttcgtc gaaggcgtct atcgcggccc   8520
gcaacagcgg cgagagcgga gcctgttcaa cggtgccgcc gcgctcgccg gcatcgctgt   8580
cgccggcctg ctcctcaagc acggccccaa cagtgaagta gctgattgtc atcagcgcat   8640
tgacggcgtc cccggccgaa aaacccgcct cgcagaggaa gcgaagctgc gcgtcggccg   8700
tttccatctg cggtgcgccc ggtcgcgtgc cggcatggat gcgcgcgcca tcgcggtagg   8760
cgagcagcgc ctgcctgaag ctgcgggcat tcccgatcag aaatgagcgc cagtcgtcgt   8820
cggctctcgg caccgaatgc gtatgattct ccgccagcat ggcttcggcc agtgcgtcga   8880
gcagcgcccg cttgttcctg aagtgccagt aaagcgccgg ctgctgaacc cccaaccgtt   8940
ccgccagttt gcgtgtcgtc agaccgtcta cgccgacctc gttcaacagg tccagggcgg   9000
cacggatcac tgtattcggc tgcaactttg tcatgcttga cactttatca ctgataaaca   9060
taatatgtcc accaacttat cagtgataaa gaatccgcgc gttcaatcgg accagcggag   9120
gctggtccgg aggccagacg tgaaacccaa catacccctg atcgtaattc tgagcactgt   9180
cgcgctcgac gctgtcggca tcggcctgat tatgccggtg ctgccgggcc tcctgcgcga   9240
tctggttcac tcgaacgacg tcaccgccca ctatggcatt ctgctggcgc tgtatgcgtt   9300
ggtgcaattt gcctgcgcac ctgtgctggg cgcgctgtcg gatcgtttcg gcggcggcc    9360 aatcttgctc gtctcgctgg ccggcgccag atctggggaa ccctgtggtt ggcatgcaca   9420
tacaaatgga cgaacggata aaccttttca cgccctttta aatatccgat tattctaata   9480
aacgctcttt tctcttaggt ttacccgcca atatatcctg tcaaacactg atagtttaaa   9540
ctgaaggcgg gaaacgacaa tctgctagcg gtcaacatgg tggagcacga cactctcgtc   9600
tactccaaga atatcaaaga tacagtctca gaagaccaga gggctattga acttttcaa    9660 caaagggtaa tatcgggaaa cctcctcgga ttccattgcc cagctatctg tcacttcatc   9720
gaaaggacag tagaaaagga agatggcttc tacaaatgcc atcattgcga taaaggaaag   9780
gctatcgttc aagatgcctc taccgacagt ggtcccaaag atggacccc  cccacgagg    9840 aacatcgtgg aaaaagaaga cgttccaacc acgtcttcaa agcaagtgga ttgatgtgat   9900
ggtcaacatg gtggagcacg acactctcgt ctactccaag aatatcaaag atacagtctc   9960
agaagaccag agggctattg acttttca acaaagggta atatcgggaa acctcctcgg     10020
attccattgc ccagctatct gtcacttcat cgaaaggaca gtagaaaagg aagatggctt   10080
ctacaaatgc catcattgcg ataaaggaaa ggctatcgtt caagatgcct ctaccgacag   10140
tggtcccaaa gatggacccc cacccacgag gaacatcgtg gaaaagaag acgttccaac    10200 cacgtcttca aagcaagtgg attgatgtga tatctccact gacgtaaggg atgacgcaca   10260
atcccactat ccttcgcaag acccttcctc tatataagga agttcatttc atttggagag   10320
gataaaacat ttcaatccct tgaacgcggt agaacgtgct aattggattt tggtgagaac   10380
gcggtagaac gtacttatca cctacagttt tattttgttt ttcttttttgg tttaatctat   10440
```

```
ccagcttagt accgagtggg ggaaagtgac tggtgtgcct aaaaccttt  ctttgatact  10500
ttgtaaaaat acatacagat acaatggcga acggtaactt caagttgtct caattgctca  10560
atgtggacga gatgtctgct gagcagagga gtcatttctt tgacttgatg ctgactaaac  10620
ctgattgtga gatcgggcaa atgatgcaaa gagttgttgt tgataaagtc gatgacatga  10680
ttagagaaag aaagactaaa gatccagtga ttgttcatga agttctttct cagaaggaac  10740
agaacaagtt gatggaaatt tatcctgaat tcaatatcgt gttaaagac  gacaaaaaca  10800
tggttcatgg gtttgcggct gctgagcgaa aactacaagc tttattgctt ttagatagag  10860
ttcctgctct gcaagaggtg gatgacatcg gtggtcaatg gtcgttttgg gtaactagag  10920
gtgagaaaag gattcattcc tgttgtccaa atctagatat tcgggatgat cagagagaaa  10980
tttctcgaca gatatttctt actgctattg gtgatcaagc tagaagtggt aagagacaga  11040
tgtcggagaa tgagctgtgg atgtatgacc aatttcgtga aaatattgct gcgcctaacg  11100
cggttaggtg caataataca tatcagggtt gtacatgtag gggttttctct gatggtaaga  11160
agaaaggcgc gcagtatgcg atagctcttc acagcctgta tgacttcaag ttgaaagact  11220
tgatggctac tatggttgag aagaaaacta aagtggttca tgctgctatg cttttgctc   11280
ctgaaagtat gttagtggac gaaggtccat taccttctgt tgacggttac tacatgaaga  11340
agaacgggaa gatctatttc ggttttgaga aagatccttc ctttcttac  attcatgact  11400
gggaagagta caagaagtat ctactgggga agccagtgag ttaccaaggg aatgtgttct  11460
acttcgaacc gtggcaggtg agaggagaca caatgctttt ttcgatctac aggatagctg  11520
gagttccgag gaggtctcta tcatcgcaag agtactaccg aagaatatat atcagtagat  11580
gggaaaacat ggttgttgtc ccaattttcg atctggtcga atcaacgcga gagttggtca  11640
agaaagacct gtttgtagag aaacaattca tggacaagtg tttggattac atagctaggt  11700
tatctgacca gcagctgacc ataagcaatg ttaaatcata cttgagttca ataattggg   11760
tcttattcat aaacggggcg gccgtgaaga acaagcaaag tgtagattct cgagatttac  11820
agttgttggc tcaaactttg ctagtgaagg aacaagtggc gagacctgtc atgagggagt  11880
tgcgtgaagc aattctgact gagacgaaac ctatcacgtc attgactgat gtgctgggtt  11940
taatatcaag aaaactgtgg aagcagtttg ctaacaagat cgcagtcggc ggattcgttg  12000
gcatggttgg tactctaatt ggattctatc caaagaaggt actaacctgg gcgaaggaca  12060
caccaaatgg tccagaacta tgttacgaga actcgcacaa aaccaaggtg atagtatttc  12120
tgagtgttgt gtatgccatt ggaggaatca cgcttatgcg tcgagacatc cgagatggac  12180
tggtgaaaaa actatgtgat atgtttgata tcaaacgggg ggcccatgtc ttagacgttg  12240
agaatccgtg ccgctattat gaaatcaacg atttctttag cagtctgtat tcggcatctg  12300
agtccggtga gaccgtttta ccagatttat ccgaggtaaa agccaagtct gataagctat  12360
tgcagcagaa gaaagaaatc gctgacgagt ttctaagtgc aaaattctct aactattctg  12420
gcagttcggt gagaacttct ccaccatcgg tggtcggttc atctcgaagc ggactgggtc  12480
tgttgttgga agacagtaac gtgctgaccc aagctagagt tggagtttca agaaaggtag  12540
acgatgagga gatcatggag cagtttctga gtggtcttat tgacactgaa gcagaaattg  12600
acgaggttgt tccagccttt tcagctgaat gtgaaagagg ggaaacaagc ggtacaaagg  12660
tgttgtgtaa acctttaacg ccaccaggat ttgagaacgt gttgccagct gtcaaacctt  12720
tggtcagcaa aggaaaaacg gtcaaacgtg tcgattactt ccaagtgatg ggaggtgaga  12780
gattaccaaa aaggccggtt gtcagtggag acgattctgt ggacgctaga agagagtttc  12840
```

```
tgtactactt agatgcggag agagtcgctc aaaatgatga aattatgtct ctgtatcgtg    12900
actattcgag aggagttatt cgaactggag gtcagaatta cccgcacgga ctgggagtgt    12960
gggatgtgga gatgaagaac tggtgcatac gtccagtggt cactgaacat gcttatgtgt    13020
tccaaccaga caaacgtatg gatgattggt cgggatactt agaagtggct gtttgggaac    13080
gaggtatgtt ggtcaacgac ttcgcggtcg aaaggatgag tgattatgtc atagtttgcg    13140
atcagacgta tctttgcaat aacaggttga tcttggacaa tttaagtgcc ctggatctag    13200
gaccagttaa ctgttctttt gaattagttg acggtgtacc tggttgtggt aagtcgacaa    13260
tgattgtcaa ctcagctaat ccttgtgtcg atgtggttct ctctactggg agagcagcaa    13320
ccgacgactt gatcgagaga ttcgcgagca aaggttttcc atgcaaattg aaaaggagag    13380
tgaagacggt tgattctttt ttgatgcatt gtgttgatgg ttcttttaacc ggagacgtgt    13440 tgcatttcga tgaagctctc atggcccatg ctggtatggt gtacttttgc gctcagatag    13500
ctggtgctaa acgatgtatc tgtcaaggag atcagaatca aatttctttc aagcctaggg    13560
tatctcaagt tgatttgagg ttttctagtc tggtcggaaa gtttgacatt gttacagaaa    13620
aaagagaaac ttacagaagt ccagcagatg tggctgccgt attgaacaag tactatactg    13680
gagatgtcag aacacataac gcgactgcta attcgatgac ggtgaggaag attgtgtcta    13740
aagaacaggt ttcttttgaag cctggtgctc agtacataac tttccttcag tctgagaaga    13800
aggagttggt aaatttgttg gcattgagga aagtggcagc taaagtgagt acagtacacg    13860
agtcgcaagg agagacattc aaagatgtag tcctagtcag gacgaaacct acggatgact    13920
caatcgctag aggtcgggag tacttaatcg tggcgttgtc gcgtcacaca caatcacttg    13980
tgtatgaaac tgtgaaagag gacgatgtaa gcaaagagat cagggaaagt gccgcgctta    14040
cgaaggcggc tttggcaaga ttttttgtta ctgagaccgt cttatgacgg tttcggtcta    14100
ggtttgatgt ctttagacat catgaagggc cttgcgccgt tccagattca ggtacgatta    14160
cggacttgga gatgtggtac gacgctttgt ttccgggaaa ttcgttaaga gactcaagcc    14220
tagacgggta tttggtggca acgactgatt gcaatttgcg attagacaat gttacgatca    14280
aaagtggaaa ctggaaagac aagtttgctg aaaaagaaac gtttctgaaa ccggttattc    14340
gtactgctat gcctgacaaa aggaagacta ctcagttgga gagtttgtta gcattgcaga    14400
aaaggaacca agcggcaccc gatctacaag aaaatgtgca cgcaacagtt ctaatcgaag    14460
agacgatgaa gaagttgaaa tctgttgtct acgatgtggg aaaaattcgg gctgatccta    14520
ttgtcaatag agctcaaatg gagagatggt ggagaaatca agcacagcg gtacaggcta    14580 aggtagtagc agatgtgaga gagttacatg aaatagacta ttcgtcttac atgtatatga    14640
tcaaatctga cgtgaaacct aagactgatt taacaccgca atttgaatac tcagctctac    14700
agactgttgt gtatcacgag aagttgatca actcgttgtt cggtccaatt ttcaaagaaa    14760
ttaatgaacg caagttggat gctatgcaac cacattttgt gttcaacacg agaatgacat    14820
cgagtgattt aaacgatcga gtgaagttct aaaatacgga agcggcttac gactttgttg    14880
agatagacat gtctaaattc gacaagtcgg caaatcgctt ccatttacaa ctgcagctgg    14940
agatttacag gttatttggg ctagatgagt gggcggcctt cctttgggag gtgtcgcaca    15000
ctcaaactac tgtgagagat attcaaaatg gtatgatggc gcatatttgg taccaacaaa    15060
agagtggaga tgctgatact tataatgcaa attcagatag aacactgtgt gcactcttgt    15120
ctgaattacc attggagaaa gcagtcatgg ttacatatgg aggagatgac tcactgattg    15180
```

```
cgtttcctag aggaacgcag tttgttgatc cgtgtccaaa gttggctact aagtggaatt   15240
tcgagtgcaa gattttttaag tacgatgtcc caatgttttg tgggaagttc ttgcttaaga   15300
cgtcatcgtg ttacgagttc gtgccagatc cggtaaaagt tctgacgaag ttggggaaaa   15360
agagtataaa ggatgtgcaa catttagccg agatctacat ctcgctgaat gattccaata   15420
gagctcttgg gaactacatg gtggtatcca aactgtccga gtctgtttca gaccggtatt   15480
tgtacaaagg tgattctgtt catgcgcttt gtgcgctatg gaagcatatt aagagttta   15540 cagctctgtg tacattattc cgagacgaaa acgataagga attgaacccg gctaaggttg   15600
attggaagaa ggcacagaga gctgtgtcaa acttttacga ctggtaatat ggaagacaag   15660
tcattggtca ccttgaagaa gaagactttc gaagtctcaa aattctcaaa tctaggggcc   15720
attgaattgt tgtggacgg taggaggaag agaccgaagt attttcacag aagaagagaa   15780
actgtcctaa atcatgttgg tgggaagaag agtgaacaca agttagacgt ttttgaccaa   15840
agggattaca aaatgattaa atcttacgcg tttctaaaga tagtaggtgt acaactagtt   15900
gtaacatcac atctacctgc agatacgcct gggttcattc aaatcgatct gttggattcg   15960
agacttactg agaaaagaaa gagaggaaag actattcaga gattcaaagc tcgagcttgc   16020
gataactgtt cagttgcgca gtacaaggtt gaatacagta tttccacaca ggagaacgta   16080
cttgatgtct ggaaggtggg ttgtatttct gagggcgttc cggtctgtga cggtacatac   16140
cctttcagta tcgaagtgtc gctaatatgg gttgctactg attcgactag gcgcctcaat   16200
gtggaagaac tgaacagttc ggattacatt gaaggcgatt ttaccgatca agaggttttc   16260
ggtgagttca tgtctttgaa acaagtggag atgaagacga ttgaggcgaa gtacgatggt   16320
ccttacagac cagctactac tagacctaag tcattattgt caagtgaaga tgttaagaga   16380
gcgtctaata agaaaaactc gtcttaatgc ataaagaaat ttattgtcaa tatgacgtgt   16440
gtactcaagg gttgtgtgaa tgaagtcact gttcttggtc acgagacgtg tagtatcggt   16500
catgctaaca aattgcgaaa gcaagttgct gacatggttg gtgtcacacg taggtgtgcg   16560
gaaaataatt gtggatggtt tgtctgtgtt gttatcaatg attttacttt tgatgtgtat   16620
aattgttgtg gccgtagtca ccttgaaaag tgtcgtaaac gtgttgaaac aagaaatcga   16680
gaaatttgga acaaattcg acgaaatcaa gctgaaaaca tgtctgcgac agctaaaaag   16740
tctcataatt cgaagacctc taagaagaaa ttcaaagagg acagaagaatt tgggacacca   16800 aaagattttt taagagatga tgttcctttc gggattgatc gtttgtttgc tttttgattt   16860
tattttatat tgttatctgt ttctgtgtat agactgtttg agattggcgc ttggccgact   16920
cattgtctta ccatagggga acggactttg tttgtgttgt tattttattt gtattttatt   16980
aaaattctca atgatctgaa aaggcctcga ggctaagaga ttattggggg gtgagtaagt   17040
acttttaaag tgatgatggt tacaaaggca aaagggtaa aaccctcgc ctacgtaagc   17100 gttattacgc ccgtctgtac ttatatcagt acactgacga gtccctaaag gacgaaacgg   17160
gccc                                                                17164
```

<210> SEQ ID NO 2
<211> LENGTH: 2915
<212> TYPE: DNA
<213> ORGANISM: Artificial
<220> FEATURE:
<223> OTHER INFORMATION: sequence of synthetic sTRV2

<400> SEQUENCE: 2

```
aagcttggtc aacatggtgg agcacgacac tctcgtctac tccaagaata tcaaagatac      60
```

```
agtctcagaa gaccagaggg ctattgagac ttttcaacaa agggtaatat cgggaaacct    120
cctcggattc cattgcccag ctatctgtca cttcatcgaa aggacagtag aaaaggaaga    180
tggcttctac aaatgccatc attgcgataa aggaaaggct atcgttcaag atgcctctac    240
cgacagtggt cccaaagatg gaccccacc cacgaggaac atcgtggaaa agaagacgt     300 tccaaccacg tcttcaaagc aagtggattg atgtgatggt caacatggtg gagcacgaca    360
ctctcgtcta ctccaagaat atcaaagata cagtctcaga agaccagagg gctattgaga    420
cttttcaaca agggtaata tcgggaaacc tcctcggatt ccattgccca gctatctgtc      480
acttcatcga aggacagta gaaaggaag atggcttcta caaatgccat cattgcgata     540
aaggaaaggc tatcgttcaa gatgcctcta ccgacagtgg tcccaaagat ggaccccac     600 ccacgaggaa catcgtggaa aagaagacg ttccaaccac gtcttcaaag caagtggatt     660
gatgtgatat ctccactgac gtaagggatg acgcacaatc ccactatcct tcgcaagacc    720
cttcctctat ataaggaagt tcatttcatt tggagaggat aaaacattgc acctatggtg    780
ttgccctggc tggggtatgt cagtgatcgc agtagaatgt actaattgac aagttggaga    840
atacggtaga acgtccttat ccaacacagc ctttatccct ctccctgacg aggttttttgt   900 cagtgtaata tttcttttg aactatccag cttagtaccg tacgggaaag tgactggtgt     960
gcttatcttt gaaatgttac tttgggtttc ggttctttag gttagtaaga aagcacttgt    1020
cttctcatac aaaggaaaac ctgagacgta tcgcttacga aagtagcaat gaaagaaagg    1080
tggtggtttt aatcgctacc gcaaaaacga tggggtcgtt ttaattaact tctcctacgc    1140
aagcgtctaa acggacgttg gggttttgct agtttcttta gagaaaacta gctaagtctt    1200
taatgttatc attagagatg gcataaatat aatacttgtg tctgctgata agatcatttt    1260
aatttggacg attagacttg ttgaactaca ggttactgaa tcacttgcgc taatcaacat    1320
gggagatatg tacgatgaat catttgacaa gtcgggcggt cctgctgact tgatggacga    1380
ttcttgggtg gaatcagttt cgtggaaaga tctgttgaag aagttacaca gcataaaatt    1440
tgcactacag tctggtagag atgagatcac tgggttacta gcggcactga atagacagtg    1500
tccttattca ccatatgagc agtttccaga taagaaggtg tatttccttt tagactcacg    1560
ggctaacagt gctcttggtg tgattcagaa cgcttcagcg ttcaagagac gagctgatga    1620
gaagaatgca gtggcgggtg ttacaaatat tcctgcgaat ccaaacacaa cggttacgac    1680
gaaccaaggg agtactacta ctaccaaggc gaacactggc tcgactttgg aagaagactt    1740
gtacacttat tacaaattcg atgatgcctc tacagctttc cacaaatctc taacttcgtt    1800
agagaacatg gagttgaaga gttattaccg aaggaacttt gagaaagtat tcgggattaa    1860
gtttggtgga gcagctgcta gttcatctgc accgcctcca gcgagtggag gtccgatacg    1920
tcctaatccc tagggattta aggacgtgaa ctctgttgag atctctgtga aattcagagg    1980
gtgggtgata ccatattcac tgatgccatt agcgacatct aaatagggct aattgtgact    2040
aatttgaggg aatttccttt accattgacg tcagtgtcgt tggtagcatt tgagtttcgc    2100
aatgcacgaa ttacttagga agtggcttga cgacactaat gtgttattgt tagataatgg    2160
tttggtggtc aaggtacgta gtagagtccc acatattcgc acgtatgaag taattggaaa    2220
gttgtcagtt tttgataatt cactgggaga tgatacgctg tttgagggaa agtagagaa    2280 cgtatttgtt tttatgttca ggcggttctt gtgtgtcaac aaagatggac attgttactc    2340
aaggaagcac gatgagcttt attattacgg acgagtggac ttagattctg tgagtaaggt    2400
```

-continued

```
taccgaattc tctagaaggc ctccatgggg atccggtacc gagctcacgc gtctcgaggc    2460
ccgggcatgt cccgaagaca ttaaactacg gttctttaag tagatccgtg tctgaagttt    2520
taggttcaat ttaaacctac gagattgaca ttctcgactg atcttgattg atcggtaagt    2580
cttttgtaat ttaattttct ttttgatttt attttaaatt gttatctgtt tctgtgtata    2640
gactgtttga gatcggcgtt tggccgactc attgtcttac catagggaa cggactttgt     2700 ttgtgttgtt attttatttg tattttatta aaattctcaa cgatctgaaa aagcctcgcg    2760
gctaagagat tgttgggggg tgagtaagta cttttaaagt gatgatggtt acaaaggcaa    2820
aaggggtaaa acccctcgcc tacgtaagcg ttattacgcc cgtctgtact tatatcagta    2880
cactgacgag tccctaaagg acgaaacggg ttaac                               2915
```

<210> SEQ ID NO 3
<211> LENGTH: 25
<212> TYPE: DNA
<213> ORGANISM: Artificial
<220> FEATURE:
<223> OTHER INFORMATION: PCR primer

<400> SEQUENCE: 3

```
ccttgtgtgg atccagtttt caagg                                          25
```

<210> SEQ ID NO 4
<211> LENGTH: 30
<212> TYPE: DNA
<213> ORGANISM: Artificial
<220> FEATURE:
<223> OTHER INFORMATION: PCR primer

<400> SEQUENCE: 4

```
ccctccaaaa caccgtacgt cagatctatt                                     30
```

<210> SEQ ID NO 5
<211> LENGTH: 28
<212> TYPE: DNA
<213> ORGANISM: Artificial
<220> FEATURE:
<223> OTHER INFORMATION: PCR primer

<400> SEQUENCE: 5

```
tctagaccat ggattccagc cacgttgc                                       28
```

<210> SEQ ID NO 6
<211> LENGTH: 28
<212> TYPE: DNA
<213> ORGANISM: Artificial
<220> FEATURE:
<223> OTHER INFORMATION: PCR primer

<400> SEQUENCE: 6

```
ccaactcatg ttctaacgac tccctagg                                       28
```

<210> SEQ ID NO 7
<211> LENGTH: 613
<212> TYPE: DNA
<213> ORGANISM: Jatropha curcas

<400> SEQUENCE: 7

```
tcagcaatct tgtactcaac cacaacagga agttctgaag acaagctgat tgtaactata    60
tttgacaatg gcgtcgcctt ggtgaaggag ttcatgtacc ttaatgcaaa tgtcaacgac    120
acaggctcat tcatctctat gattgttgcc tcttcaggct tgtctactgt tgtattctgc    180
```

```
ctgagaacaa catttgcagc cccaatatcg cctcttgtgg agaatttgac tccttccttt    240
gaaacagaga tcacaacagt atcaccaatg cttgcaagat ctctacaaat tttggcaaac    300
tcagctgatg gcatcctgat aatggcatga tattctgcct ctgggattcc aaggtgttca    360
ctgtcaatgt ccatcagttt catctcaaaa tctgaaatct tatcttgtgt gggactttca    420
aacatgaaag tgacagagtc gctgccgtcg tcagccttga tggtgatgat atcatcattt    480
ccggagcact ttaacatctt agccatgtta tcaagattca tacccatgga aaggttacgg    540
tcacagcgat agtgctcaaa gccctccgct ctaaggagaa gagacaccaa agcaacgtgg    600
ctggaatcca tgg                                                      613

<210> SEQ ID NO 8
<211> LENGTH: 28
<212> TYPE: DNA
<213> ORGANISM: Artificial
<220> FEATURE:
<223> OTHER INFORMATION: degenerate PCR primer
<220> FEATURE:
<221> NAME/KEY: misc_feature
<222> LOCATION: (23)..(23)
<223> OTHER INFORMATION: n is a, c, g or t

<400> SEQUENCE: 8
cccggggcma tgtcaaaggc dknaaktt                                       28

<210> SEQ ID NO 9
<211> LENGTH: 29
<212> TYPE: DNA
<213> ORGANISM: Artificial
<220> FEATURE:
<223> OTHER INFORMATION: degenerate PCR primer

<400> SEQUENCE: 9
tawttmcavg tmtataccaa actcctagg                                      29

<210> SEQ ID NO 10
<211> LENGTH: 38
<212> TYPE: DNA
<213> ORGANISM: Artificial
<220> FEATURE:
<223> OTHER INFORMATION: PCR primer

<400> SEQUENCE: 10
aattctctag aggccagaga aagtaagttt gcaattgg                            38

<210> SEQ ID NO 11
<211> LENGTH: 40
<212> TYPE: DNA
<213> ORGANISM: Artificial
<220> FEATURE:
<223> OTHER INFORMATION: PCR primer

<400> SEQUENCE: 11
aaaggactac tttatagacg actagtctcc taggttaagt                          40

<210> SEQ ID NO 12
<211> LENGTH: 786
<212> TYPE: DNA
<213> ORGANISM: Jatropha curcas

<400> SEQUENCE: 12
ggccagagaa agttaagttt gcaattggac ttcttccagc aatgcttggt ggacaagcat    60
```

```
atgttgaggc tcaagatggt ttgaccgttc aagaatggat gagaaagcag ggggttcctg      120
atcgagtgac taaagaggtg tttatcgcca tgtcaaaggc acttaacttt attaacccag      180
atgaactttc gatgcaatgt atattgatag cactgaaccg atttcttcag gagaaacatg      240
gttcaaaaat ggcttcctta gatggaaacc ccccggagag actctgtatg ccaattgttg      300
atcatattca atcattggga ggtgaagtcc ggctgaattc acgaataaag aaagttgagc      360
taaataatga tgggacagtg agaagcttct tactgaatac tggggacgta attgaagcag      420
atgcttatgt gtttgccact ccagttgata tcctgaagct tcttctgcct gatagctgga      480
aagagattcc gtacttcaac aaattggaaa aattagttgg agttcctgtt attaatgttc      540
acatatggtt tgataggaaa ctaaagaatg catatgatca cctacttttc agcagaagtt      600
cccttctgag tgtttatgct gacatgtcgg tgacgtgtaa ggaatattat agtccaaatc      660
agtcgatgct ggagttagtt tttgcgcctg cagaagaatg gatctcacgt agtgactcag      720
aaatcatcaa tgctacaatg aaggaacttg caaaactctt tcctgatgaa atatctgctg      780
atcaga                                                                 786

<210> SEQ ID NO 13
<211> LENGTH: 31
<212> TYPE: DNA
<213> ORGANISM: Artificial
<220> FEATURE:
<223> OTHER INFORMATION: PCR primer

<400> SEQUENCE: 13
tctagagaag arggrgagct ccggccccag c                                      31

<210> SEQ ID NO 14
<211> LENGTH: 29
<212> TYPE: DNA
<213> ORGANISM: Artificial
<220> FEATURE:
<223> OTHER INFORMATION: PCR primer

<400> SEQUENCE: 14
ccaaacgaac agtaactctt taacctagg                                         29

<210> SEQ ID NO 15
<211> LENGTH: 44
<212> TYPE: DNA
<213> ORGANISM: Artificial
<220> FEATURE:
<223> OTHER INFORMATION: PCR primer

<400> SEQUENCE: 15
aatccatcta gaagagaggg caatttctat ttccacccgg cacg                        44

<210> SEQ ID NO 16
<211> LENGTH: 34
<212> TYPE: DNA
<213> ORGANISM: Artificial
<220> FEATURE:
<223> OTHER INFORMATION: PCR primer

<400> SEQUENCE: 16
catgatttaa cttctcttac ttatctagat ataa                                   34

<210> SEQ ID NO 17
<211> LENGTH: 696
<212> TYPE: DNA
<213> ORGANISM: Jatropha curcas
```

<400> SEQUENCE: 17

```
agagagggca atttctattt ccacccggca cgatttattt tgattggctc tggaaatcct      60
gaagaggggg agctccggcc acagctgctt gatagatttg gaatgcatgc acaagttgga     120
actgtaaggg atgcagagct tagagtgaag attgtggaag aaagagctcg gtttgacaaa     180
aaccctaagg aattccgcga ttcttacaag acagagcaag agaagctgca gcagcaaatt     240
tctgcagcta gaacttctct ttcttctgtg cagatagatc atgacctcaa ggtaaaaatc     300
tcgaaggttt gtgcagagct gaatgttgat gggttgagag agacattgt gactaacaga      360
gctgcaaaag ctttagcagc tctgaaggga agagataagg tcactgcaga ggatgttgct     420
actgtcatcc ccaactgttt aagacaccgt cttaggaagg atccattgga gtcaatagac     480
tcgggtttac ttgtcattga aaaattctat gaagttttta gctgaggata ccatttagat     540
gcctctgtaa ttttgttgac tcataattga atctatttgc tgttttttgtc gcttttgttt    600
ttcatgttat cttagttaaa tattctgcaa atgtaaagcc atcgttccgg tttttattga     660
ggatcttgta ctaaattgaa gagaatgaat agatcc                               696
```

<210> SEQ ID NO 18
<211> LENGTH: 32
<212> TYPE: DNA
<213> ORGANISM: Artificial
<220> FEATURE:
<223> OTHER INFORMATION: PCR primer

<400> SEQUENCE: 18

```
gcgtctagag gaaagatgag gatattacag gg                                    32
```

<210> SEQ ID NO 19
<211> LENGTH: 25
<212> TYPE: DNA
<213> ORGANISM: Artificial
<220> FEATURE:
<223> OTHER INFORMATION: PCR primer

<400> SEQUENCE: 19

```
cggtttacga agagaatcta gaaat                                            25
```

<210> SEQ ID NO 20
<211> LENGTH: 32
<212> TYPE: DNA
<213> ORGANISM: Artificial
<220> FEATURE:
<223> OTHER INFORMATION: PCR primer

<400> SEQUENCE: 20

```
aactttctag accaccattc acacttggtc ag                                    32
```

<210> SEQ ID NO 21
<211> LENGTH: 33
<212> TYPE: DNA
<213> ORGANISM: Artificial
<220> FEATURE:
<223> OTHER INFORMATION: PCR primer

<400> SEQUENCE: 21

```
gtattgtaat gtctgtgagt accctaggtt att                                   33
```

<210> SEQ ID NO 22
<211> LENGTH: 29
<212> TYPE: DNA

```
<213> ORGANISM: Artificial
<220> FEATURE:
<223> OTHER INFORMATION: PCR primer

<400> SEQUENCE: 22
aactttctag acgactcact atagggcga                                           29

<210> SEQ ID NO 23
<211> LENGTH: 29
<212> TYPE: DNA
<213> ORGANISM: Artificial
<220> FEATURE:
<223> OTHER INFORMATION: PCR primer

<400> SEQUENCE: 23
taccttgaga tgttgaaccc taggttatt                                           29

<210> SEQ ID NO 24
<211> LENGTH: 711
<212> TYPE: DNA
<213> ORGANISM: Jatropha curcas

<400> SEQUENCE: 24
cgactcacta tagggcgaat tgggcccgac gtcgcatgct cccggccgcc atggtacagg          60
ccattacggc cggggcattg ggattttcgc tgcaacttat gtgctctatc agattgccat         120
ggcaaaaggg ttagcttggc tgatatctat ttatgggata ccattgctta ttgttaatgc         180
ttttcttgtg acaatcacat atttgcggca cactcaccct gcattgccac actatgactc         240
gtccgaatgg gattggctcc ggggagcttt gtcgacagtg gatagagatt atggggtgtt         300
gaataaggtt ttccataata ttacagacac tcatgtaacc caccatctct tctctacaat         360
gcctcattat catgcaatgg aggccactaa agcaatcaag cctatattgg gcgagtatta         420
tcagtttgat ggcactccga ttcttatggc gctctggatg gaggccaagg agtgcctgtt         480
tgtcgagcca gaagagggag gtcccaaccg aggagttctc tggtatggaa ataagtatta         540
agagctataa tatgtggttt ggccttcaga gaagttaatt agaataacta tgcagagagt         600
gtgaatgtag tatagatgtt agtaatggag aagaaaaact atatgcgtag tagctttctt         660
tacgggaaag tggtgtttga gttatgtccg tttatggaac tctacaactt g                 711

<210> SEQ ID NO 25
<211> LENGTH: 29
<212> TYPE: DNA
<213> ORGANISM: Artificial
<220> FEATURE:
<223> OTHER INFORMATION: PCR primer

<400> SEQUENCE: 25
aactttctag aaccatcttc agacagtgc                                           29

<210> SEQ ID NO 26
<211> LENGTH: 29
<212> TYPE: DNA
<213> ORGANISM: Artificial
<220> FEATURE:
<223> OTHER INFORMATION: PCR primer

<400> SEQUENCE: 26
caagtaacac tgatgggacc taggttatt                                           29

<210> SEQ ID NO 27
<211> LENGTH: 20
```

```
<212> TYPE: DNA
<213> ORGANISM: Artificial
<220> FEATURE:
<223> OTHER INFORMATION: PCR primer

<400> SEQUENCE: 27
tggatccaca gtaggctata                                                   20

<210> SEQ ID NO 28
<211> LENGTH: 30
<212> TYPE: DNA
<213> ORGANISM: Artificial
<220> FEATURE:
<223> OTHER INFORMATION: PCR primer

<400> SEQUENCE: 28
gttacacttc atgtaaccga ccatggttaa                                        30

<210> SEQ ID NO 29
<211> LENGTH: 22
<212> TYPE: DNA
<213> ORGANISM: Artificial
<220> FEATURE:
<223> OTHER INFORMATION: PCR primer

<400> SEQUENCE: 29
atctctagat gaatgggctg ag                                                22

<210> SEQ ID NO 30
<211> LENGTH: 29
<212> TYPE: DNA
<213> ORGANISM: Artificial
<220> FEATURE:
<223> OTHER INFORMATION: PCR primer

<400> SEQUENCE: 30
cgagtcctaa tgcaaacatc tagatttgt                                         29

<210> SEQ ID NO 31
<211> LENGTH: 28
<212> TYPE: DNA
<213> ORGANISM: Artificial
<220> FEATURE:
<223> OTHER INFORMATION: PCR primer

<400> SEQUENCE: 31
aatatctaga cgccacctct attgaagc                                          28

<210> SEQ ID NO 32
<211> LENGTH: 28
<212> TYPE: DNA
<213> ORGANISM: Artificial
<220> FEATURE:
<223> OTHER INFORMATION: PCR primer

<400> SEQUENCE: 32
cgagtcgccg aacctcatcc taggtata                                          28

<210> SEQ ID NO 33
<211> LENGTH: 821
<212> TYPE: DNA
<213> ORGANISM: Jatropha curcas

<400> SEQUENCE: 33
cgccacctct attgaagcac caaaagaccc attcaatgcc gcctgaaaag attgaaatat       60
```

```
ttaaatctttt agaaacttgg gccacagaca atgtgcttcc acttcttaaa ccagtagaaa      120
attgctggca accacaaaac tggctgcctg accccacagt accagttgat gaattcactg      180
atcaagtgcg ggccctacgt gatcggacgg ctgaacttcc tgatgattac tttgtagtgc      240
tggtgggtga tatgatcact gaggatgcat tgcctacata tcagaccatg attaatacgc      300
tagacggcgt tagagacgag actggagcaa gccgaaaccc atgggcattg tggactcggg      360
cctggactgc tgaggagaac cgacacggtg atttgctgag gacttacttg tacttgtcgg      420
gtcgggttga tatgttgatg attgagcgga ccgtgcagta tttgattgga gctggcatgg      480
acccaggatc agaaaacaat ccgtacttgg gctttgttta cacgtcattt caagagagag      540
ccacatttgt atcacacggc aatacggcgc gtttagctaa ggacagaggt gatccagtac      600
tggcgcgtat atgcggtacc atagcagcgg acgagaagcg tcacgaaaac gcgtactcta      660
agatcgtcga aaagcttctt gaggtagacc ccacaggagc agtggtagcg attggagata      720
tgatgcggaa gaaaatcacg atgccggccc acttgatgta cgatgggcag gacccgcatt      780
tgtttgatca tttctcggcc gtggctcagc ggcttggagt a                         821

<210> SEQ ID NO 34
<211> LENGTH: 29
<212> TYPE: DNA
<213> ORGANISM: Artificial
<220> FEATURE:
<223> OTHER INFORMATION: PCR primer

<400> SEQUENCE: 34
tataatctag accacagcct gagtctgaa                                         29

<210> SEQ ID NO 35
<211> LENGTH: 30
<212> TYPE: DNA
<213> ORGANISM: Artificial
<220> FEATURE:
<223> OTHER INFORMATION: PCR primer

<400> SEQUENCE: 35
ctcagttctt tcgttgtagc ctaggttagt                                        30

<210> SEQ ID NO 36
<211> LENGTH: 847
<212> TYPE: DNA
<213> ORGANISM: Jatropha curcas

<400> SEQUENCE: 36
ccacagcctg agtctgaagg attctacgat caagtgaaag agctgagaga aagatcaaag       60
gaactttccg atgactattt tgtagtttta gcaggcgaca tgataacaga agaagcgatt      120
ccaacatatc agacgatact taacacttta gatggaactc gagatgagag tggtgtttct      180
ttaagtccct gggccatttg gactcgtgca tggactgctg aagagaatcg acatggcgac      240
cttctcaaca agtatcttta cctctccgga cgagttgaca tgaagatgat tgaaaggact      300
atccaatatt tgataggttg tggaacggat tctaaatttg aaaaacaacc cccttctccg      360
gatttatata cacttcgttc caggagagag caacatttgt ctctcatggc aacacggcga      420
gactgtcaaa ggagaaagga gacacaaagc ttgaacagat atgtggcata attgctgcag      480
atgagaaacg gcatgaaact gcttatgtta agattgtaga gaagttatt t gaggtcgatc      540 cagacgctac gatctcggca tttgccgaca tgatgaggaa aaagattcaa atgccggccc      600
gcttgatgca tgatggtgaa gattataacc tgttcgatca ctacgcagcg gttgctcagc      660
```

```
gtcttggagt gtatactgca aaagactacg cagatatttt ggaatttctg ataggaagat    720
ggaaagtaga caagttgaaa gatttgtctg gccaaggacg taaagctcaa gattttatat    780
gcggattagc tccgaggttt agaaagatag aggaaagagc tcaagaaaga gtcaagaaag    840
caacatc                                                              847
```

<210> SEQ ID NO 37
<211> LENGTH: 29
<212> TYPE: DNA
<213> ORGANISM: Artificial
<220> FEATURE:
<223> OTHER INFORMATION: PCR primer

<400> SEQUENCE: 37

```
ttatttctag acttgcacaa atgtgtcat                                       29
```

<210> SEQ ID NO 38
<211> LENGTH: 28
<212> TYPE: DNA
<213> ORGANISM: Artificial
<220> FEATURE:
<223> OTHER INFORMATION: PCR primer

<400> SEQUENCE: 38

```
caccttata tgaaggacct aggaagat                                         28
```

<210> SEQ ID NO 39
<211> LENGTH: 854
<212> TYPE: DNA
<213> ORGANISM: Jatropha curcas

<400> SEQUENCE: 39

```
cttgcacaaa tgtgtcatat ttctggcatg gcatttaatt ctgagcctgt actttctcct    60
gtaagtgcac gtcctgagca agtagaaaag gtgttgaaga ctcgatacca tgatgccatg    120
acaagactcc agggcaagga gcttgacctg cttattgtaa ttctccctga caacaatggt    180
tctctttatg gtgatttgaa gcggatttgt gagacagatc ttggacttgt ttcccagtgc    240
tgtttaacaa agcatgtctt tagaatgagc aaacaatatc tagccaatgt agcgctgaag    300
ataaatgtga aggttggggg aagaaacact gtacttgttg atgcattatc aaggcgtatt    360
cctttagtca gtgaccggct tactattatt tttggtgctg atgttaccca tcctcatcct    420
ggcgaggact cgagcccatc tattgcagct gttgtggcat ctcaagattg ccagaggtt     480 acaaagtatg ctggtttggt ctgtgctcaa gcccatcgac aagagcttat ccaagatttg    540
ttcaaagagt ggcaagatcc tgtaagaggg aaagtcactg gtggcatgat caaggaactc    600
cttatatctt tccgaagagc aactgggcag aaacctcagc gtattatatt ttacagggat    660
ggtgtcagtg aaggacagtt ctatcaagtt ttgttgtatg aacttgatgc tatccggaag    720
gcttgtgctt ctttagaacc aaattatcag cctcctgtga cgtttgttgt ggttcagaag    780
cgtcacccac caggttgttt gccaataacc atcatgaccg taatgctgtt gacaggagtg    840
ggaatatact tcct                                                      854
```

<210> SEQ ID NO 40
<211> LENGTH: 35
<212> TYPE: DNA
<213> ORGANISM: Artificial
<220> FEATURE:
<223> OTHER INFORMATION: PCR primer

<400> SEQUENCE: 40
acatattcta gattgaggag agatgctgaa gcaaa                               35

<210> SEQ ID NO 41
<211> LENGTH: 31
<212> TYPE: DNA
<213> ORGANISM: Artificial
<220> FEATURE:
<223> OTHER INFORMATION: PCR primer

<400> SEQUENCE: 41
aactcctctc tacgacttcg cctaggtagg t                                   31

<210> SEQ ID NO 42
<211> LENGTH: 629
<212> TYPE: DNA
<213> ORGANISM: Jatropha curcas

<400> SEQUENCE: 42
tatacattat gaagagttta aggcaatggg cagtggagct tttacatgga aatgaaggag    60
aggcagcgtt ggagagctga agaggacgcc ttattacgtg catatgttaa gcaatatggt   120
ccaagggagt ggaaccttgt atcacagcgc atgaacacac ccctaaacag ggatgccaaa   180
tcctgcttag aaaggtggaa gaactacctc aagcctggta taaagaaagg atcacttact   240
gaagaagagc agcgtcttgt tatccgactt caggctaaac acggtaacaa atggaagaaa   300
attgcagctg aagttccagg aagaactgct aagagacttg aaagtggtg ggaagtgttc    360 aaggagaagc agcagagaga gcaaaaggaa ataacaaga caatagaacc aattgacgag    420
ggcaagtacg ataggattct ggagactttt gcagagaagc tagtgaaaga gcgccctgct   480
ccagcatttg tcatggccac ttccaatggg ggcttttac atactgatcc ccctactcct    540
gcaccaacta tgcttccccc atggctttct acttccaaca gcacttctgc tgttaggcca   600
ccctctccat ctgtaaccct aagcctctc                                    629

<210> SEQ ID NO 43
<211> LENGTH: 39
<212> TYPE: DNA
<213> ORGANISM: Artificial
<220> FEATURE:
<223> OTHER INFORMATION: PCR primer

<400> SEQUENCE: 43
aataactcta gacaggtata tatacgtgat caaccattt                          39

<210> SEQ ID NO 44
<211> LENGTH: 32
<212> TYPE: DNA
<213> ORGANISM: Artificial
<220> FEATURE:
<223> OTHER INFORMATION: PCR primer

<400> SEQUENCE: 44
cctcctccga cgatagtcca tacctaggta tt                                 32

<210> SEQ ID NO 45
<211> LENGTH: 678
<212> TYPE: DNA
<213> ORGANISM: Jatropha curcas

<400> SEQUENCE: 45
tatttgaagc actcactaca gagaggtgtc aggagcgact ttctcttgaa agacttgaaa    60

```
ttctgggtga tgcttttctc aaatttgctg ttggacgacg gctttttctt ttgcatgata    120
cccttgatga aggggagctt acaaggagac gctctagtgc tgtaaataat ttgaatttgt    180
tgaaactcgc atgtagaaaa aacttgcagg tatatatacg tgaccaacca tttgatccct    240
gtgaattctt tgctttgggc cgtccttgcc ctagaatttg taccaaggaa tcagaaggaa    300
gcattcattc tcaaaatgga aaccatgcgg caggtcaagc aaaagccagt caagtcagat    360
gcagtaaaaa tcaccattgg ttacataaga aaacaattgc tgatgtagtc gaggctctca    420
ttggagcatt catagtcgat agtggcttta aagcggcaac tgcatttctt aagtggctgg    480
gcatcagtgt ggacttcgaa gcttcaaaag ttattagggt ctgcctagca agcagtagct    540
tcatgccact tgctcctccc atagatattg ttgcccgtga aaatttggtg gggcatcagt    600
ttcaccatag aggattactt ctacaagctt ttgtgcatcc ttcctatggc aagcatggag    660
gaggctgcta tcaggtat                                                  678
```

```
<210> SEQ ID NO 46
<211> LENGTH: 30
<212> TYPE: DNA
<213> ORGANISM: Artificial
<220> FEATURE:
<223> OTHER INFORMATION: PCR primer

<400> SEQUENCE: 46
aataaggtac catacctgat agcagcctcc                                      30

<210> SEQ ID NO 47
<211> LENGTH: 30
<212> TYPE: DNA
<213> ORGANISM: Artificial
<220> FEATURE:
<223> OTHER INFORMATION: PCR primer

<400> SEQUENCE: 47
aataagagct cataatcttc gtgagtgatg                                      30

<210> SEQ ID NO 48
<211> LENGTH: 18
<212> TYPE: DNA
<213> ORGANISM: Jatropha curcas

<400> SEQUENCE: 48
ctgtgcagat agatcatg                                                   18

<210> SEQ ID NO 49
<211> LENGTH: 18
<212> TYPE: DNA
<213> ORGANISM: Jatropha curcas

<400> SEQUENCE: 49
atgacagtag caacatcc                                                   18

<210> SEQ ID NO 50
<211> LENGTH: 18
<212> TYPE: DNA
<213> ORGANISM: Jatropha curcas

<400> SEQUENCE: 50
tggtgcatca tacggctc                                                   18

<210> SEQ ID NO 51
```

```
<211> LENGTH: 20
<212> TYPE: DNA
<213> ORGANISM: Jatropha curcas

<400> SEQUENCE: 51
atgtgaacat tgatatcatg                                              20

<210> SEQ ID NO 52
<211> LENGTH: 19
<212> TYPE: DNA
<213> ORGANISM: Jatropha curcas

<400> SEQUENCE: 52
ggcaaggagc ttgacctgc                                               19

<210> SEQ ID NO 53
<211> LENGTH: 19
<212> TYPE: DNA
<213> ORGANISM: Jatropha curcas

<400> SEQUENCE: 53
tcagcgctac attggctag                                               19

<210> SEQ ID NO 54
<211> LENGTH: 18
<212> TYPE: DNA
<213> ORGANISM: Jatropha curcas

<400> SEQUENCE: 54
agagctgaag aggacgcc                                                18

<210> SEQ ID NO 55
<211> LENGTH: 20
<212> TYPE: DNA
<213> ORGANISM: Jatropha curcas

<400> SEQUENCE: 55
caggcttgag gtagttcttc                                              20

<210> SEQ ID NO 56
<211> LENGTH: 18
<212> TYPE: DNA
<213> ORGANISM: Jatropha curcas

<400> SEQUENCE: 56
gccagtcaag tcagatgc                                                18

<210> SEQ ID NO 57
<211> LENGTH: 18
<212> TYPE: DNA
<213> ORGANISM: Jatropha curcas

<400> SEQUENCE: 57
ccacactgat gcccagcc                                                18

<210> SEQ ID NO 58
<211> LENGTH: 18
<212> TYPE: DNA
<213> ORGANISM: Jatropha curcas

<400> SEQUENCE: 58
tgtggatgag gatggcag                                                18
```

```
<210> SEQ ID NO 59
<211> LENGTH: 18
<212> TYPE: DNA
<213> ORGANISM: Jatropha curcas

<400> SEQUENCE: 59
ccagccaatg tacttcac                                                 18

<210> SEQ ID NO 60
<211> LENGTH: 18
<212> TYPE: DNA
<213> ORGANISM: Jatropha curcas

<400> SEQUENCE: 60
cagctgttgc acagcggc                                                 18

<210> SEQ ID NO 61
<211> LENGTH: 18
<212> TYPE: DNA
<213> ORGANISM: Jatropha curcas

<400> SEQUENCE: 61
ggaggtagcc gacaaacg                                                 18

<210> SEQ ID NO 62
<211> LENGTH: 18
<212> TYPE: DNA
<213> ORGANISM: Jatropha curcas

<400> SEQUENCE: 62
gtggactggg cctggact                                                 18

<210> SEQ ID NO 63
<211> LENGTH: 18
<212> TYPE: DNA
<213> ORGANISM: Jatropha curcas

<400> SEQUENCE: 63
tctgatcctg ggtccatg                                                 18

<210> SEQ ID NO 64
<211> LENGTH: 18
<212> TYPE: DNA
<213> ORGANISM: Jatropha curcas

<400> SEQUENCE: 64
ttcgttccag gagagagc                                                 18

<210> SEQ ID NO 65
<211> LENGTH: 20
<212> TYPE: DNA
<213> ORGANISM: Jatropha curcas

<400> SEQUENCE: 65
tcgacctcaa ataacttctc                                               20

<210> SEQ ID NO 66
<211> LENGTH: 24
<212> TYPE: DNA
<213> ORGANISM: Jatropha curcas

<400> SEQUENCE: 66
ggtttggacc agaaacaaat aaat                                          24
```

```
<210> SEQ ID NO 67
<211> LENGTH: 20
<212> TYPE: DNA
<213> ORGANISM: Jatropha curcas

<400> SEQUENCE: 67
cacccatgta gtgaccatcc                                              20

<210> SEQ ID NO 68
<211> LENGTH: 20
<212> TYPE: DNA
<213> ORGANISM: Jatropha curcas

<400> SEQUENCE: 68
gggtggtggt tcaatcattc                                              20

<210> SEQ ID NO 69
<211> LENGTH: 20
<212> TYPE: DNA
<213> ORGANISM: Jatropha curcas

<400> SEQUENCE: 69
tctccgctag tctcttgtgc                                              20

<210> SEQ ID NO 70
<211> LENGTH: 25
<212> TYPE: DNA
<213> ORGANISM: Jatropha curcas

<400> SEQUENCE: 70
ccttgtgtgg atccagtttt caagg                                        25

<210> SEQ ID NO 71
<211> LENGTH: 24
<212> TYPE: DNA
<213> ORGANISM: Jatropha curcas

<400> SEQUENCE: 71
gcttctccag aaagagcgag ccga                                         24

<210> SEQ ID NO 72
<211> LENGTH: 24
<212> TYPE: DNA
<213> ORGANISM: Jatropha curcas

<400> SEQUENCE: 72
caacagtaga caagcctgaa gagg                                         24

<210> SEQ ID NO 73
<211> LENGTH: 25
<212> TYPE: DNA
<213> ORGANISM: Jatropha curcas

<400> SEQUENCE: 73
gcaatcttgt actcaaccac aacag                                        25

<210> SEQ ID NO 74
<211> LENGTH: 23
<212> TYPE: DNA
<213> ORGANISM: Jatropha curcas

<400> SEQUENCE: 74
ctcctgaaga aatcggttca gtg                                          23
```

<210> SEQ ID NO 75
<211> LENGTH: 22
<212> TYPE: DNA
<213> ORGANISM: Jatropha curcas

<400> SEQUENCE: 75
tgaccgttca agaatggatg ag                                    22

<210> SEQ ID NO 76
<211> LENGTH: 19
<212> TYPE: DNA
<213> ORGANISM: Jatropha curcas

<400> SEQUENCE: 76
cttctccagc aacgggctc                                        19

<210> SEQ ID NO 77
<211> LENGTH: 19
<212> TYPE: DNA
<213> ORGANISM: Jatropha curcas

<400> SEQUENCE: 77
ggagttccgc ctgaggaag                                        19

<210> SEQ ID NO 78
<211> LENGTH: 21
<212> TYPE: DNA
<213> ORGANISM: Jatropha curcas

<400> SEQUENCE: 78
ggttgaggaa ggaggtggaa g                                     21

<210> SEQ ID NO 79
<211> LENGTH: 21
<212> TYPE: DNA
<213> ORGANISM: Jatropha curcas

<400> SEQUENCE: 79
ccaccattca cacttggtca g                                     21

<210> SEQ ID NO 80
<211> LENGTH: 22
<212> TYPE: DNA
<213> ORGANISM: Jatropha curcas

<400> SEQUENCE: 80
agcaatcaag cctatattgg gc                                    22

<210> SEQ ID NO 81
<211> LENGTH: 20
<212> TYPE: DNA
<213> ORGANISM: Jatropha curcas

<400> SEQUENCE: 81
ccagagaact cctcggttgg                                       20

<210> SEQ ID NO 82
<211> LENGTH: 32
<212> TYPE: DNA
<213> ORGANISM: Tobacco rattle virus

<400> SEQUENCE: 82

-continued

```
ttaagacgag tttttcttat tagacgctct ct                              32

<210> SEQ ID NO 83
<211> LENGTH: 32
<212> TYPE: DNA
<213> ORGANISM: Tobacco rattle virus

<400> SEQUENCE: 83
atggaagaca agtcattggt caccttgaag aa                              32

<210> SEQ ID NO 84
<211> LENGTH: 25
<212> TYPE: DNA
<213> ORGANISM: Tobacco rattle virus

<400> SEQUENCE: 84
gatcaatcaa gatcagtcga gaatg                                      25

<210> SEQ ID NO 85
<211> LENGTH: 25
<212> TYPE: DNA
<213> ORGANISM: Tobacco rattle virus

<400> SEQUENCE: 85
gatggacatt gttactcaag gaagc                                      25
```